United States Patent
Fu et al.

(10) Patent No.: US 10,336,829 B2
(45) Date of Patent: Jul. 2, 2019

(54) INTRACELLULAR DELIVERY COMPOUNDS

(71) Applicant: Sorrento Therapeutics, Inc., San Diego, CA (US)

(72) Inventors: Yanwen Fu, San Diego, CA (US); Gunnar Jörg Floris Kaufmann, San Diego, CA (US); Heehyoung Lee, Arcadia, CA (US); Ingale Sampat Lalaso, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/298,813

(22) Filed: Oct. 20, 2016

(65) Prior Publication Data

US 2017/0107289 A1   Apr. 20, 2017

Related U.S. Application Data

(60) Provisional application No. 62/382,828, filed on Sep. 2, 2016, provisional application No. 62/327,130, filed on Apr. 25, 2016, provisional application No. 62/244,176, filed on Oct. 20, 2015.

(51) Int. Cl.
| | |
|---|---|
| *C07K 16/00* | (2006.01) |
| *A61P 35/00* | (2006.01) |
| *C12N 15/09* | (2006.01) |
| *C07K 16/28* | (2006.01) |
| *C07K 16/18* | (2006.01) |
| *A61K 47/68* | (2017.01) |

(52) U.S. Cl.
CPC ...... *C07K 16/2863* (2013.01); *A61K 47/6807* (2017.08); *A61K 47/6843* (2017.08); *A61K 47/6849* (2017.08); *C07K 16/18* (2013.01); *C07K 16/2818* (2013.01); *C07K 2317/21* (2013.01); *C07K 2317/24* (2013.01); *C07K 2317/73* (2013.01); *C07K 2317/77* (2013.01)

(58) Field of Classification Search
CPC ............ A61K 47/48561; A61K 39/395; A61K 47/6807; A61K 47/6843; A61K 47/6849; C07K 2317/24; C07K 2317/77
USPC ....... 514/44; 435/6.1, 91.1, 91.31, 455, 458; 530/287.3, 300, 350
See application file for complete search history.

(56) References Cited

U.S. PATENT DOCUMENTS

| | | |
|---|---|---|
| 6,881,831 B2 | 4/2005 | Iyer et al. |
| 6,921,812 B1 | 7/2005 | Prakash et al. |
| 2003/0026801 A1* | 2/2003 | Weiner ............ A61K 39/39541 424/144.1 |

(Continued)

FOREIGN PATENT DOCUMENTS

| | | | | |
|---|---|---|---|---|
| WO | 01/40515 A1 | 6/2001 | | |
| WO | WO-2014202775 A1 * | 12/2014 | ......... | A61K 31/5517 |
| WO | WO-2015175357 A1 * | 11/2015 | ......... | C07K 16/2827 |

OTHER PUBLICATIONS

Angewandte Chemie International Edition, vol. 54, No. 36, pp. 1-11 (Year: 2015).*

(Continued)

*Primary Examiner* — Jane J Zara
(74) *Attorney, Agent, or Firm* — Womble Bond Dickinson (US) LLP; Danielle L. Herritt; Scott R. Breining

(57) ABSTRACT

Provided are compounds having the Formula I:

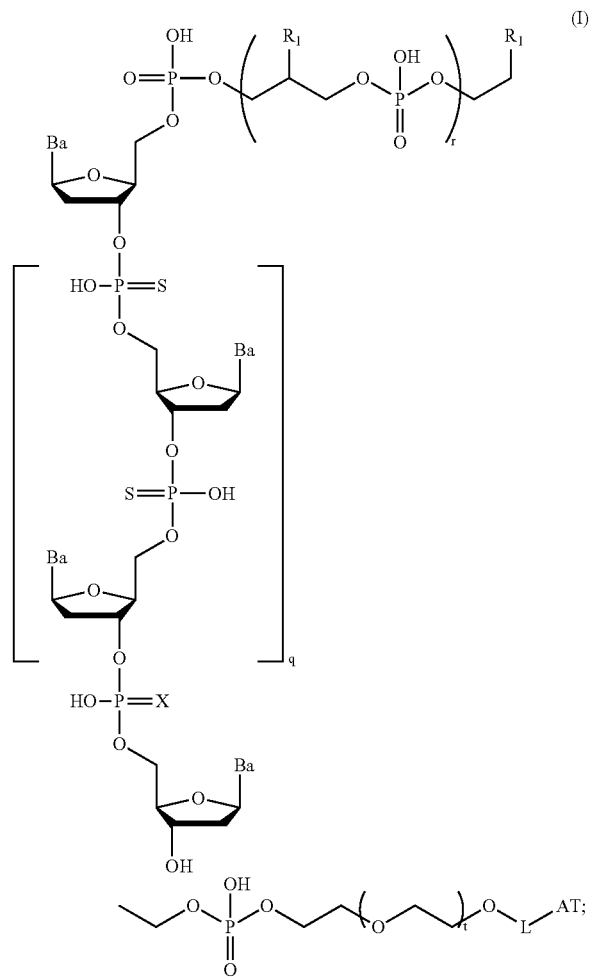

pharmaceutically acceptable salts thereof, pharmaceutical compositions thereof, and their use in the intracellular delivery of antibodies.

29 Claims, 25 Drawing Sheets

Specification includes a Sequence Listing.

(56) References Cited

U.S. PATENT DOCUMENTS

2003/0139586 A1 7/2003 Cook et al.
2016/0289333 A1* 10/2016 Gorlatov ............... C07K 16/00

OTHER PUBLICATIONS

Overhoff et al.,"Phosphorothioate-stimulated uptake of short interfering RNA by human cells," EMBO Rep. 6(12): 1176-81 (2005).
Detzer, et al. "Phosphorothioate-stimulated cellular uptake of siRNA: a cell culture model for mechanistic studies," Curr Pharm Des. 14(34):3666-73 (2008).

* cited by examiner

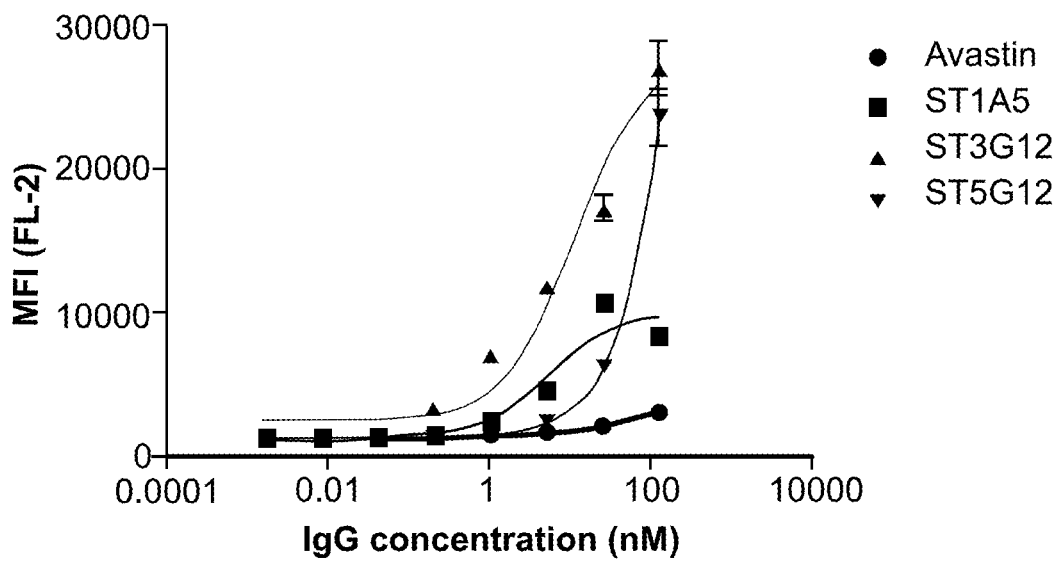
FIG. 8A  Anti-STAT3 binding in MDA-MB-468 cells
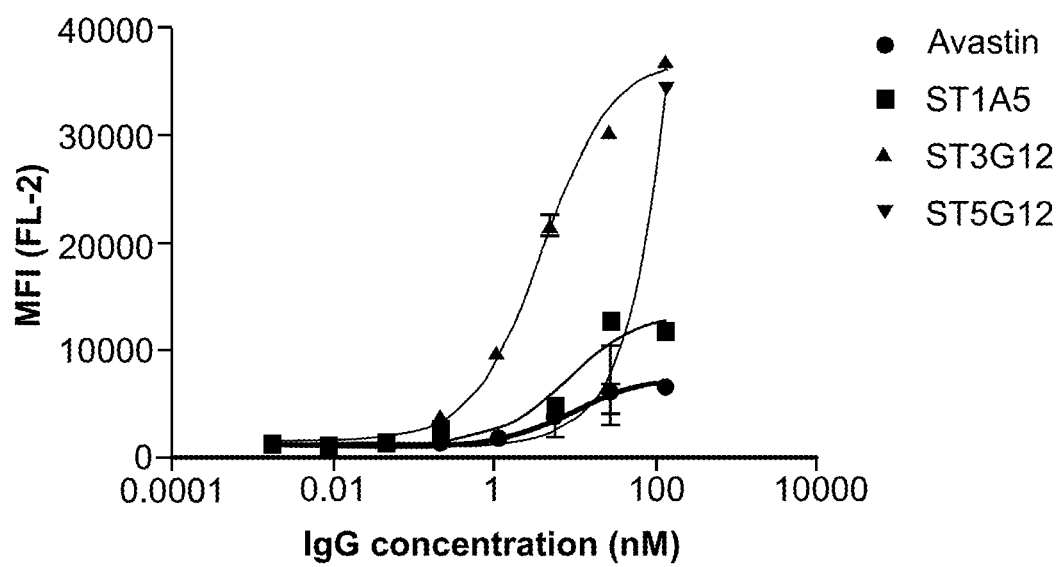
FIG. 8B  Anti-STAT3 binding in U251 cells

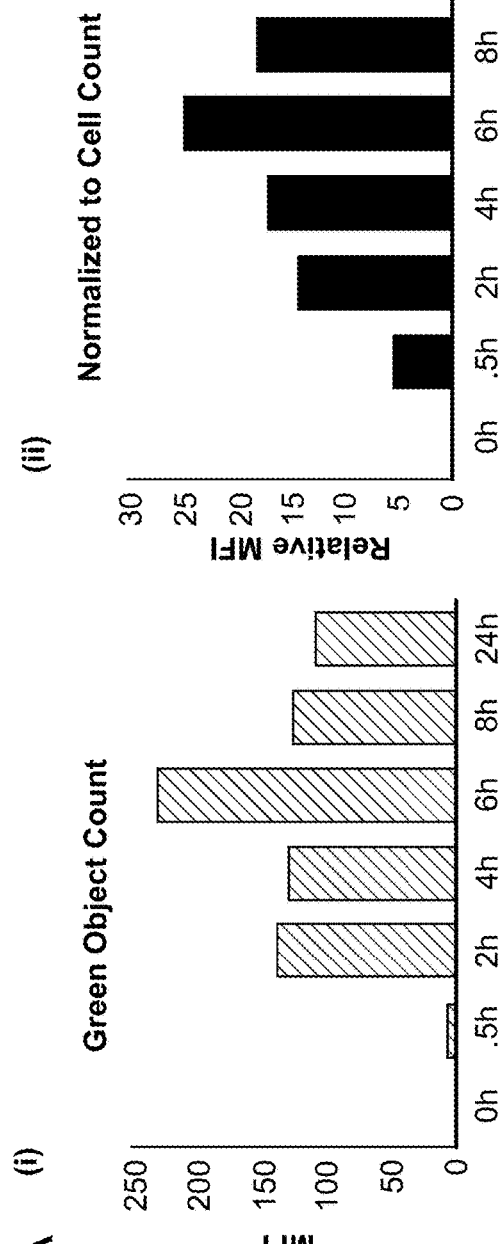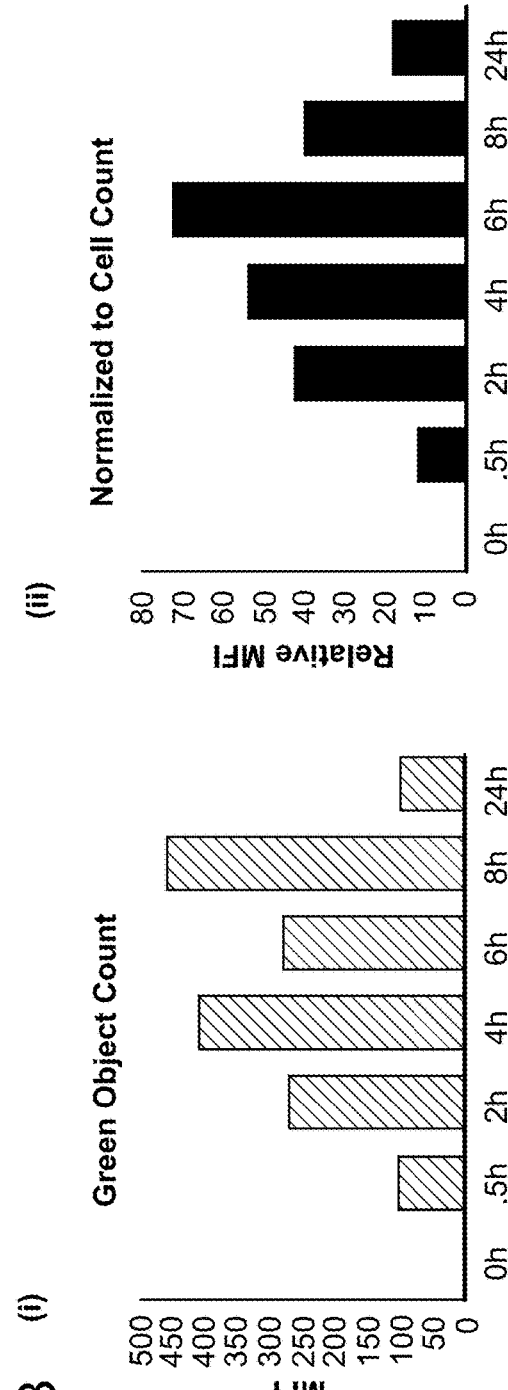
FIG. 14A
FIG. 14B

|  | STAT3 (3G12)-unmodified superblock | STAT3 (3G12)-Or5 Superblock |
|---|---|---|
| HillSlope | 1.456 | 1.588 |
| EC50 | 122.0 | 186.5 |

01052015
Binding ELISA
Hu-IgO Detection

|  | STAT3 (3G12)-Unmodified Superblock | STAT3 (3G12)-Or5 Superblock |
|---|---|---|
| HillSlope | 0.9652 | 0.9634 |
| EC50 | 25.68 | 64.34 |

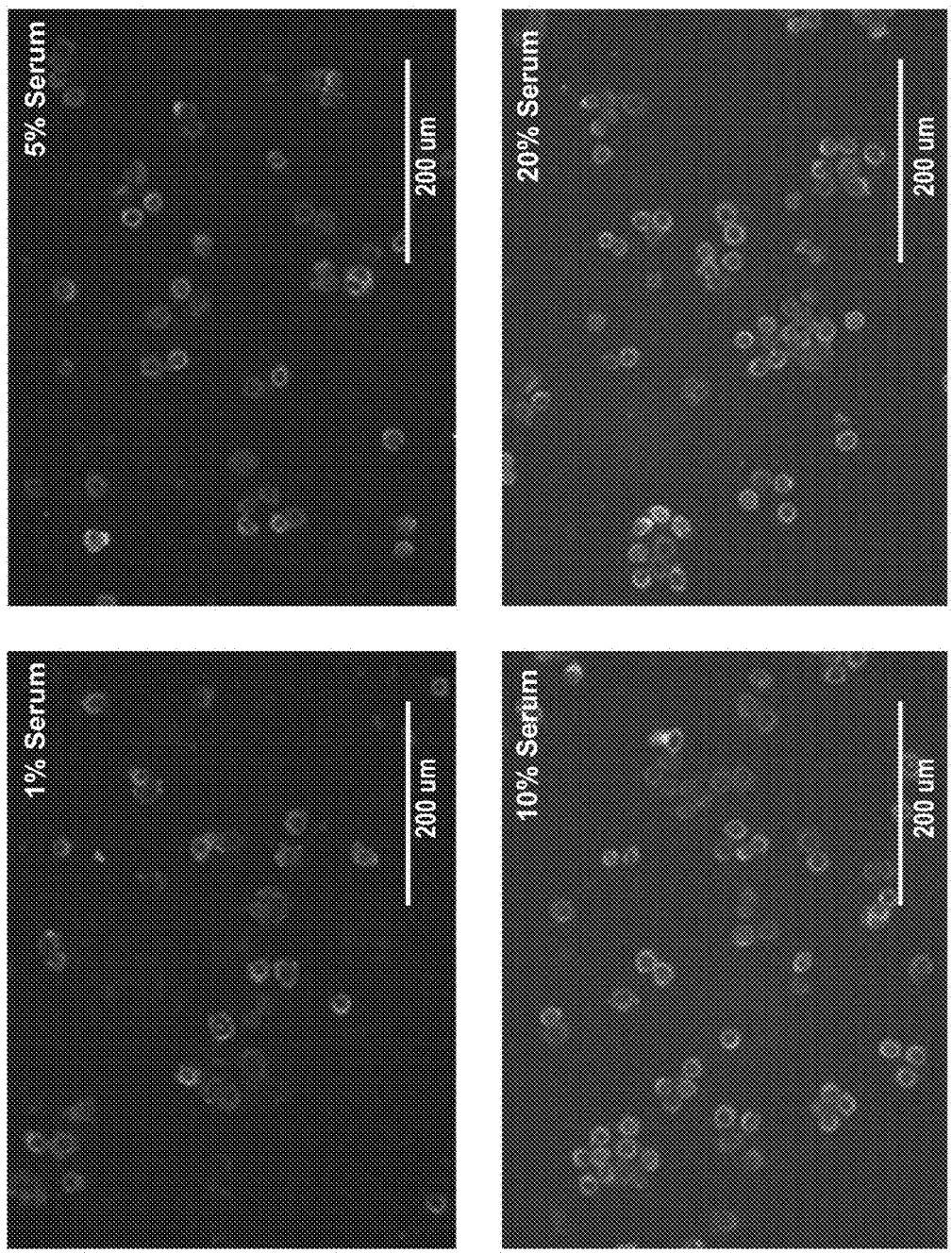

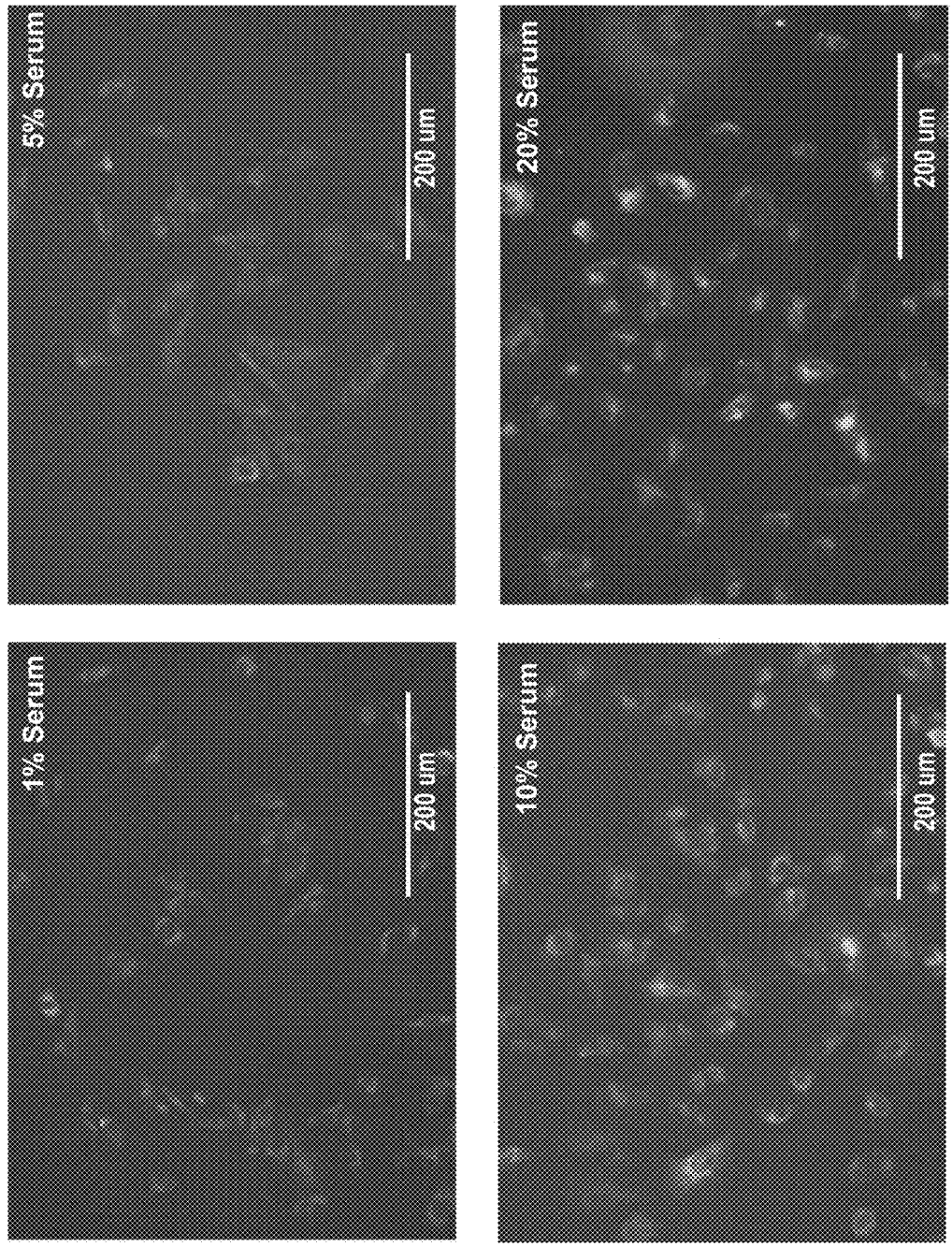

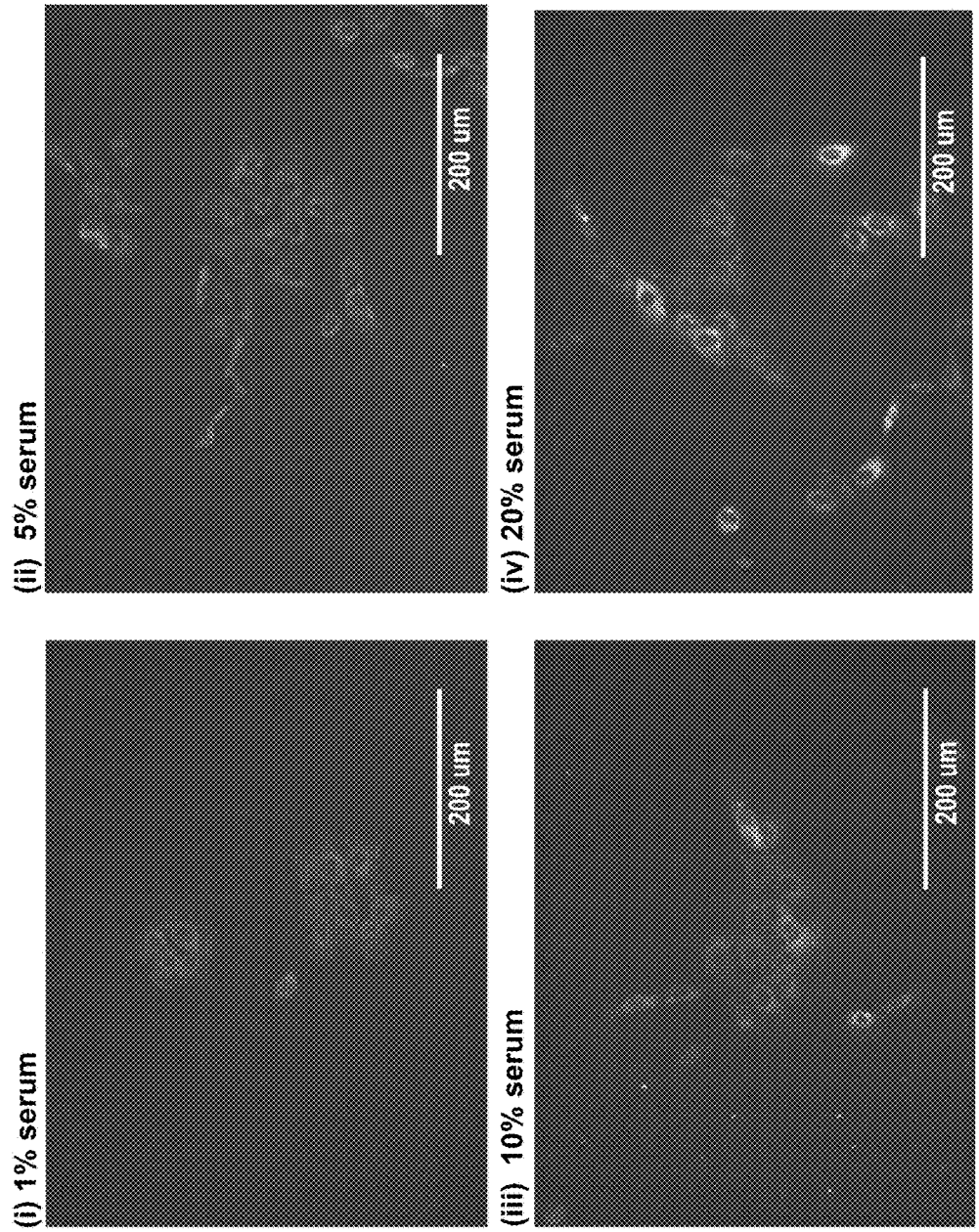

INTRACELLULAR DELIVERY COMPOUNDS

RELATED APPLICATIONS

This application claims priority to U.S. Provisional Application No. 62/382,828, filed Sep. 2, 2016, U.S. Provisional Application No. 62/327,130, filed Apr. 25, 2016, and U.S. Provisional Application No. 62/244,176, filed Oct. 20, 2015. The contents of each of the aforementioned applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 29, 2016, is named 126036-06302_SL.txt and is 5,192 bytes in size.

TECHNICAL FIELD

The present disclosure is directed in part to compounds that are useful for the intracellular delivery of, or to enhance the intracellular delivery of, one or more peptides or proteins (e.g., antibodies).

BACKGROUND

Therapeutic peptides and proteins (e.g., antibodies) have emerged as useful and promising drug targets for the treatment of various diseases. Protein and peptide therapeutics have several advantages over traditional small molecules based drugs. In one instance, they are often responsible for performing specific biological functions that cannot be mimicked by traditional therapies. Unlike most small molecule drugs, proteins and peptides are also typically well-tolerated in vivo and usually do not interfere with non-targeted biological processes. Despite these advantages, therapeutic peptides and proteins (e.g., antibodies) are restricted by their limited access to intracellular compartments. Additionally, even in instances where intracellular admission is achieved, peptides and proteins (e.g., antibodies) may be partially degraded, leading to incomplete presentation for target recognition. Given the therapeutic potential for peptides and proteins (e.g., antibodies), and the continuing need to combat diseases, means for delivering, or enhancing the delivery of, intact peptides and proteins (e.g., antibodies) remains an attractive area of investigation.

SUMMARY

It has now been found that the compounds described herein, and pharmaceutically acceptable compositions thereof, effectively deliver intact antibodies intracellularly. See e.g., FIG. 14A, FIG. 14B, FIG. 15A, and FIG. 15B. Such compounds include those having the Formula I:

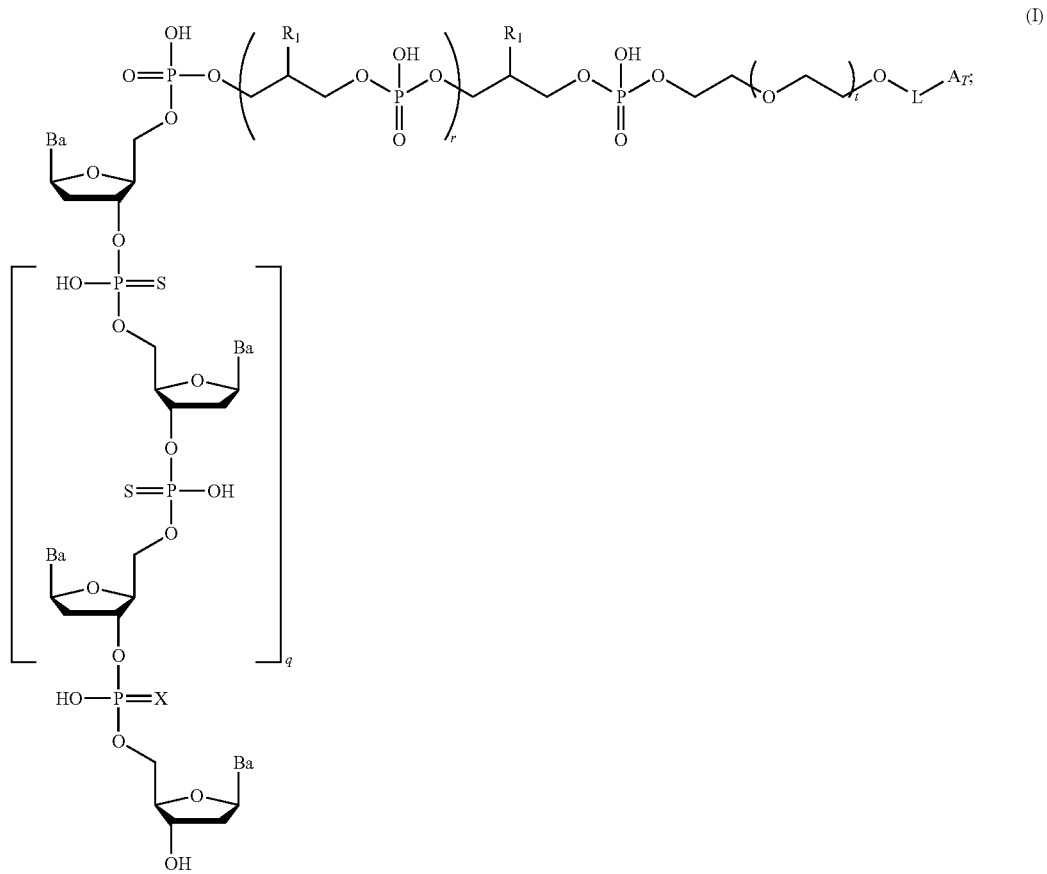

or a pharmaceutically acceptable salt thereof, wherein each of X, q, Ba, $R^1$, r, t, L, and $A_T$ are as defined and described herein.

Also provided are methods of using the disclosed compounds in the treatment of one of more diseases and disorders described herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 8A is a graph that shows the results of a cell binding assay to assess binding of anti-STAT3 antibodies ST1A5, ST3G12 and ST5G12 to cellular antigens in MDA-MB-435 cells. MFI refers to the mean fluorescent intensity that was detected.

FIG. 8B is a graph that shows the results of a cell binding assay to assess binding of anti-STAT3 antibodies ST1A5, ST3G12 and ST5G12 to cellular antigens in U251 cells.

FIG. 14A is a graph that shows the results of a time course experiment showing compound 901a accumulation in MDA-MB-468 cells. The results show the prolonged accumulation of compound 901a in tumor cells.

FIG. 14B is a graph that shows the same experiments described in FIG. 14A, performed in MCF-10A cells. The results show that accumulation of compound 901a decreased after 6 hours.

FIG. 15A shows microscopic images in which MDA-MB-468 triple negative breast cancer cells were treated with 10 ug/ml of the compound 901a in increasing proportions of human serum (1%, 5%, 10% and 20%).

FIG. 15B is a microscopic image of compound 901a accumulated in U251 cells.

FIG. 15C is a microscopic image of compound 901a uptake in MCF10A human normal breast epithelial cells.

FIG. 26 shows the HPLC-HIC (hydrophobic interaction chromatograpy) of anti-Stat3 IgG ST3G12 and compounds 901a and 904a.

DETAILED DESCRIPTION OF CERTAIN EMBODIMENTS

1. General Description of Compounds

Figure 1:
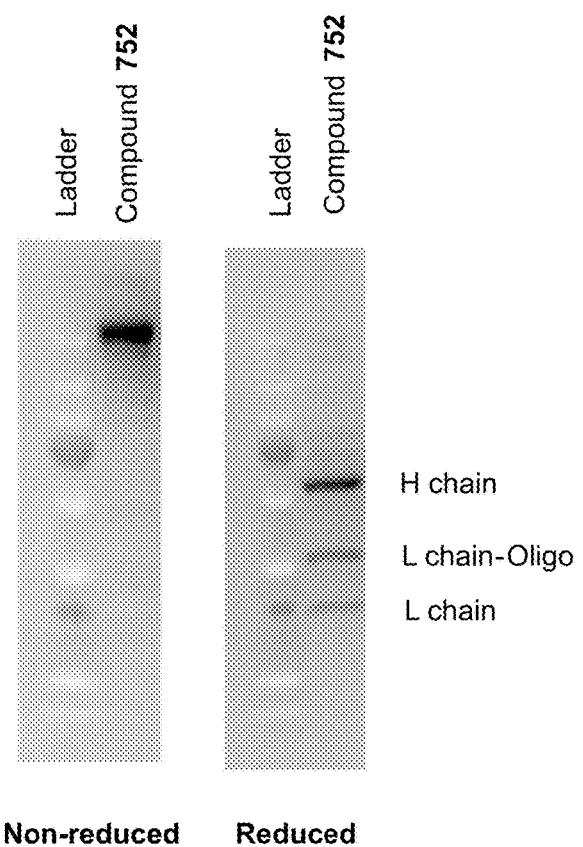
FIG. 1 shows the SDS-PAGE characterization of compound 752, a compound of Formula I where $A_T$ is anti-VEGFR2 IgG.

In certain embodiments, the present disclosure provides a compound of Formula I:

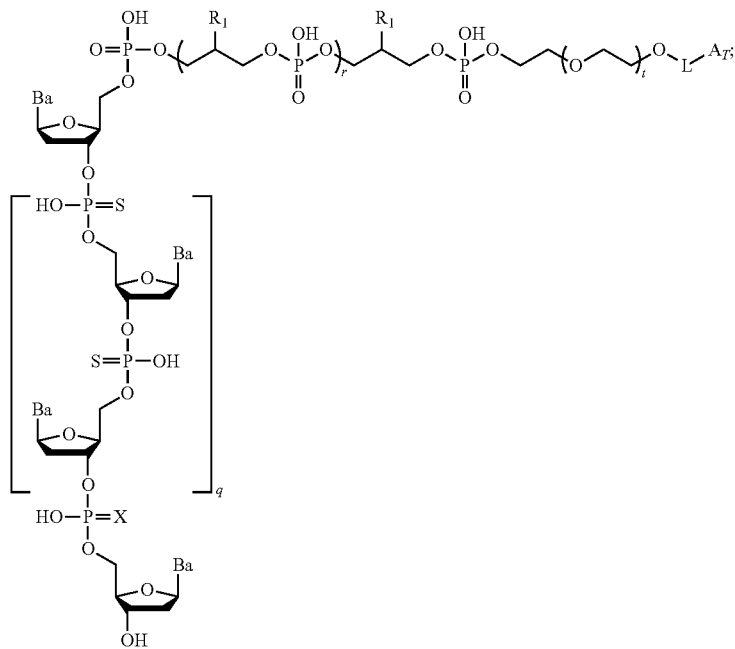

(I)

or a pharmaceutically acceptable salt thereof, wherein
each Ba is independently selected from adenine (A), guanine (G), cytosine (C), and thymine (T);
X is O or S
each $R^1$ is independently selected from hydrogen and $(C_1-C_6)$alkyl substituted with a fluorophore;
q is an integer from 12 to 35;
r is an integer from 1 to 10;
t is an integer from 1 to 10;
L is —$CH_2$—$R^2$—*;
$R^2$ is —$(C_1-C_6)$alkyl substituted with 1 or 2 groups selected from —C(=O)$NR^a$, —$NR^aC$(=O)$R^b$, —$NR^aC$(=O)$R^d$, =$NOR^e$, —$NR^a$, —$NR^aR^b$, —$OR^b$, —S(O)$_kR^b$, —$NR^aS(O)_2R^b$, —S(O)$_2NR^aR^b$, —S(O)$_2NR^a$, —C(=O)$OR^b$, —OC(=O)$OR^b$, —OC(=O)$R^b$, —C(=O)$NR^aR^b$, —$NR^aC$(=O)$R^b$, —$NR^aC$(=O)$OR^b$, —OC(=O)$NR^aR^b$, phenyl, —OC(=O)$NR^a$, —$NR^aC$(=O)$NR^aR^b$, —$NR^aC$(=O)$NR^a$, —$NR^a$(C=S)$NR^aR^b$, —$NR^a$(C=S)$NR^a$, and —C(=O)$R^b$;
k is 0, 1, or 2;
each $R^a$ is independently hydrogen or $(C_1-C_6)$alkyl optionally substituted with $R^f$;
each $R^b$ is independently $(C_1-C_6)$alkyl optionally substituted with $R^f$ or —C(=O)$R^f$;
$R^d$ is —[$(C_1-C_6)$alkyl-O—$(C_1-C_6)$alkyl]$_v$C(=O)NH;
$R^e$ is —[$(C_1-C_6)$alkyl-O—$(C_1-C_6)$alkyl]$_p$C(=O);
each $R^f$ is independently

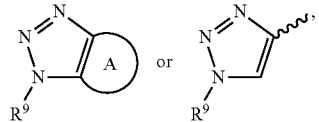

wherein the wavy bond indicates the point of attachment to the $(C_1-C_6)$alkyl defined by $R^a$, or the $(C_1-C_6)$alkyl or carbonyl each defined by $R^b$;
$R^g$ is $(C_1-C_6)$alkyl or —[$(C_1-C_6)$alkyl-O—$(C_1-C_6)$alkyl]$_w$C(=O)NH;

ring A is

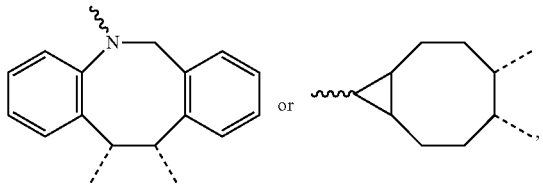

wherein the dashed bonds indicate the points of attachment to the triazolyl of $R^f$, and the wavy bond indicates the point of attachment to the $(C_1-C_6)$alkyl defined by $R^a$, or the $(C_1-C_6)$alkyl or carbonyl each defined by $R^b$;

p is an integer from 1 to 10;
v is an integer from 1 to 10;
w is an integer from 2 to 12;
* indicates the point of attachment to $A_T$; and
$A_T$ is an antibody.

2. Compounds and Definitions

The terms adenine (A), guanine (G), cytosine (C), and thymine (T) refer to the DNA nucleobases having the following structures:

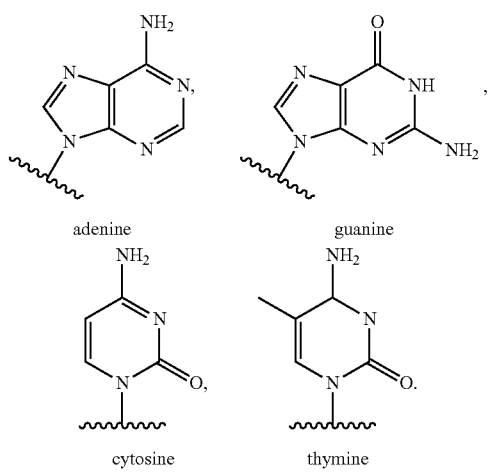

adenine    guanine
cytosine   thymine

The term "fluorophore" means a fluorescent chemical compound (substituent at $R^1$) that is capable of re-emitting light upon excitation. If present, the fluorophore motif on the compounds of Formula I should not significantly diminish the cellular internalization properties of the compound. In one aspect, the fluorophore is intended to serve as a molecular probe for in vitro observation. Thus, in one aspect, the fluorophore is not intended to contribute to the therapeutic properties of the compounds of Formula I. Fluorophores include, but are not limited to, coumarin based dyes (e.g., hydroxycoumarin, aminocoumarin, methoxycoumarin), fluorescein based dyes (e.g., fluorescein and carboxyfluorescein), $SO_3$-based conjugated systems (e.g., Alexa Fluor® 350, Alexa Fluor® 405, Alexa Fluor® 488, Alexa Fluor® 532, Alexa Fluor® 546, Alexa Fluor® 555, Alexa Fluor® 568, Alexa Fluor® 594, Alexa Fluor® 647, Alexa Fluor® 680, Alexa Fluor® 750, Texas Red®, Cy®5), boron systems (e.g., Bodipy®), and tetramethylrhodamine.

The term "antibody" is used in the broadest sense and includes monoclonal antibodies, polyclonal antibodies, multispecific antibodies (including bispecific antibodies), antibody fragments that can bind an antigen (including, Fab', F'(ab)$_2$, Fv, single chain antibodies, diabodies), and recombinant peptides comprising the foregoing as long as they exhibit the desired biological activity and antigen binding specificity.

In one embodiment, an antibody is a full length or intact antibody. A full length antibody comprises four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the antibody may be identical to the human germline sequences, or may be naturally or artificially modified.

The disclosed compounds may exist in various stereoisomeric forms. Stereoisomers are compounds that differ only in their spatial arrangement. Diastereomers are stereoisomers that contain two or more asymmetrically substituted carbon atoms.

As used herein, a hyphen ("-") at the beginning or end of a recited group designates the point at which a recited group is attached to a defined group. For example, —$SO_2$—($C_1$-$C_3$)alkyl-NH($C_1$-$C_3$)alkyl (means that the group is attached via the sulfonyl.

When the stereochemistry of a disclosed compound is named or depicted by structure, it is to be understood that one of the encompassed stereoisomers or any mixture of the encompassed stereoisomers are included. It is to be further understood that the stereoisomeric purity of the named or depicted stereoisomer is at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, it is to be understood that the name or structure encompasses one stereoisomer free of other stereoisomers, mixtures of stereoisomers, or mixtures of stereoisomers in which one or more stereoisomers is enriched relative to the other stereoisomer(s). For example, the name or structure may encompass one stereoisomer free of other diastereomers, mixtures of stereoisomers, or mixtures of stereoisomers in which one or more diastereomers is enriched relative to the other diastereomer(s).

Pharmaceutically acceptable salts of the compounds herein are contemplated. For use in medicines, the salts of the compounds described herein refer to non-toxic "pharmaceutically acceptable salts." Pharmaceutically acceptable salt forms include pharmaceutically acceptable acidic/anionic or basic/cationic salts.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, organic or inorganic carriers, excipients or diluents suitable for pharmaceutical applications.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "effective amount" as used herein, refers to an amount of a compound disclosed herein, which is sufficient to effect treatment of a disease when administered to a subject. A therapeutically effective amount will vary depending upon the relative activity of the compound and depending upon the subject and disease condition being treated, the weight and age of the subject, the severity of the disease condition, the manner of administration and the like, which can readily be determined by one of ordinary skill in the art.

3. Description of Exemplary Compounds

In a first embodiment, the present disclosure provides a compound of Formula I:

In a second embodiment, $R^2$ in Formula I is $-(C_1\text{-}C_6)$alkyl substituted with $-C(=O)NR^a$, $-NR^aC(=O)R^b$, $-NR^aC(=O)R^d$, $=NOR^e$, $-NR^a$, $-NR^aR^b$, $-OR^b$, $-S(O)_kR^b$, $-NR^aS(O)_2R^b$, $-S(O)_2NR^aR^b$, $-S(O)_2NR^a$, $-C(=O)OR^b$, $-OC(=O)OR^b$, $-OC(=O)R^b$, $-C(=O)NR^aR^b$, $-NR^aC(=O)R^b$, $-NR^aC(=O)OR^b$, $-OC(=O)NR^aR^b$, $-OC(=O)NR^a$, $-NR^aC(=O)NR^aR^b$, $-NR^aC(=O)NR^a$, $-NR^a(C=S)NR^aR^b$, $-NR^a(C=S)NR^a$, or $-C(=O)R^b$, wherein the remaining variables are as described above for Formula I.

In a third embodiment, $R^2$ in Formula I is $-(C_1\text{-}C_6)$alkyl substituted with $-C(=O)NR^a$, $-NR^aC(=O)R^b$, $-NR^aC(=O)R^d$, $=NOR^e$, $-NR^a$, $-NR^aR^b$, $-OR^b$, $-S(O)_2NR^aR^b$, $-S(O)_2NR^a$, $-C(=O)OR^b$, $-C(=O)NR^aR^b$, $-NR^aC(=O)R^b$, $-NR^aC(=O)OR^b$, $-NR^aC(=O)NR^aR^b$, $-NR^aC(=O)NR^a$, or $-C(=O)R^b$, wherein the remaining variables are as described above for Formula I and the second embodiment.

In a fourth embodiment, $R^2$ in Formula I is $-(C_1\text{-}C_6)$alkyl-$NR^aC(=O)R^d$, $-(C_1\text{-}C_6)$alkyl-$NR^aC(=O)R^b$, or $-(C_1\text{-}C_6)$alkyl($=NO)R^e$, wherein the remaining variables are as described above for Formula I and the second or third embodiment.

In a fifth embodiment, $R^d$ in Formula I is $-[(C_1\text{-}C_4)\text{alkyl-O-}(C_1\text{-}C_4)\text{alkyl}]_vC(=O)NH$, wherein the remaining variables are as described above for Formula I and the second, third, or fourth embodiment.

In a sixth embodiment, $R^e$ in Formula I is $-[(C_1\text{-}C_4)\text{alkyl-O-}(C_1\text{-}C_4)\text{alkyl}]_pC(=O)$, wherein the remaining variables are as described above for Formula I and the second, third, fourth, or fifth embodiment.

In a seventh embodiment, $R^g$ in Formula I is $-[(C_1\text{-}C_4)\text{alkyl-O-}(C_1\text{-}C_4)\text{alkyl}]_vC(=O)NH$, wherein the remaining variables are as described above for Formula I and the second, third, fourth, fifth, or sixth embodiment.

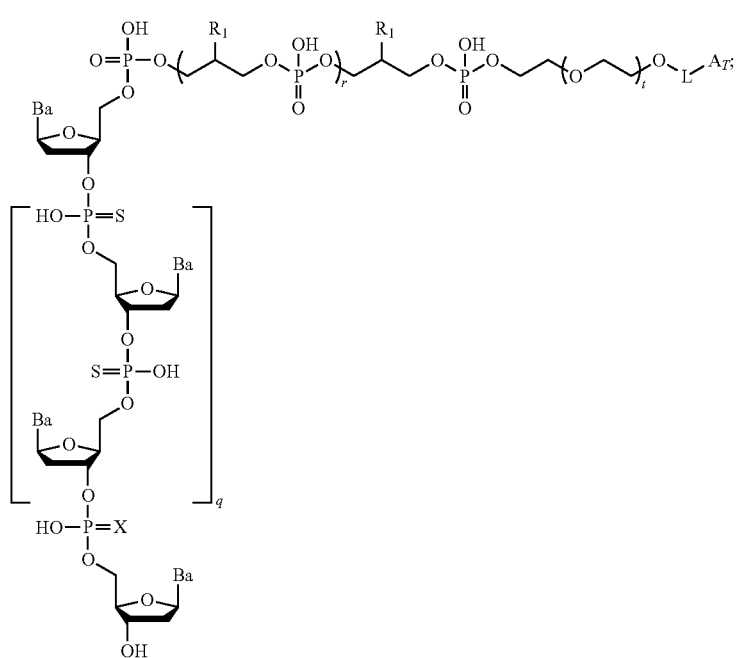
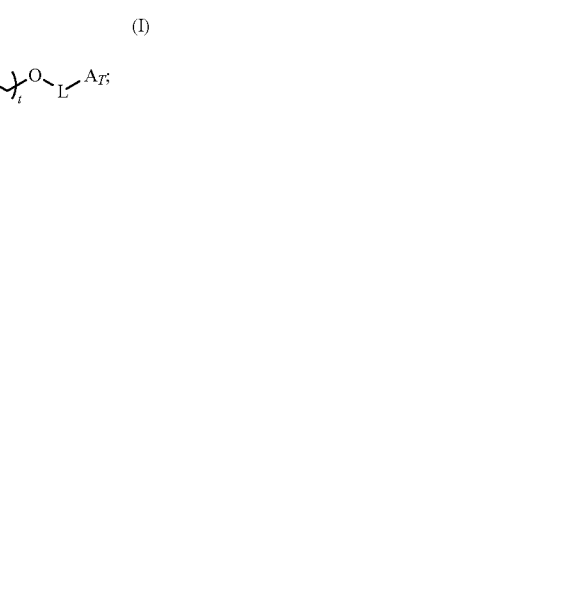

(I)

or a pharmaceutically acceptable salt thereof, wherein the variables are as described above.

In an eighth embodiment, $R^a$ in Formula I is independently selected from hydrogen and $(C_1\text{-}C_6)$alkyl, wherein the remaining variables are as described above for Formula I and the second, third, fourth, fifth, sixth, or seventh embodiment.

In a ninth embodiment, $R^b$ in Formula I is $(C_1-C_6)$alkyl substituted with $R^f$ or —C(=O)$R^f$, wherein the remaining variables are as described above for Formula I and the second, third, fourth, fifth, sixth, seventh, or eighth embodiment.

In a tenth embodiment, p in Formula I is an integer from 1 to 6, wherein the remaining variables are as described above for Formula I and the first, second, third, fourth, fifth, sixth, seventh, eighth, or ninth embodiment. Alternatively, p in Formula I is an integer from 1 to 4, wherein the remaining variables are as described above for Formula I and the first, second, third, fourth, fifth, sixth, seventh, eighth, or ninth embodiment.

In an eleventh embodiment, v in Formula I is an integer from 1 to 6, wherein the remaining variables are as described above for Formula I and the first, second, third, fourth, fifth, sixth, seventh, eighth, ninth, or tenth embodiment. Alternatively, v in Formula I is an integer from 1 to 4, wherein the remaining variables are as described above for Formula I and the first, second, third, fourth, fifth, sixth, seventh, eighth, ninth, or tenth embodiment.

In a twelfth embodiment, w in Formula I is an integer from 2 to 10, wherein the remaining variables are as described above for Formula I and the first, second, third, fourth, fifth, sixth, seventh, eighth, ninth, tenth, or eleventh embodiment. Alternatively, w in Formula I is an integer from 2 to 8, wherein the remaining variables are as described above for Formula I and the first, second, third, fourth, fifth, sixth, seventh, eighth, ninth, tenth, or eleventh embodiment. In another alternative, w in Formula I is an integer from 2 to 4, wherein the remaining variables are as described above for Formula I and the first, second, third, fourth, fifth, sixth, seventh, eighth, ninth, tenth, or eleventh embodiment.

In a thirteenth embodiment, $R^f$ in Formula I is

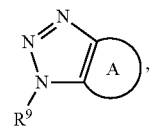

wherein the remaining variables are as described above for Formula I and the first, second, third, fourth, fifth, sixth, seventh, eighth, ninth, tenth, eleventh, or twelfth embodiment.

In a fourteenth embodiment, ring A is

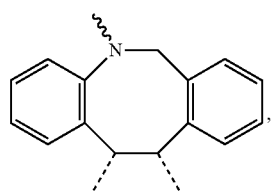

wherein the remaining variables are as described above for Formula I and the first, second, third, fourth, fifth, sixth, seventh, eighth, ninth, tenth, eleventh, twelfth, or thirteenth embodiment.

In a fifteenth embodiment, the fluorophore in Formula I, if present, is fluorescein, wherein the remaining variables are as described above for Formula I and the first, second, third, fourth, fifth, sixth, seventh, eighth, ninth, tenth, eleventh, twelfth, thirteenth, or fourteenth embodiment.

In a sixteenth embodiment, the compound of Formula I is of the Formula II:

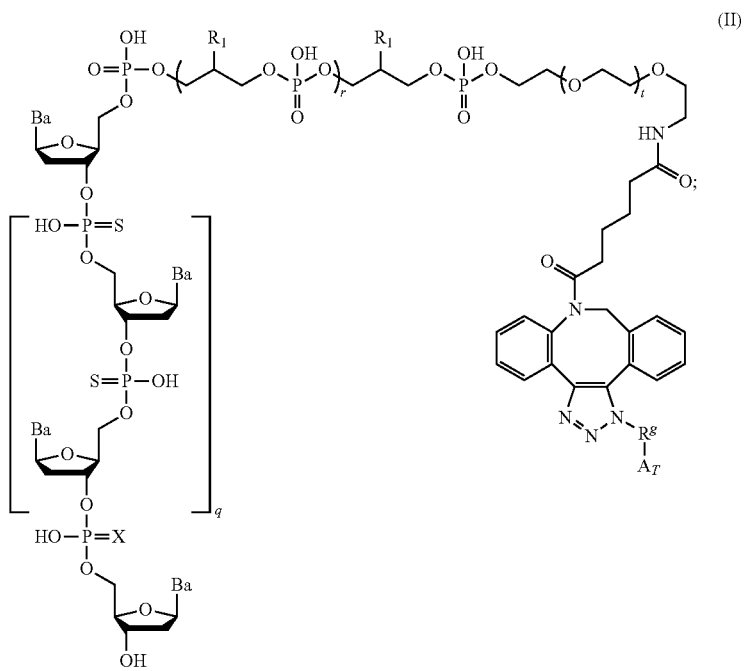

or a pharmaceutically acceptable salt thereof, wherein the remaining variables are as described above for Formula I and the first, second, third, fourth, seventh, eighth, ninth, tenth, eleventh, twelfth, thirteenth, fourteenth, or fifteenth embodiment.

In a seventeenth embodiment, the compound of Formula I is of the Formula IIa:

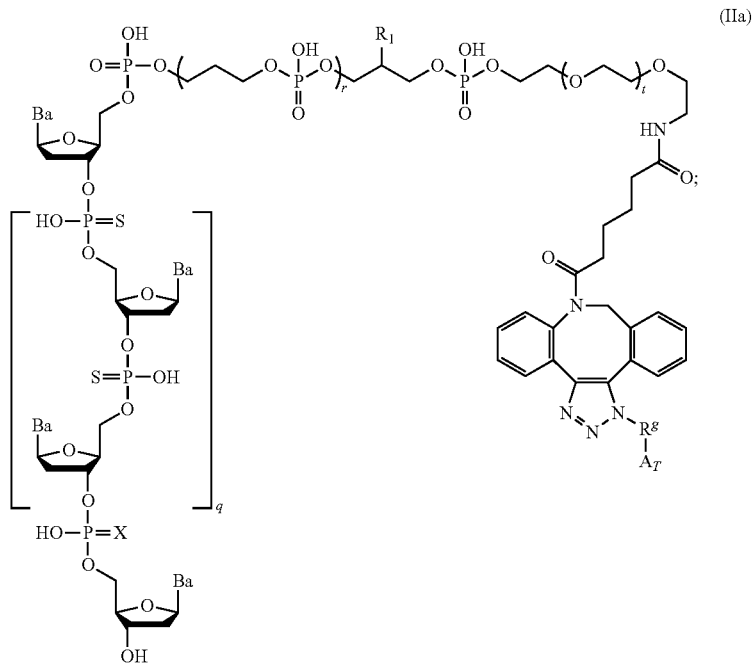

or a pharmaceutically acceptable salt thereof, wherein the remaining variables are as described above for Formula I and the first, second, third, fourth, seventh, eighth, ninth, tenth, eleventh, twelfth, thirteenth, fourteenth, fifteenth, or sixteenth embodiment. Alternatively, the compound of Formula I is of the Formula IIa':

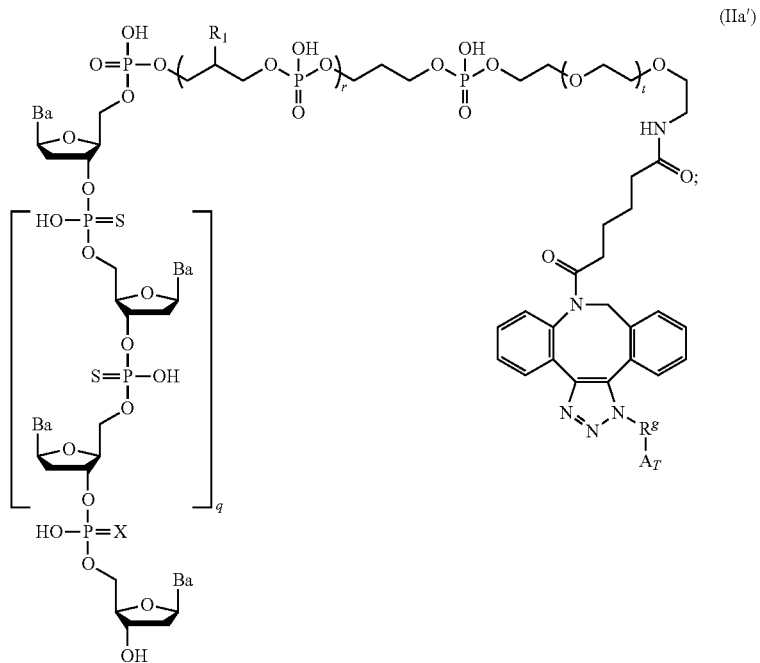

or a pharmaceutically acceptable salt thereof, wherein the remaining variables are as described above for Formula I and the first, second, third, fourth, seventh, eighth, ninth, tenth, eleventh, twelfth, thirteenth, fourteenth, fifteenth, or sixteenth embodiment.

In an eighteenth embodiment, the compound of Formula I is of the Formula IIb:

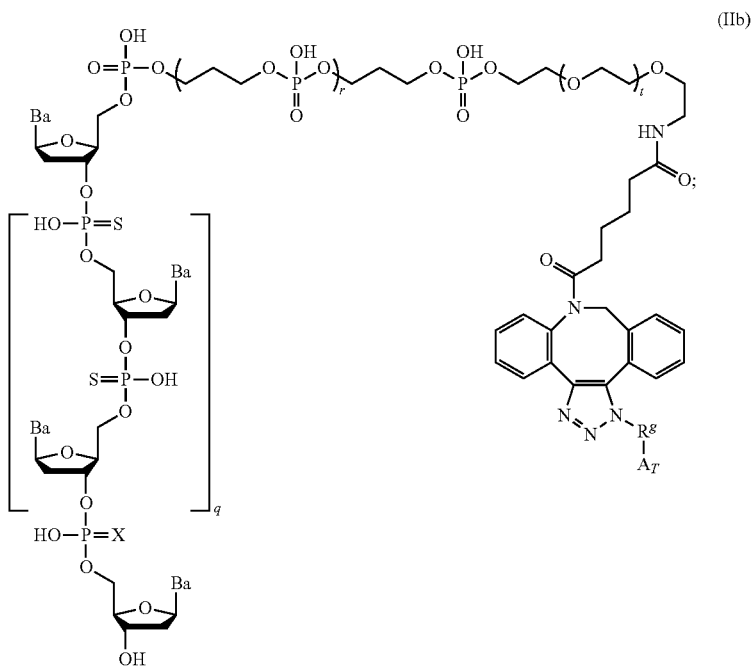

or a pharmaceutically acceptable salt thereof, wherein the remaining variables are as described above for Formula I and the first, second, third, fourth, seventh, eighth, ninth, tenth, eleventh, twelfth, thirteenth, or eighteenth embodiment.

In a nineteenth embodiment, the compound of Formula I is of the Formula III:

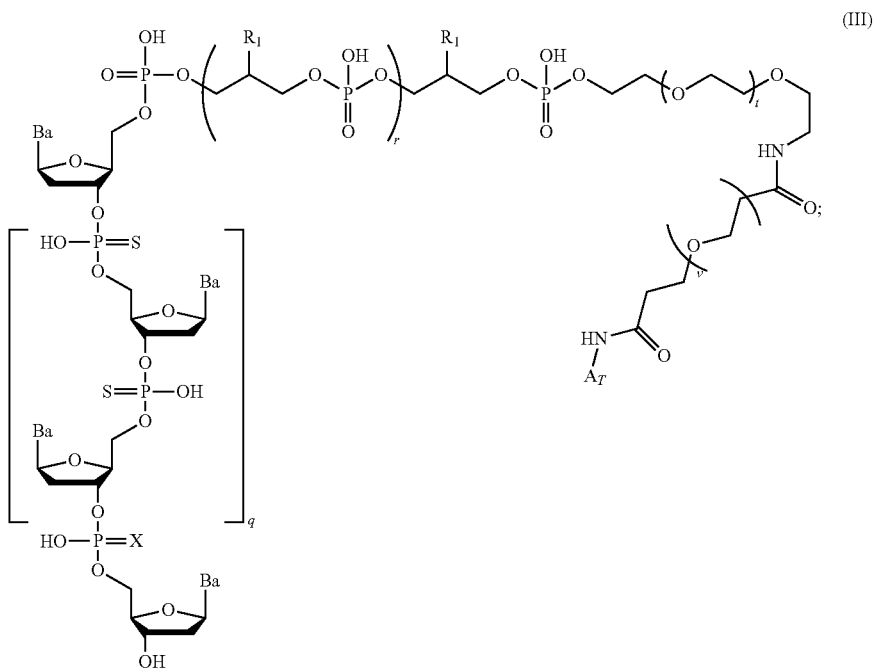

or a pharmaceutically acceptable salt thereof, wherein the remaining variables are as described above for Formula I and the first, second, third, fourth, fifth, eighth, tenth, eleventh, or fifteenth embodiment. Alternatively, the compound of Formula I is of the Formula III':

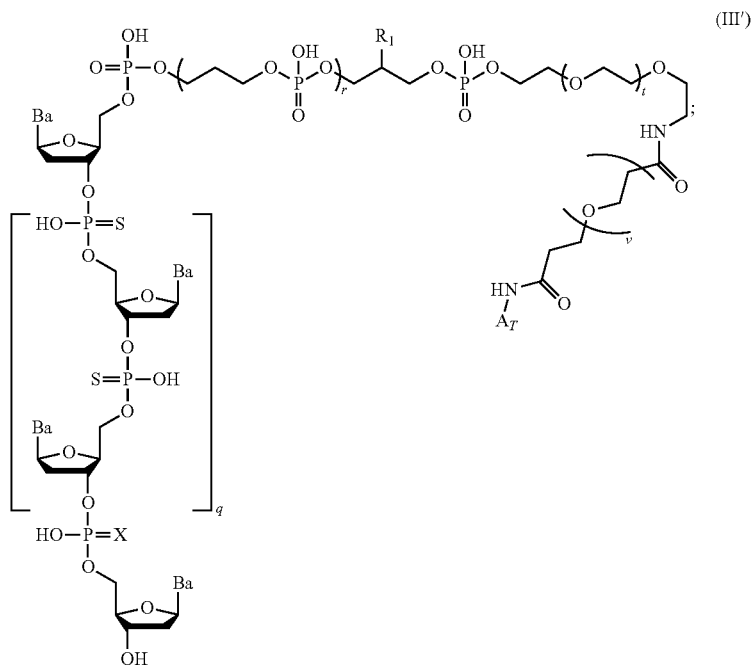
(III')

or a pharmaceutically acceptable salt thereof, wherein the remaining variables are as described above for Formula I and the first, second, third, fourth, fifth, eighth, tenth, eleventh, or fifteenth embodiment. In another alternative, the compound of Formula I is of the Formula IIIa':

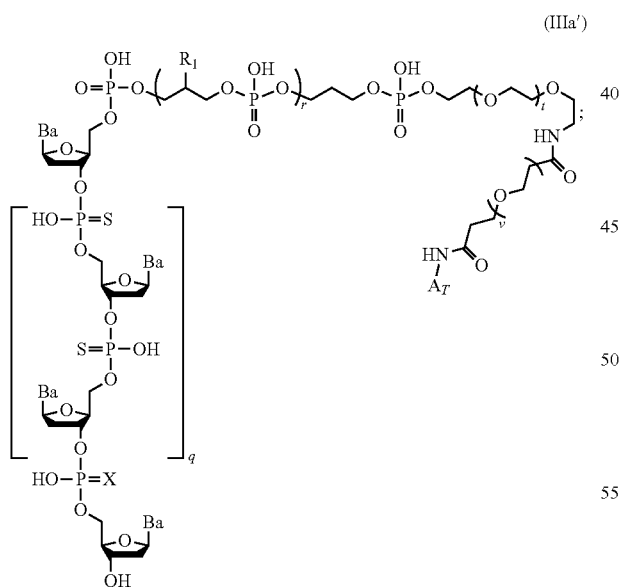
(IIIa')

or a pharmaceutically acceptable salt thereof, wherein the remaining variables are as described above for Formula I and the first, second, third, fourth, fifth, eighth, tenth, eleventh, or fifteenth embodiment.

In a twentieth embodiment, the compound of Formula I is of the Formula IIIa:

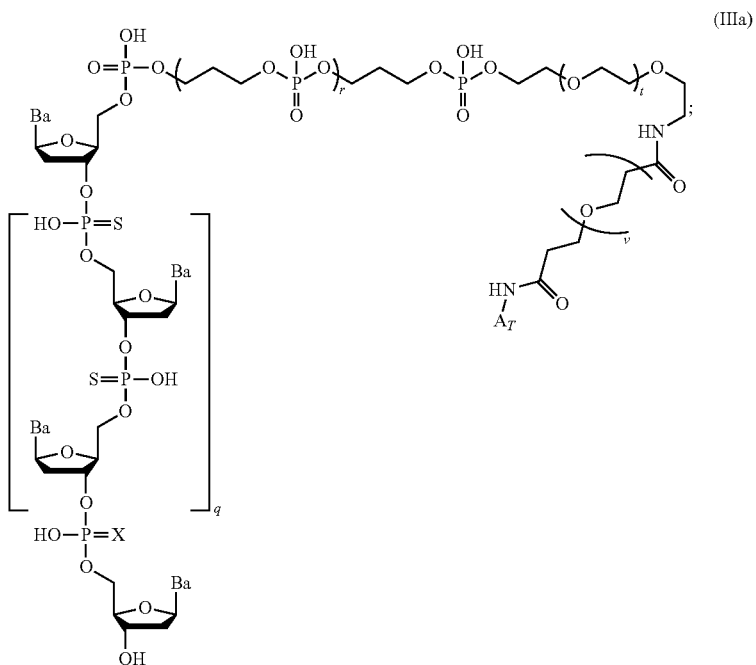

(IIIa)

or a pharmaceutically acceptable salt thereof, wherein the remaining variables are as described above for Formula I and the first, second, third, fourth, fifth, eighth, tenth, eleventh, or nineteenth embodiment.

In a twenty-first embodiment, the compound of Formula I is of the Formula IV:

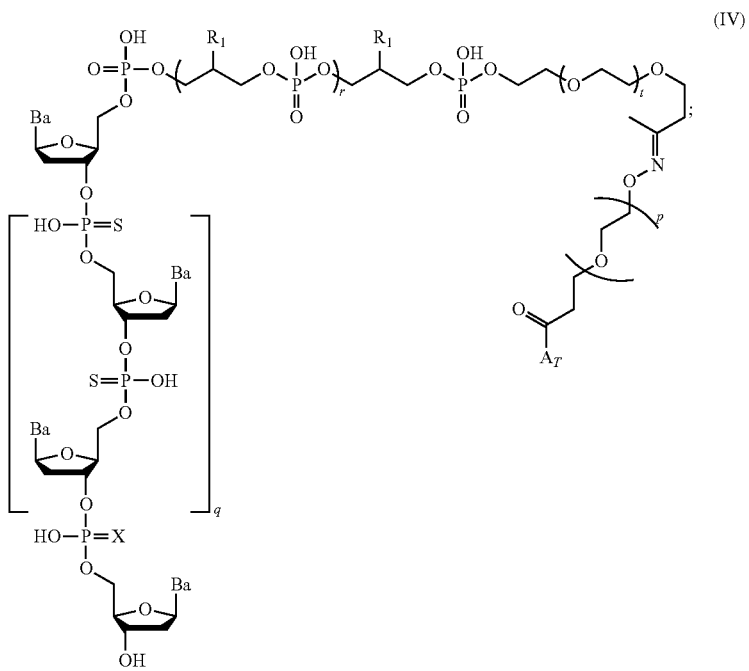

(IV)

or a pharmaceutically acceptable salt thereof, wherein the remaining variables are as described above for Formula I and the first, second, third, fourth, sixth, tenth, eleventh, twelfth, or fifteenth embodiment. Alternatively, the compound of Formula I is of the Formula IV":

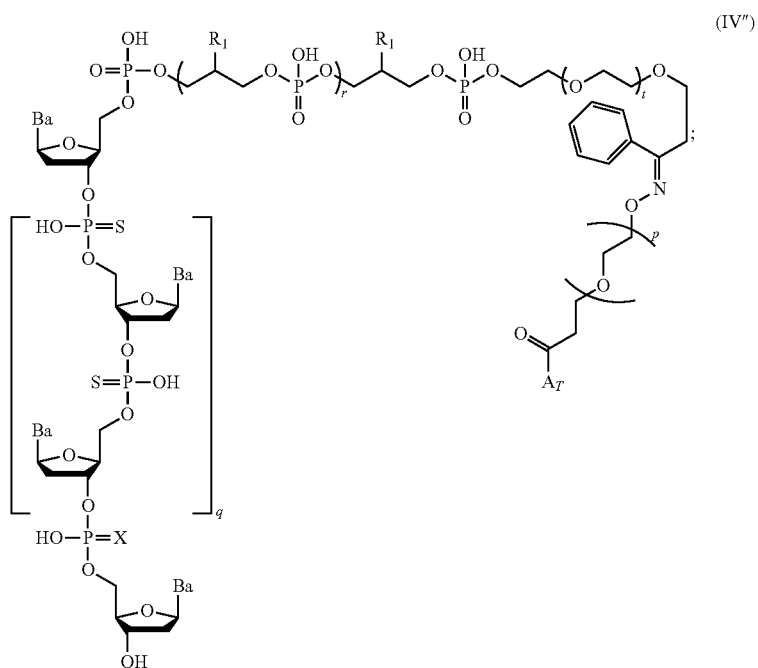

or a pharmaceutically acceptable salt thereof, wherein the remaining variables are as described above for Formula I and the first, second, third, fourth, sixth, tenth, eleventh, twelfth, or fifteenth embodiment. In another alternative, the compound of Formula I is of the Formula IV':

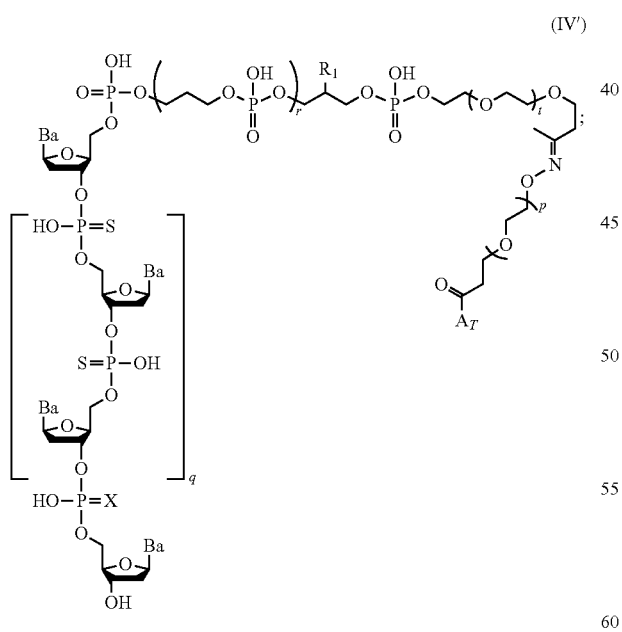

or a pharmaceutically acceptable salt thereof, wherein the remaining variables are as described above for Formula I and the first, second, third, fourth, sixth, tenth, eleventh, twelfth, or fifteenth embodiment. In another alternative, the compound of Formula I is of the Formula IV':

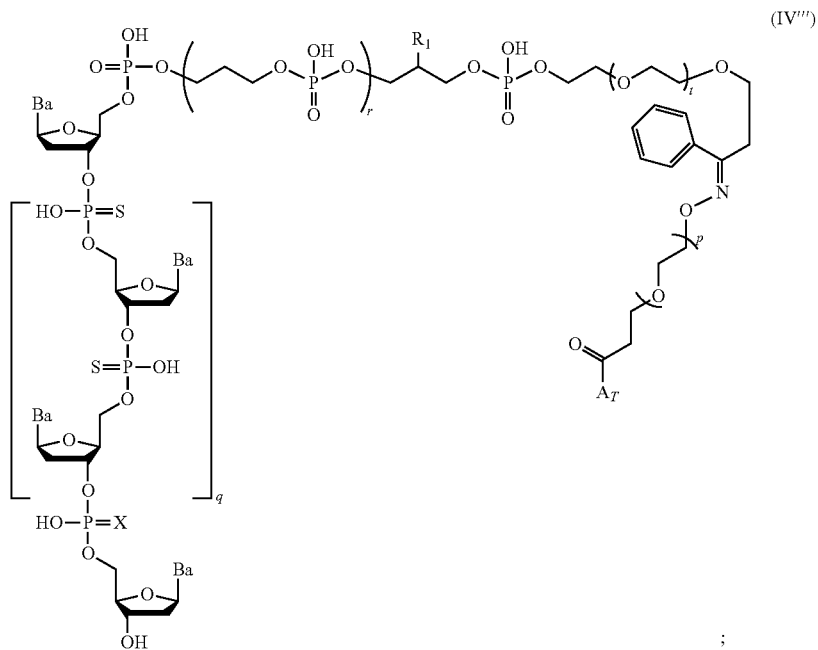

(IV''')

or a pharmaceutically acceptable salt thereof, wherein the remaining variables are as described above for Formula I and the first, second, third, fourth, sixth, tenth, eleventh, twelfth, or fifteenth embodiment. In another alternative, the compound of Formula I is of the Formula IVa':

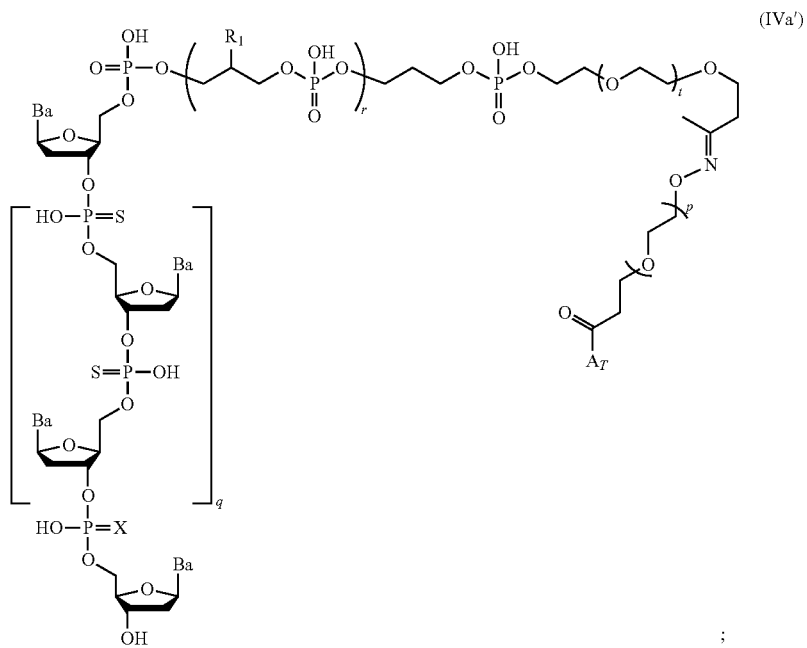

(IVa')

or a pharmaceutically acceptable salt thereof, wherein the remaining variables are as described above for Formula I and the first, second, third, fourth, sixth, tenth, eleventh, twelfth, or fifteenth embodiment. In another alternative, the compound of Formula I is of the Formula IVa':

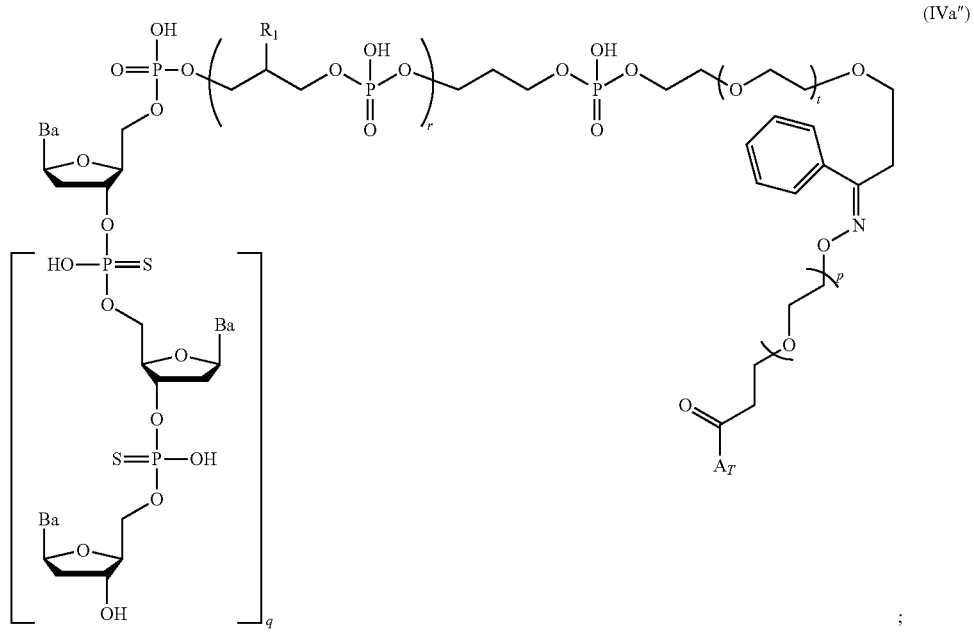

(IVa″)

or a pharmaceutically acceptable salt thereof, wherein the remaining variables are as described above for Formula I and the first, second, third, fourth, sixth, tenth, eleventh, twelfth, or fifteenth embodiment.

In a twenty-second embodiment, the compound of Formula I is of the Formula IVa:

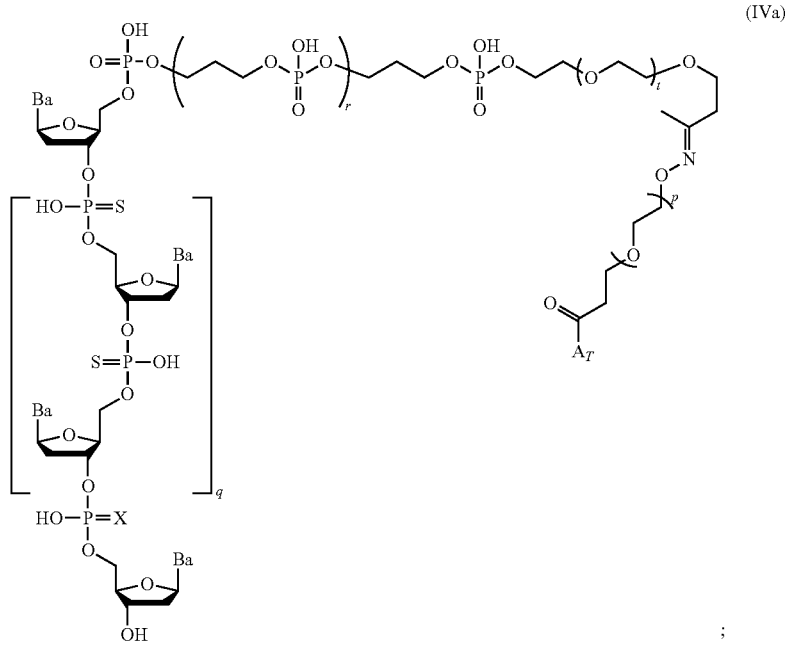

(IVa)

or a pharmaceutically acceptable salt thereof, wherein the remaining variables are as described above for Formula I and the first, second, third, fourth, sixth, tenth, eleventh, twelfth, fifteenth or twenty-first embodiment.

In a twenty-third embodiment, X in Formula I, II, IIa, IIa', IIb, III, III', IIIa, IIIa', IV, IV', IV″, IV‴, IVa', IVa″, and IVa is S, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiment.

In a twenty-fourth embodiment, r in Formula I, II, IIa, IIa', IIb, III, III', IIIa, IIIa', IV, IV', IV″, IV‴, IVa', IVa″, and IVa is an integer from 2 to 6, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiment. Alternatively, r in Formula I, II, IIa, IIa', IIb, III, III', IIIa, IIIa', IV, IV', IV'', IV''', IVa', IVa'', and IVa is an integer from 3 to 5, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiment. In another alternative, r in Formula I, II, IIa, IIa', IIb, III, III', IIIa, IIIa', IV, IV', IV'', IV''', IVa', IVa'', and IVa is 4, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiment.

In a twenty-fifth embodiment, t in Formula I, II, IIa, IIa', IIb, III, III', IIIa, IIIa', IV, IV', IV'', IV''', IVa', IVa'', and IVa is an integer from 1 to 6, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, or twenty-fourth embodiment. Alternatively, t in Formula I, II, IIa, IIa', IIb, III, III', IIIa, IIIa', IV, IV', IV'', IV''', IVa', IVa'', and IVa is an integer from 2 to 4, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, or twenty-fourth embodiment. In another alternative, t in Formula I, II, IIa, IIa', IIb, III, III', IIIa, IIIa', IV, IV', IV'', IV''', IVa', IVa'', and IVa is 3, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, or twenty-fourth embodiment.

In a twenty-sixth embodiment, q in Formula I, II, IIa, IIa', IIb, III, III', IIIa, IIIa', IV, IV', IV'', IV''', IVa', IVa'', and IVa is an integer from 15 to 30, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, or twenty-fifth embodiment. Alternatively, q in Formula I, II, IIa, IIa', IIb, III, III', IIIa, IIIa', IV, IV', IV'', IV''', IVa', IVa'', and IVa is an integer from 15 to 25, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, or twenty-fifth embodiment. In another alternative, q in Formula I, II, IIa, IIa', IIb, III, III', IIIa, IIIa', IV, IV', IV'', IV''', IVa', IVa'', and IVa is 17, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, or twenty-fifth embodiment.

In a twenty-seventh embodiment, the thiophosphate oligonucleotide sequence beginning at the 3' end in Formula I, II, IIa, IIa', IIb, III, III', IIIa, IIIa', IV, IV', IV'', IV''', IVa', IVa'', and IVa is TCCATGAGCTTCCTGATGCT (SEQ ID NO: 5), wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, or twenty-sixth embodiment.

In a twenty-eighth embodiment, $A_T$ in Formula I, II, IIa, IIa', IIb, III, III', IIIa, IIIa', IV, IV', IV'', IV''', IVa', IVa'', and IVa is selected from an isotype class or subclass such as IgG (e.g., IgG1, IgG2, IgG3, IgG4), IgM, IgD, IgA (e.g., IgA1 and IgA2), and IgE antibodies, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, or twenty-seventh embodiment.

In a twenty-ninth embodiment, only one fluorophore is present, if available, on any of the compounds or Formula described herein i.e., if r is 1 or greater than only one $R^1$ is $(C_1-C_6)$alkyl substituted with a fluorophore.

In certain embodiments, the antibody used herein may be specific for an antigen that is intracellular. Intracellular antigens include antigens that are found, for example, in the cytoplasm and/or nucleus of a cell. Examples of an intracellular antigen include, but are not limited to, a receptor (e.g., cytoplasmic receptors such as peroxisome proliferator-activated receptors and nuclear receptors such as steroid hormone receptor, aryl hydrocarbon receptor), a transcription factor (e.g., SP1, AP-1, C/EBP, Heat shock factor, ATF/CREB, c-Myc, 1-Oct, NF-1, STAT3), a cytokine (e.g., interleukins, interferons, erythropoietin, thrombopoietin, colony stimulating factors), a growth factor (EGF, HGF, BMP, VEGF), an enzyme (e.g., protease, kinase, phosphatase), messengers (e.g., hormones such as vasopressin, follicle stimulating hormone, luteinizing hormone or neurotransmitters such as somatostatin or substance P), a member of a signaling pathway (e.g., MAPK pathway, Wnt pathway, Hedgehog pathway, Retinoic acid pathway, TGF beta pathway, JAK-STAT pathway, cAMP-dependent pathway), a carrier protein (e.g., electron carriers, such as oxidoreductases, NADPH oxidases), or a structural protein (e.g., actin, tubulin).

In one embodiment, an intracellular target of the present disclosure is a member of a signal transducer and activator of transcription (STAT) protein family STAT proteins are involved in the development and function of the immune system and play a role in maintaining immune tolerance and tumor surveillance. Examples of intracellular targets from the STAT family include, but are not limited to, STAT1, STAT2, STAT3, STAT4, STAT5 (STAT5A and STAT5B), and STAT6, including homologs thereof.

In another embodiment, an intracellular target of the present disclosure is a member of a vascular endothelial growth factor (VEGF) such as e.g., VEGFR2, cytotoxic T-lymphocyte-associated protein 4 (CTLA4) or hepatocyte growth factor receptor (cMet) protein family. Exemplary VEGF2, CTLA4, and cMet specific antibodies that can be used for $A_T$ in the Formula described herein are disclosed in WO 2013/149219, PCT/US2016/017713, and WO 2013/192594 respectively, each of which are incorporated herein by reference.

In yet another embodiment, and intracellular target of the present disclosure is a member of the RAS gene family such as e.g., KRAS. Exemplary KRAS specific antibodies that can be used for $A_T$ in the Formula described herein are disclosed in U.S. Provisional Application No. 62/407,982, filed Oct. 13, 2016.

In one embodiment, $A_T$ in Formula I, II, IIa, IIa', IIb, III, III', IIIa, IIIa', IV, IV', IV'', IV''', IVa', IVa'', and IVa is an antibody which is specific for STAT3, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth embodiment, or twenty-ninth embodiment. In another embodiment, $A_T$ in Formula I, II, IIa, IIa', IIb, III, III', IIIa, IIIa', IV, IV', IV'', IV''', IVa', IVa'', and IVa is anti-STAT3 antibody comprising a heavy chain variable region comprising an amino acid sequence as set forth in SEQ ID NO: 1 (or a sequence that is at least 95%, 96%, 97%, 98%, or 99% identical to SEQ ID NO: 1) and a light chain variable region comprising an amino acid sequence as set forth in SEQ ID NO: 2 (or a sequence that is at least 95%, 96%, 97%, 98%, or 99% identical to SEQ ID NO: 2), wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth embodiment, or twenty-ninth embodiment. In another embodiment, $A_T$ in Formula I, II, IIa, IIa', IIb, III, III', IIIa, IIIa', IV, IV', IV'', IV''', IVa', IVa'', and IVa is anti-STAT3 antibody comprising a heavy chain variable region comprising an amino acid sequence as set forth in SEQ ID NO: 3 (or a sequence that is at least 95%, 96%, 97%, 98%, or 99% identical to SEQ ID NO: 3) and a light chain variable region comprising an amino acid sequence as set forth in SEQ ID NO: 4 (or a sequence that is at least 95%, 96%, 97%, 98%, or 99% identical to SEQ ID NO: 4), wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth embodiment, or twenty-ninth embodiment.

The amino acid sequences of anti-human STAT3 antibodies ST1A5 and ST3G12 are described below. Both ST1A5 and ST3G12 are human antibodies.

| Antibody | Heavy Chain Variable Domain | Light Chain Variable Domain |
|---|---|---|
| ST1A5 | EVQLVESGAEVKKPGASVKVSCKA SGYTFTGYYMHWVRQAPGQGLEW MGWINPNSGGTNYAQKFQGRVTM TRDTSISTAYMELSRLRSDDTAVYY CARDGGLGWGTYPRLGDAFDIWG QGTMVTVSS (SEQ ID NO: 1) | QSVLTQPPSVSKGLRQTATLTCTGN SNNVGNEGAAWLQQHQGHPPKLL SYRNFNRPSGISERFSASRSGNTASL TITGLQPEDEADYYCSAWDSSLSA WVFGGGTKLTVL (SEQ ID NO: 2) |
| ST3G12 | QVQLVQSGAEVKKPGASVKVSCK ASGYTFTSYYMHWVRQAPGQGLE WMGIINPSGGSTSYAQKFQGRVTM TRDTSTSTVYMELSSLRSEDTAVYY CARSDYVHSFDIWGQGTMVTVSS (SEQ ID NO: 3) | QPVLTQPPSASALLGASIKLTCTLSS EHSTYTVEWYQQRPGRSPQYIMNV KSDGSYNKGDGIPDRFMGSSSGAD RYLTFSNLQSDDEAEYHCGESHRID GQVGVVFGGGTKLTVL (SEQ ID NO: 4) |

4. Description of General Synthetic Processes

Compounds of Formula I can be prepared according to the following general reaction schemes and examples, or modifications thereof. Other methods for preparing compounds described herein will be readily apparent to a person of ordinary skill in the art in light of the following reaction schemes.

In a thirtieth embodiment, a first process for forming a compound having the Formula I:

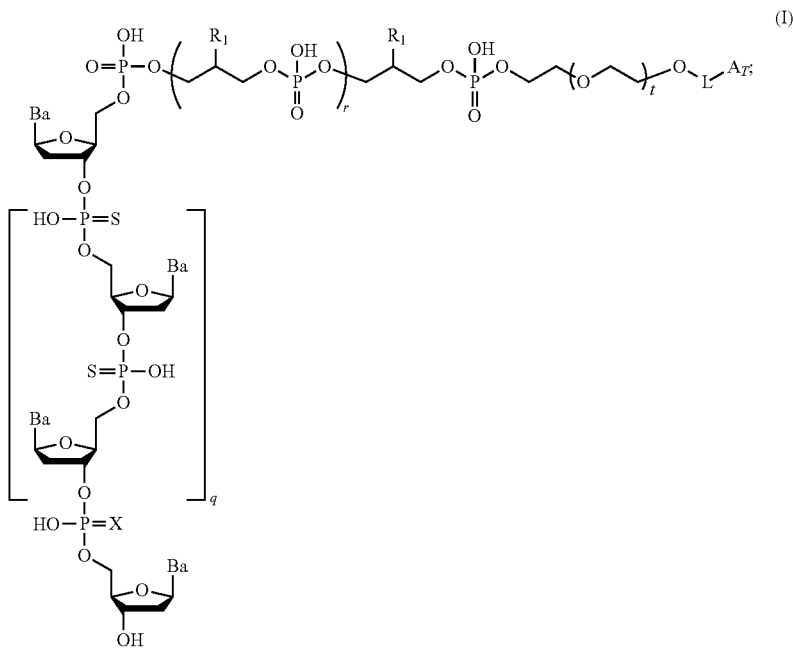

(I)

wherein

L is —CH$_2$—R$^2$—*;

R$^2$ is —(C$_1$-C$_6$)alkyl-NR$^a$C(=O)R$^b$;

R$^a$ is hydrogen or (C$_1$-C$_6$)alkyl;

R$^b$ is (C$_1$-C$_6$)alkyl substituted with R$^f$ or —C(=O)R$^f$;

R$^f$ is

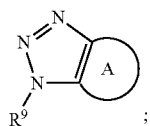

;

ring A is

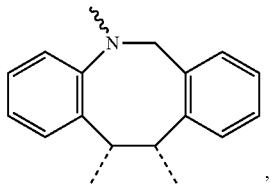

, wherein the dashed bonds indicate the points of attachment to the triazolyl of R$^f$ and the wavy bond indicates the point of attachment to the (C$_1$-C$_6$)alkyl or carbonyl each defined by R$^b$; and R$^g$ is (C$_1$-C$_6$)alkyl or —[(C$_1$-C$_6$)alkyl-O—(C$_1$-C$_6$)alkyl]$_w$C(=O)NH; comprises reacting a compound having the Formula 100:

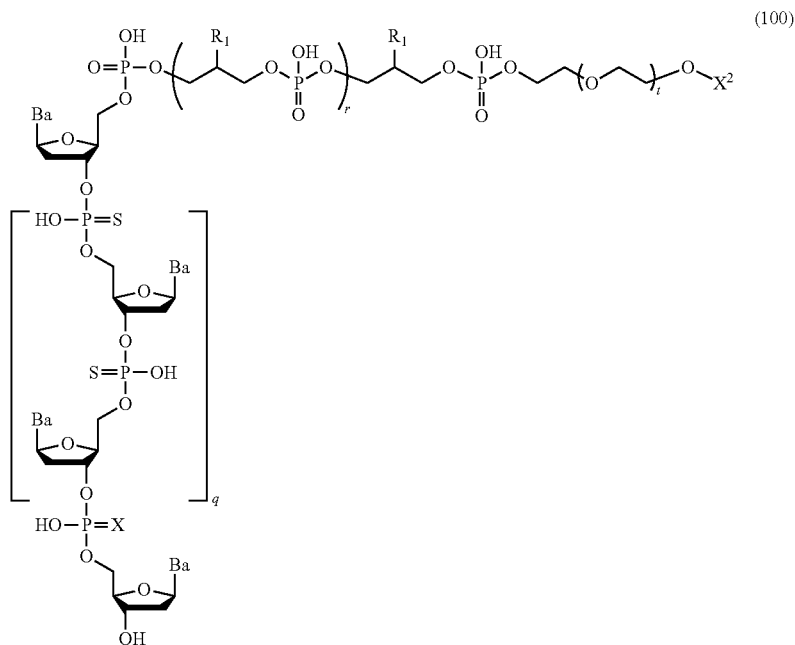

(100)

wherein $X^2$ is —$CH_2(C_1$-$C_6)$alkyl-$NR^aC(=O)R^b$;

$R^a$ is hydrogen or $(C_1$-$C_6)$alkyl;

$R^b$ is $(C_1$-$C_6)$alkyl substituted with $R^{40}$ or —$C(=O)R^{40}$; and $R^{40}$ is

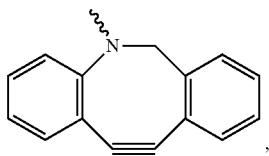

, wherein the wavy line indicates the point of attachment to the $(C_1$-$C_6)$alkyl or carbonyl defined by $R^b$;

with a compound having the Formula $A_T$-Y, wherein Y is —$R^gN_3$; and wherein the remaining variables are as defined above in the first embodiment for Formula I.

In a thirty-first embodiment, $R^a$ in the first process for forming a compound of Formula I is hydrogen; and $R^b$ is $(C_1$-$C_6)$alkyl substituted with —$C(=O)R^f$, wherein the remaining variables are as defined above in the thirtieth embodiment.

In a thirty-second embodiment, $R^g$ in the first process for forming a compound of Formula I is —$[(C_1$-$C_3)$alkyl-O—$(C_1$-$C_3)$alkyl$]_wC(=O)NH$, wherein the remaining variables are as defined above in the first embodiment for Formula I and in the thirtieth or thirty-first embodiment.

In a thirty-third embodiment, w in the first process for forming a compound of Formula I is an integer from 2 to 10, wherein the remaining variables are as defined above in the first embodiment for Formula I and in the thirtieth, thirty-first, or thirty-second embodiment. Alternatively, w in the first process for forming a compound of Formula I is an integer from 2 to 8, wherein the remaining variables are as defined above in the first embodiment for Formula I and in the thirtieth, thirty-first, or thirty-second embodiment. In another alternative, w in the first process for forming a compound of Formula I is an integer from 2 to 4, wherein the remaining variables are as defined above in the first embodiment for Formula I and in the thirtieth, thirty-first, or thirty-second embodiment.

In a thirty-fourth embodiment, compounds having the Formula $A_T$-Y in the first process for forming a compound of Formula I, wherein Y is —$R^gN_3$, can be prepared by treating $A_T$ as defined herein with —$R^4N_3$, where $R^4$ is —$[(C_1$-$C_3)$alkyl-O—$(C_1$-$C_3)$alkyl$]_wC(=O)O$-Lg and Lg is a leaving group such as pentafluorophenyl, tetrafluorophenyl, activated ester (e.g., NHS ester, sulfo-NHS ester), and the like, wherein the remaining variables are as defined above in the first embodiment for Formula I and in the thirtieth, thirty-first, thirty-second, or thirty-third embodiment.

In a thirty-fifth embodiment, a second process for forming a compound having the Formula I:

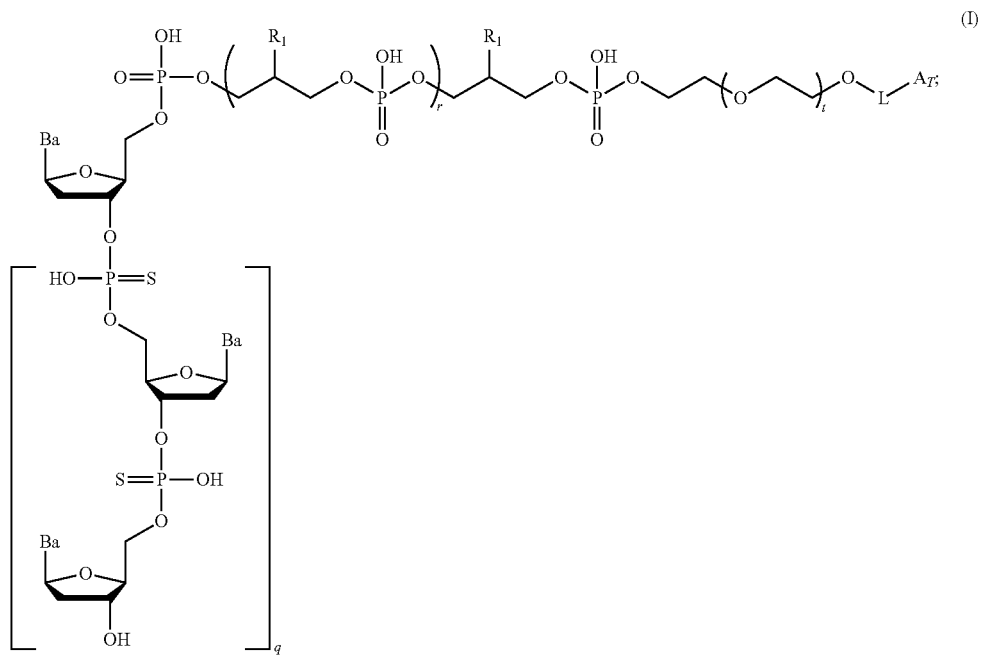

(I)

wherein
L is —CH$_2$—R$^2$—*;
R$^2$ is —(C$_1$-C$_6$)alkyl-NR$^a$C(=O)R$^d$;
R$^d$ is —[(C$_1$-C$_6$)alkyl-O—(C$_1$-C$_6$)alkyl]$_v$C(=O)NH;
R$^a$ is hydrogen or (C$_1$-C$_6$)alkyl;
comprises reacting a compound having the Formula 110:

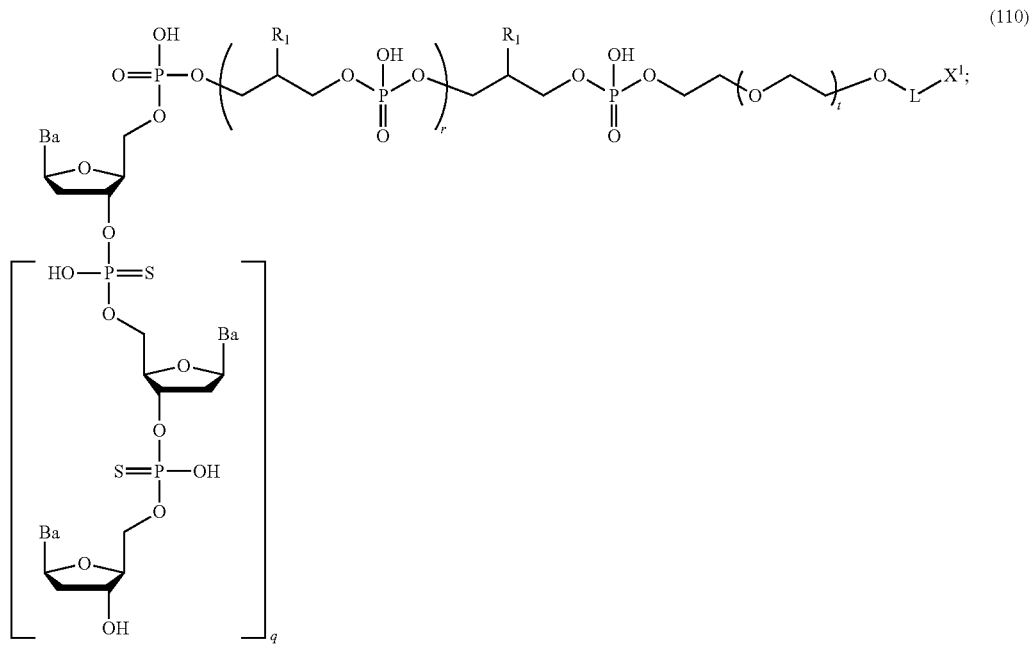

(110)

wherein X$^1$ is —C(O)pentafluorophenyl or —C(O)tetrafluorophenyl; with A$_T$, wherein the remaining variables are as defined above in the first embodiment for Formula I.

Specific examples of compounds are provided in the EXEMPLIFICATION. Pharmaceutically acceptable salts as well as the neutral forms of these compounds are included herein.

5. Uses, Formulation and Administration

Pharmaceutically Acceptable Compositions

In certain embodiments, the present disclosure provides a method of treating a patient (e.g., a human) with a disease or disorder defined herein comprising the step of administering to the patient an effective amount of a compound of Formula I, or a pharmaceutically acceptable salt or composition thereof.

The amount of a provided compound that may be combined with carrier materials to produce a composition in a single dosage form will vary depending upon the patient to be treated and the particular mode of administration.

Compounds or compositions described herein may be administered using any amount and any route of administration effective for treating or lessening the severity of one or more of the diseases and conditions described herein. A specific dosage and treatment regimen for any particular patient will depend upon a variety of factors, including age, body weight, general health, sex, diet, time of administration, rate of excretion, drug combination, the judgment of the treating physician, and the severity of the particular disease being treated.

Uses of Compounds and Pharmaceutically Acceptable Compositions

Compounds and compositions described herein are useful for intracellular delivery of, or to enhance the intracellular delivery of, one or more antibodies. Thus, it will be appreciated that the present disclosure provides a method of treating a disease or disorder that could be treated by an antibody (e.g., $A_T$ in Formula I). Such diseases and disorders include e.g., autoimmune disease, developmental disorder, inflammatory disease, metabolic disorder, cardiovascular disease, liver disease, intestinal disease, infectious disease, endocrine disease, neurological disorder.

In certain embodiments, the compounds and compositions described herein are useful in treating cancer or other neoplastic condition in a subject in need thereof.

Exemplary types of cancer include e.g., adrenal cancer, acinic cell carcinoma, acoustic neuroma, acral lentiginous melanoma, acrospiroma, acute eosinophilic leukemia, acute erythroid leukemia, acute lymphoblastic leukemia (ALL), acute megakaryoblastic leukemia, acute monocytic leukemia, acute promyelocytic leukemia, acute myeloid leukemia (AML) adenocarcinoma, adenoid cystic carcinoma, adenoma, adenomatoid odontogenic tumor, adenosquamous carcinoma, megakaryocytic leukemia, adipose tissue neoplasm, chronic myeloid leukemia (CML), adrenocortical carcinoma, chronic myelomonocytic leukemia (CMML), adult T-cell leukemia/lymphoma, juvenile myelomonocytic leukemia (JMML), aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, large granular lymphocyte leukemia, angiomyolipoma, angiosarcoma, astrocytoma, atypical teratoid rhabdoid tumor, B-cell chronic lymphocytic leukemia (CLL), B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In one embodiment, the cancer is pancreatic cancer. In another embodiment, the cancer is lung cancer, such as e.g., small cell lung cancer. In another embodiment, In one embodiment, the compounds and compositions described herein are useful in treating solid tumors. In some aspects, the cancer treated by the compounds or compositions described herein is selected from melanoma, glioma, medulloblastoma, renal cell carcinoma, pancreatic adenocarcinoma, ovarian carcinoma, rhabdomyosarcoma, osteosarcoma, glioblastoma, breast, pancreas, ovarian, prostate, lung, liver, colon, colorectal, gastric, head, neck, and kidney. In one embodiment, the cancer is a hematological cancer. In yet another embodiment, the hematological cancer is selected from AML, ALL, CML, CLL, hairy cell leukemia, CMML, JMML, megakaryocytic leukemia, and large granular lymphocyte leukemia.

In one embodiment, when $A_T$ in the compounds or compositions described herein is anti-KRAS (e.g., compound 910, 911, 912, and 913), the cancer is a cancer having a KRAS mutation. In one aspect, the KRAS mutation is a G12D mutation. In another embodiment, when $A_T$ in the compounds or compositions described herein is anti-KRAS (e.g., compound 910, 911, 912, and 913), the cancer is selected from pancreatic cancer, lung cancer, including non-small cell lung cancer, colorectal cancer, prostate cancer, breast cancer, ovarian cancer, head and neck cancer, bladder cancer, melanoma, colorectal cancer, leiomyoma, leiomyosarcoma, glioma, glioblastoma, esophageal cancer, liver cancer, kidney cancer, stomach cancer, colon cancer, cervical cancer, uterine cancer, liver cancer and a hematological cancer. In another embodiment, when $A_T$ in the compounds or compositions described herein is anti-KRAS (e.g., compound 910, 911, 912, and 913), the cancer is pancreatic cancer. In another embodiment, when $A_T$ in the compounds or compositions described herein is anti-KRAS (e.g., compound 910, 911, 912, and 913), the cancer is lung cancer. In one aspect, the lung cancer is non small cell lung cancer. In another embodiment, when $A_T$ in the compounds or compositions described herein is anti-KRAS (e.g., compound 903), the cancer is colorectal cancer. In another embodiment, when $A_T$ in the compounds or compositions described herein is anti-KRAS (e.g., compound 910, 911, 912, and 913), the cancer is a precursor lesion. In another embodiment, when $A_T$ in the compounds or compositions described herein is anti-KRAS (e.g., compound 910, 911, 912, and 913), the cancer is metastatic.

In one embodiment, when $A_T$ in the compounds or compositions described herein is anti-STAT3 (e.g., ST1A5, ST3G12, ST5G12 as in compounds 900, 900a, 901, 901a, 902, 902a, 903, 903a, 904, 904a, 905, and 905a), the cancer is a cancer with constitutive STAT3 activity. In one embodiment, when $A_T$ in the compounds or compositions described herein is anti-STAT3 (e.g., ST1A5, ST3G12, ST5G12 as in compounds 900, 900a, 901, 901a, 902, 902a, 903, 903a, 904, 904a, 905, and 905a), the cancer is a solid tumor. In another embodiment, when $A_T$ in the compounds or compositions described herein is anti-STAT3 (e.g., ST1A5, ST3G12, ST5G12 as in compounds 900, 900a, 901, 901a, 902, 902a, 903, 903a, 904, 904a, 905, and 905a), the cancer is selected from melanoma, glioma, medulloblastoma, renal cell carcinoma, pancreatic adenocarcinoma, ovarian carcinoma, rhabdomyosarcoma, osteosarcoma, glioblastoma, breast, pancreas, ovarian, prostate, lung, liver, colon, colorectal, gastric, head, neck, and kidney. In another embodiment, when $A_T$ in the compounds or compositions described herein is anti-STAT3 (e.g., ST1A5, ST3G12, ST5G12 as in compounds 900, 900a, 901, 901a, 902, 902a, 903, 903a, 904, 904a, 905, and 905a), the cancer is a hematological cancer. In another embodiment, when $A_T$ in the compounds or compositions described herein is anti-STAT3 (e.g., ST1A5, ST3G12, ST5G12 as in compounds 900, 900a, 901, 901a, 902, 902a, 903, 903a, 904, 904a, 905, and 905a), the cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), megakaryocytic leukemia, and large granular lymphocyte leukemia. In another embodiment, when $A_T$ in the compounds or compositions described herein is anti-STAT3 (e.g., ST1A5, ST3G12, ST5G12 as in compounds 900, 900a, 901, 901a, 902, 902a, 903, 903a, 904, 904a, 905, and 905a), the cancer is a precursor lesion. In another embodiment, when $A_T$ in the compounds or compositions described herein is anti-STAT3 (e.g., ST1A5, ST3G12, ST5G12 as in compounds 900, 900a, 901, 901a, 902, 902a, 903, 903a, 904, 904a, 905, and 905a), the cancer is metastatic.

EXEMPLIFICATION

As depicted in the Examples below, in certain exemplary embodiments, compounds are prepared according to the following general procedures. It will be appreciated that, although the general methods depict the synthesis of certain compounds herein, the following general methods, and other methods known to one of ordinary skill in the art, can be applied to all compounds described herein.

General Description of Synthetic Methods

Non-Linear Conjugation Approach

To 1.0 mL of antibody ($A_T$) solution (concentration 4-8 mg/mL in PBS, pH 7.4) in an eppendurf tube is added excess (e.g., 5.0 equivalents) of compound 200, wherein $(F)_4$ or $_5$ represents 4 of 5 fluorine atoms, in organic solvent such as DMSO. See Scheme 1 below. The final organic solvent (e.g., DMSO) content in the final mixture was about 6% (v/v). The tube is placed on a rotating wheel and rotated at 4° C. for about 8 hours. The mixture is transferred to a 15 mL centrifugal filter (75K cutoff) and washed with PBS about 3-5 times to afford compounds 250 and 251.

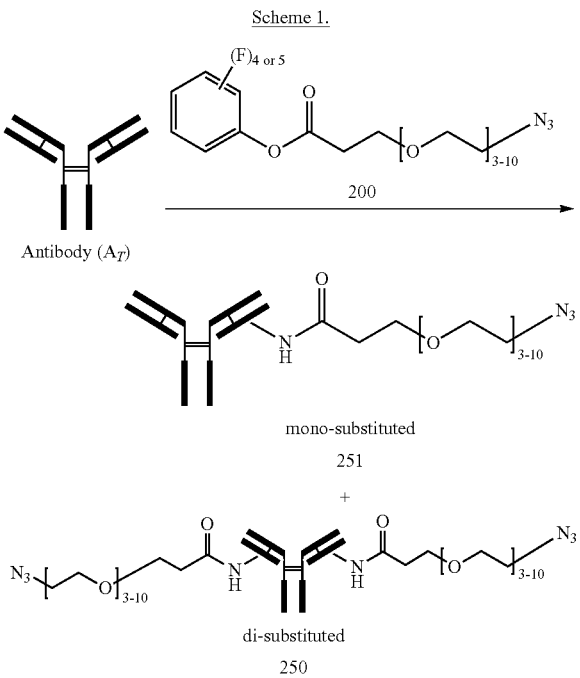

Scheme 1.

To 1.0 mL of a mixture of compound 250 and 251 (concentration 2-8 mg/ml in PBS, pH 7.4) in an eppendurf tube is added excess (e.g., 5.0 equivalents) of compound 300 in PBS. Variables Ba, q, $R^1$, r, and L are as defined above for Formula I, except $R^{fa}$ replaces variable $R^f$ and is an optionally substituted alkyne. The tube is put on a rotating wheel and rotated at room temperature for 8-10 hours. See Scheme 2 below. A second batch of excess (e.g., 5.0 equivalents) of compound 300 is added and mixed for another 8 hours. After reaction, the mixture is transferred to a 15 mL centrifugal filter (75K cutoff) and washed with PBS for one time. The products, compounds 350 and 351 are purified on a Protein-A column to remove unreacted material using a chromatography system. The sample is optionally further purified.

In an alternative, in instances where $R^{fa}$ replaces variable $R^f$ and is an optionally substituted alkyne, to 1.0 mL of a mixture of compounds 250 and 251 (concentration 2-8 mg/ml in 100 mM potassium phosphate, pH 7.0) in an eppendurf tube is added excess (e.g., 5.0 equivalents) of compound 300 in the potassium phosphate buffer, followed by addition of a premixed solution of 2.5 µL of $CuSO_4$ (0.10 mM)+5.0 µL of 0.50 mM THPTA (tris(3-hydroxypropyltriazolyl-methyl)amine) in the phosphate buffer, 25 µL of aminoguanidine (5 mM in the phosphate buffer), and 25 µL of sodium ascorbate (5 mM in the phosphate buffer). The tube is put on a rotating wheel and rotated at room temperature for 3-5 hours. See Scheme 2 below. After reaction, the mixture is transferred to a 15 mL centrifugal filter (75K cutoff) and washed with PBS for two times. The copper ions are further removed by dialysis with solutions of buffed EDTA (ethylenediamine tetraacetic acid). The products, compounds 350 and 351 are purified on a Protein-A column to remove unreacted material using a chromatography system. The sample is optionally further purified. The hashed line ($\sim\!\!\sim$) represents the point of attachment for the other symmetrical half of compound 350 (not shown for clarity) from the reaction of 300 with 250.

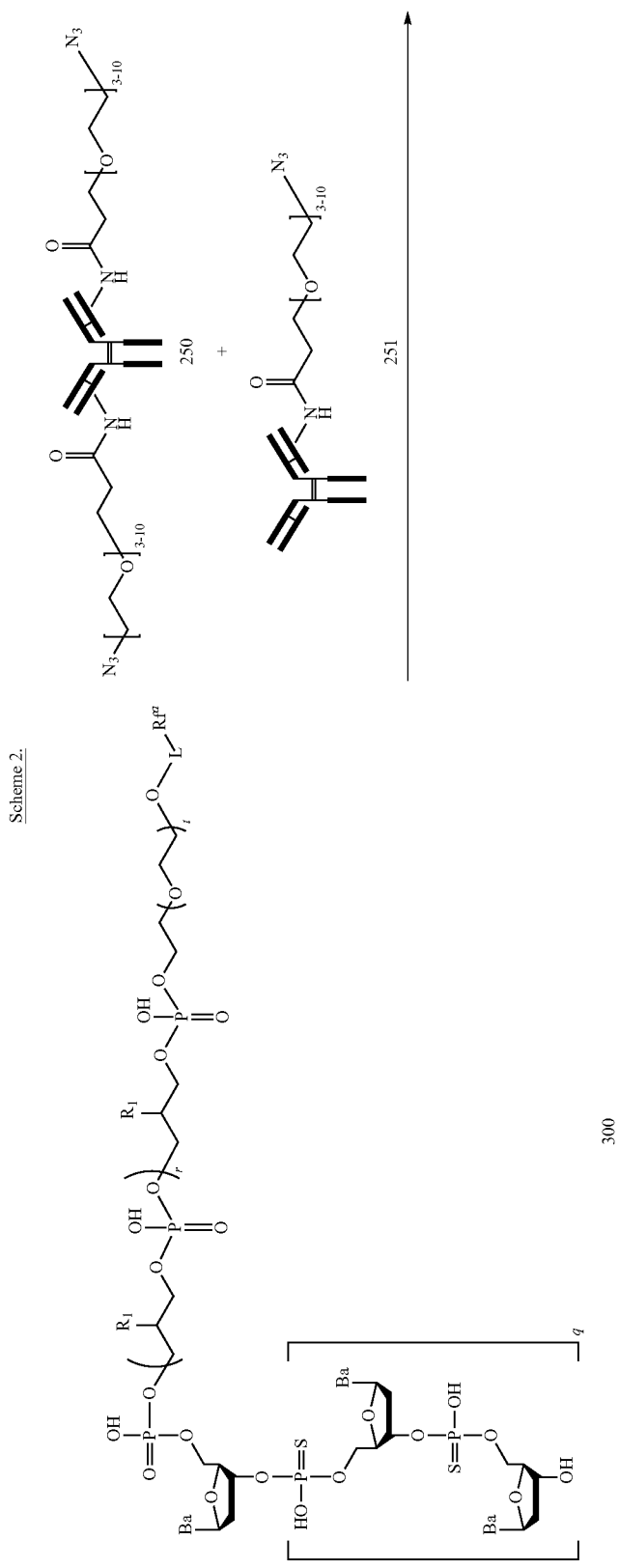

-continued
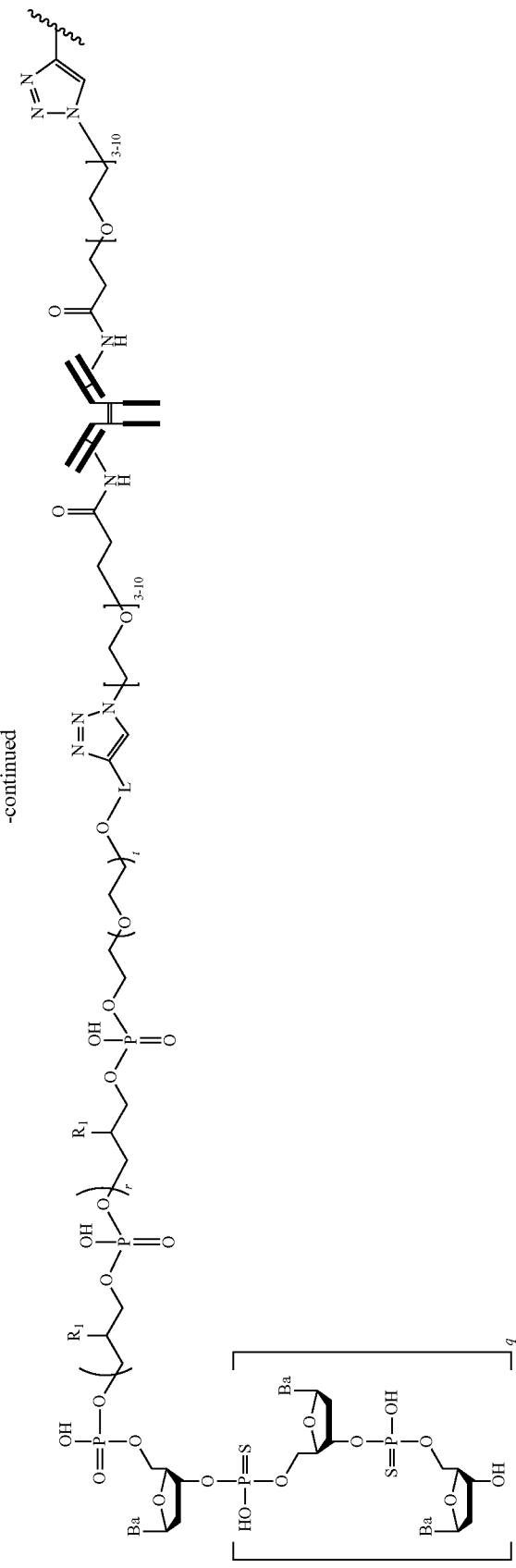
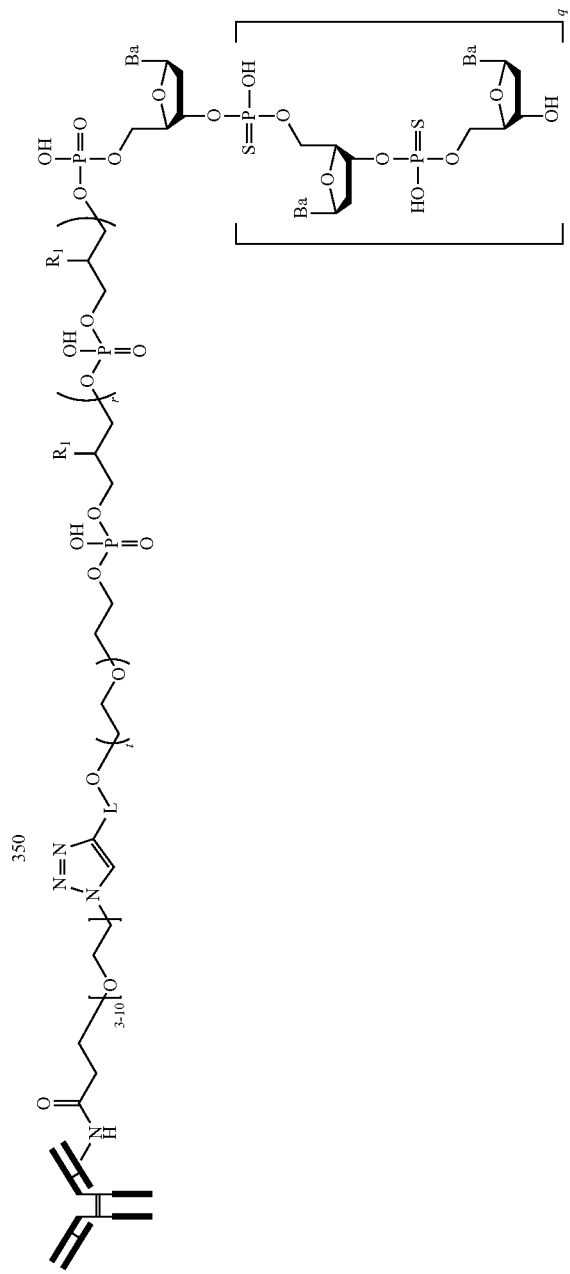
350
351

Linear Conjugation Approach

To 1.0 mL of a solution of compound 400 (concentration 4-8 mg/mL in PBS, pH 7.0) in an eppendurf tube is added excess (e.g., 10.0 equivalents) of compound 450 in an organic solvent (e.g., DMSO). See Scheme 3 below. Ba, q, $R^1$, r, and T are as defined above for Formula I and $(F)_4$ or $_5$ represents 4 of 5 fluorine atoms. The organic solvent (e.g., DMSO) content in the final mixture was about 6% (v/v). The tube is put on a rotating wheel and rotated at room temperature for 2-3 hours. The reaction is monitored by LC/MS. After the reaction is complete, the product is purified by HPLC/LC-MS. After purification, the product, compound 500, is optionally buffer-exchanged to PBS (pH 7.4).

To 1.0 mL of antibody ($A_T$) solution (concentration 4-8 mg/mL in PBS, pH7.4) in an eppendurf tube is added excess (e.g., 3.0 equivalents) of compound 500 in PBS. See Scheme 4 below. The tube is put on a rotating wheel and rotated at room temperature for 4 hours. Then another excess (e.g., 3.0 equivalents) of compound 500 is added and mixed for 6 hours. The mixture is transferred to a 15 mL centrifugal filter (75K cutoff) and washed with PBS for 2 times. The conjugate is further purified on a column to afford the products, compounds 550 and 551. The hashed line (~~~) represents the point of attachment for the other symmetrical half of compound 551 (not shown for clarity).

Scheme 3.

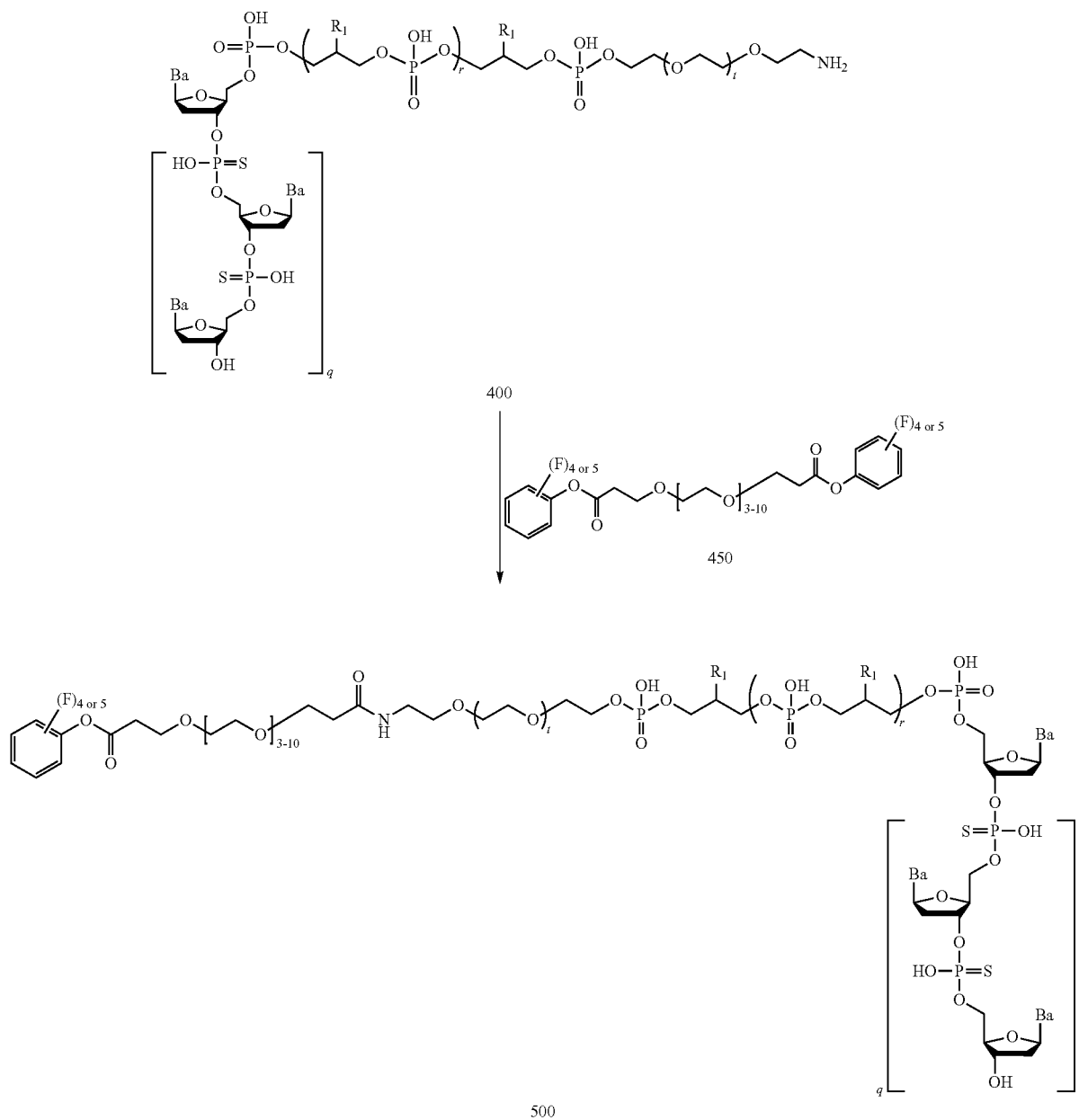

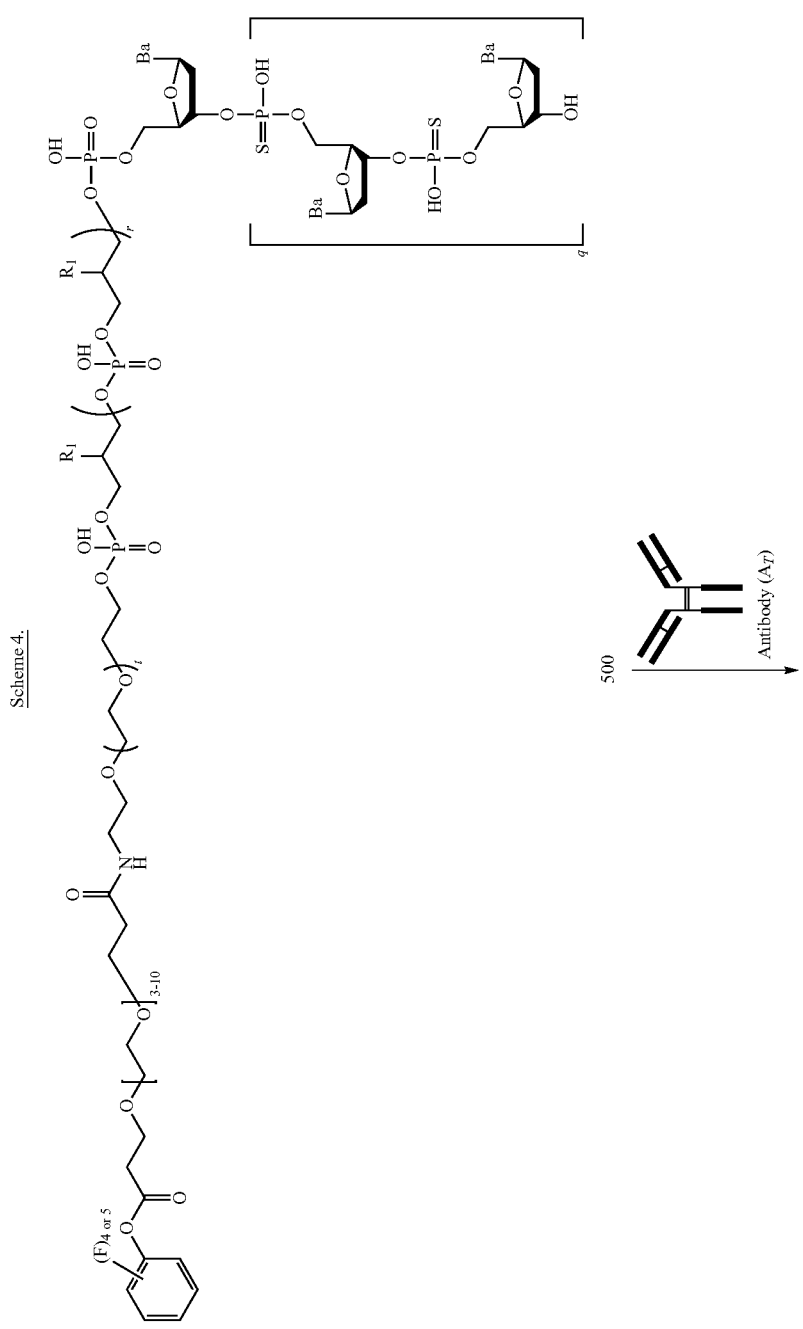

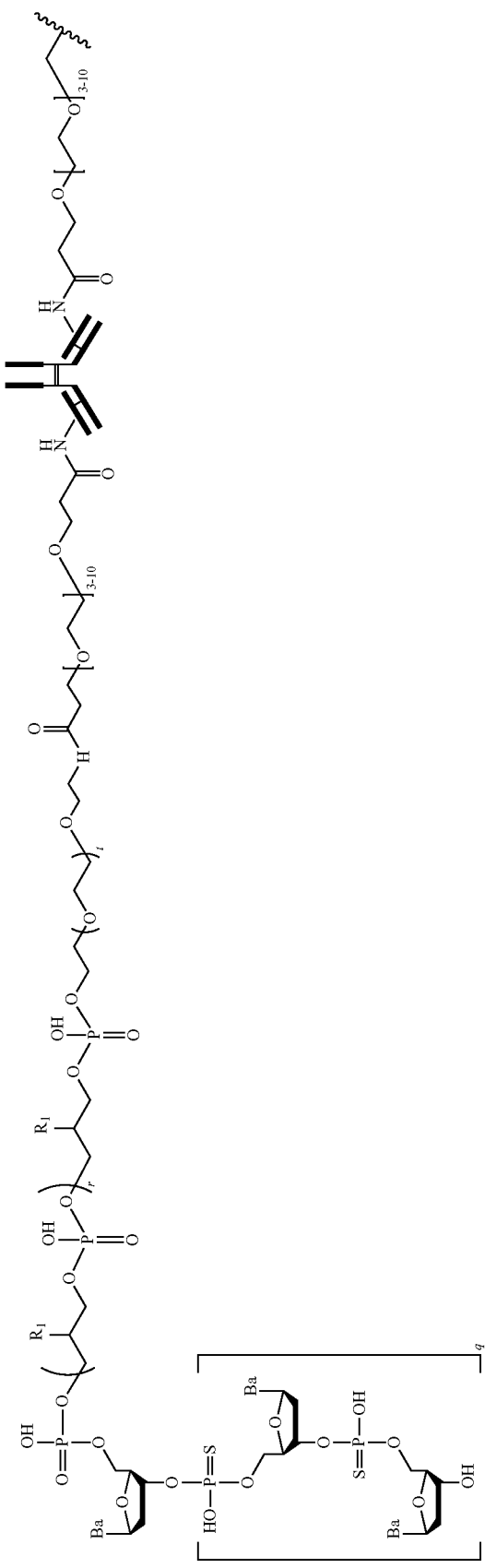

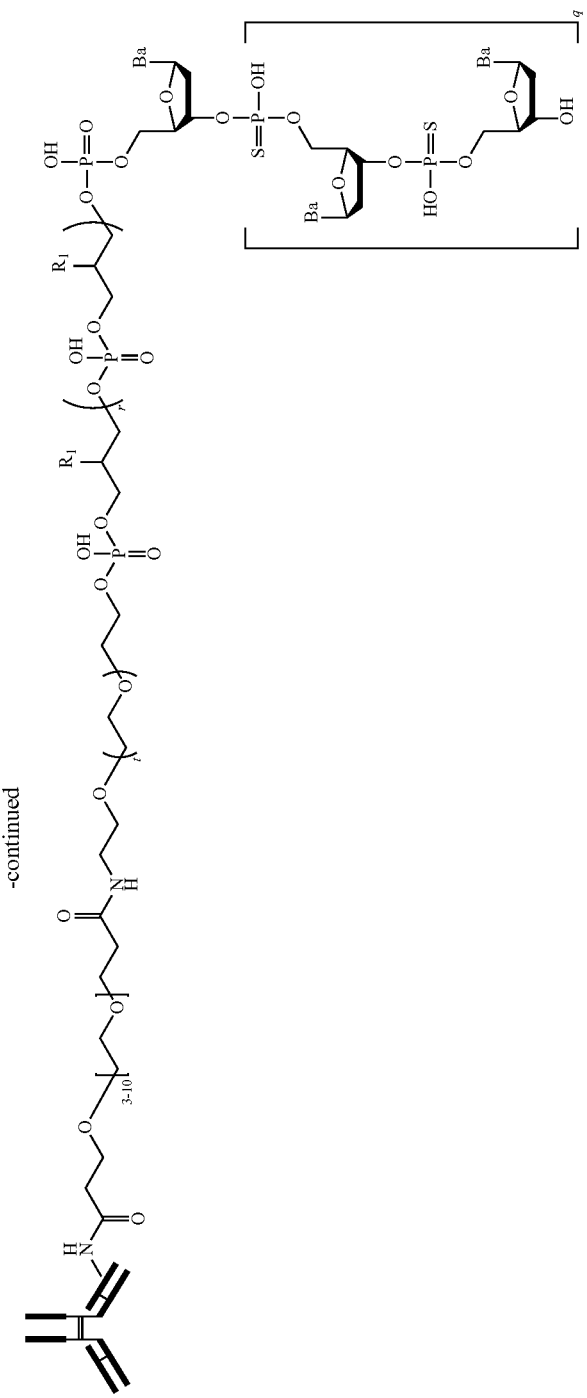

Preparation of Compounds of Formula I

VEGFR2 Antibody Conjugate

To 1.0 mL of VEGFR2 antibody solution (concentration 4-8 mg/mL in PBS, pH7.4) in an eppendurf tube was added 5.0 equivalents of compound 600 (BP-21862, BroadPharm, San Diego, Calif.) in DMSO. See Scheme 5 below. The DMSO content in the final mixture was about 6% (v/v). The tube was put on a rotating wheel and rotated at 4° C. for 8 hours. The mixture was transferred to a 15 mL centrifugal filter (75K cutoff) and washed with PBS for 3-5 times to afford the products, compound 650 and 651.

Scheme 5.

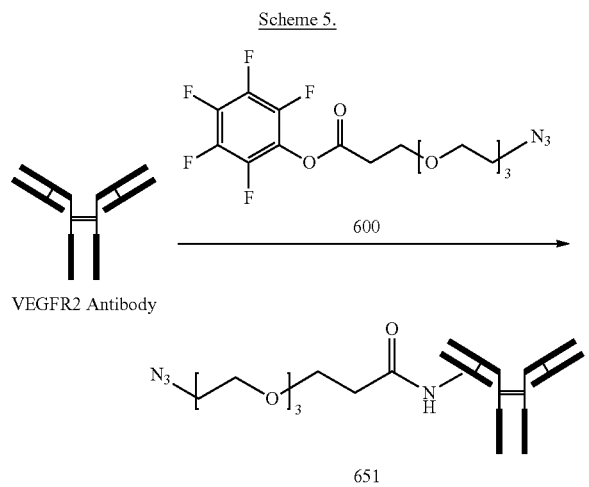

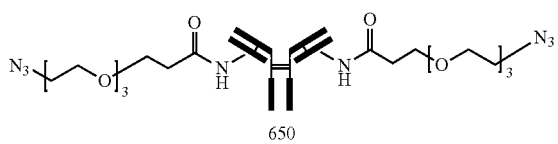

To 1.0 mL of compound 650 and 651 solution (concentration 2-8 mg/ml in PBS, pH 7.4) in an eppendurf tube was added 5.0 equivalents of compound 700 (made by solid-phase synthesis, Trilink Inc, San Diego, Calif.) in PBS. The tube was put on a rotating wheel and rotated at room temperature for 8-10 hours. A second batch of 5.0 equivalents compound 700 was added and mixed for another 8 hours. The mixture was transferred to a 15 mL centrifugal filter (75K cutoff) and washed with PBS for one time. The products 750 and 751 were purified on a Protein-A column using Akta pure chromatography system to remove extra oligos. The product compounds 750 and 751 were further purified on a GE HiTrap Butyl HP column using Akta pure chromatography system to remove unmodified antibody. The hashed line ( ~~~ ) represents the point of attachment for the other symmetrical half of the compound 750, not shown for clarity.

Scheme 6 ("TCCATGAGCTTCCTGATGCT" disclosed as SEQ ID NO: 5).

Scheme 6.

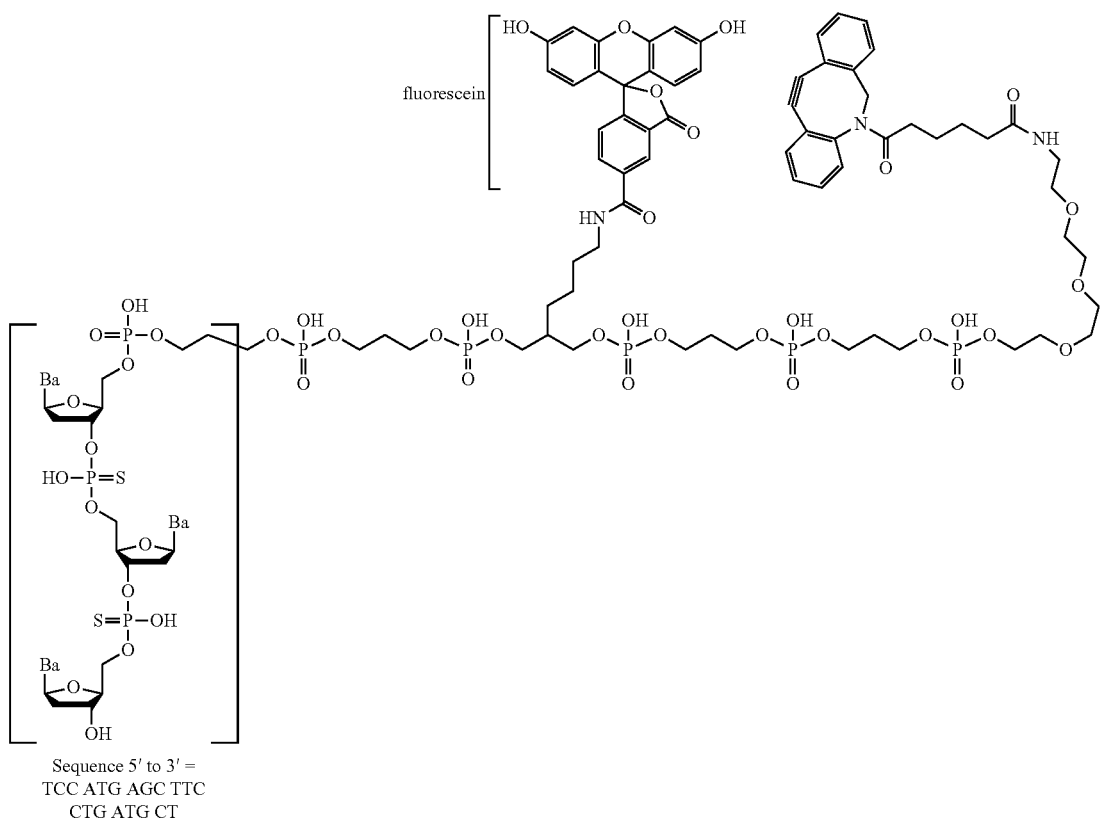

Sequence 5' to 3' =
TCC ATG AGC TTC
CTG ATG CT

700

-continued
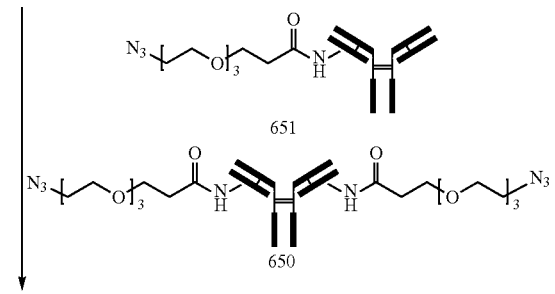
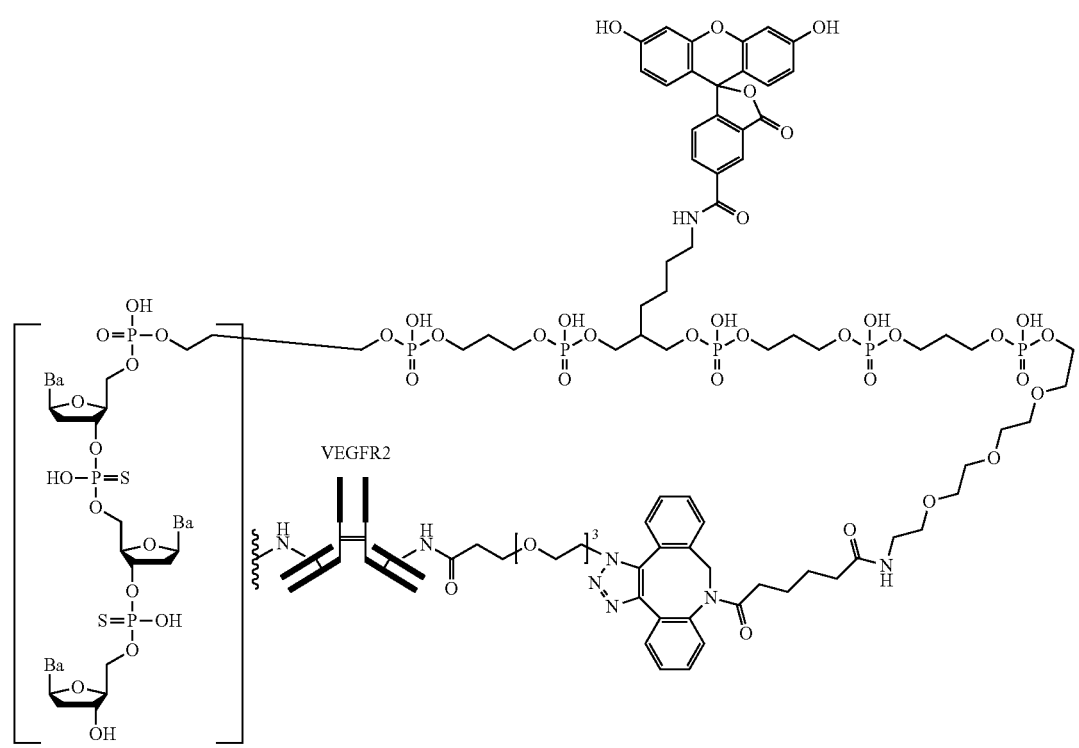

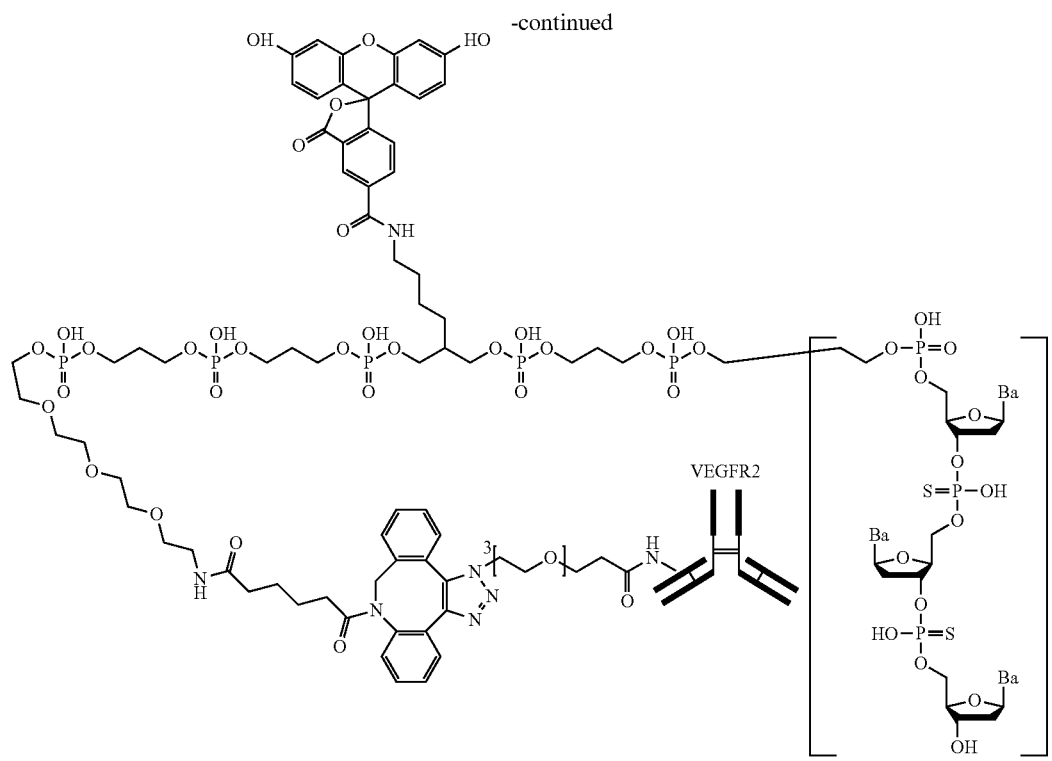

751

Figure 2:
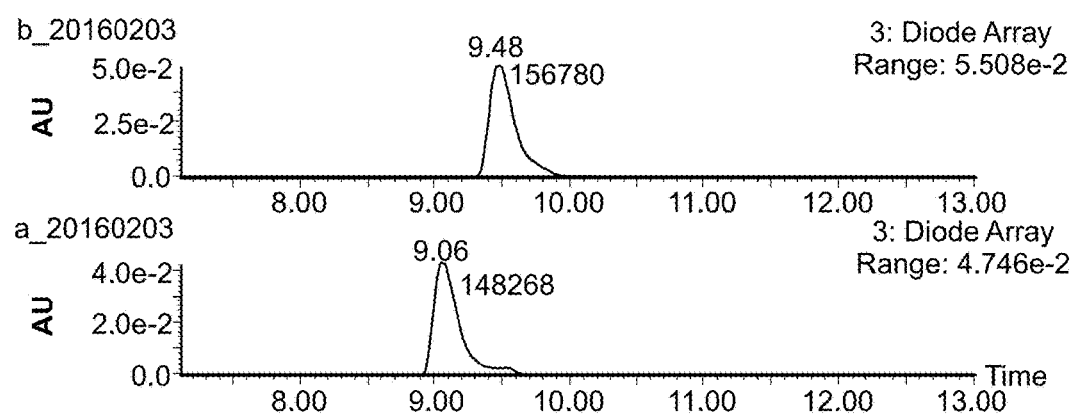
FIG. 2 shows the mass spectrometry data for compound 752, a compound of Formula I where $A_T$ is anti-VEGFR2 IgG.

Non-fluorescein versions of 750 (compound 752) and 751 (compound 753), respectively were also prepared, i.e., where $R^1$ is hydrogen. Compound 752 was characterized via SDS-PAGE and Mass spectrometry as shown in FIGS. 1 and 2 respectively.

Panitumumab Antibody Conjugate

Following the procedure set forth above, compounds 800 and 801 were also prepared, except panitumumab was used as the antibody ($A_T$). The hashed line ( ~~~ ) represents the point of attachment for the other symmetrical half of the compound 800, not shown for clarity. Non-fluorescein versions of 800 and 801 were also prepared, i.e., where $R^1$ is hydrogen ("TCCATGAGCTTCCTGATGCT" disclosed as SEQ ID NO: 5).

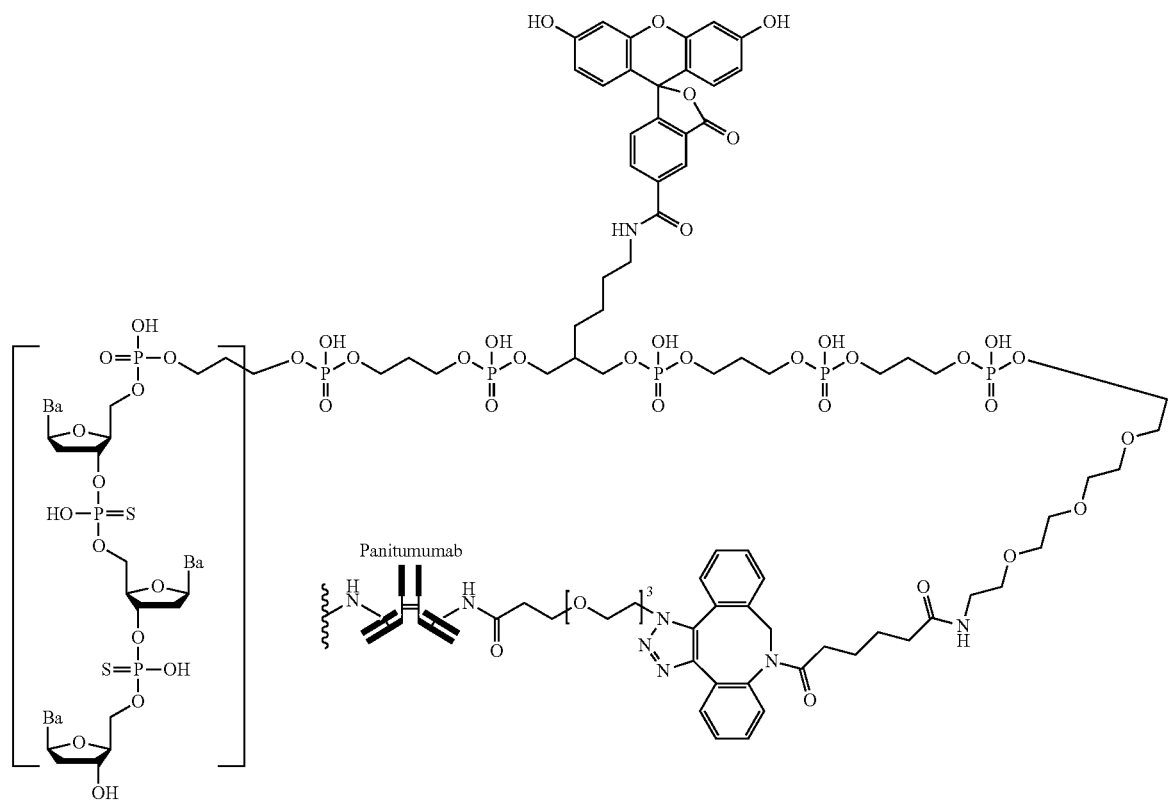

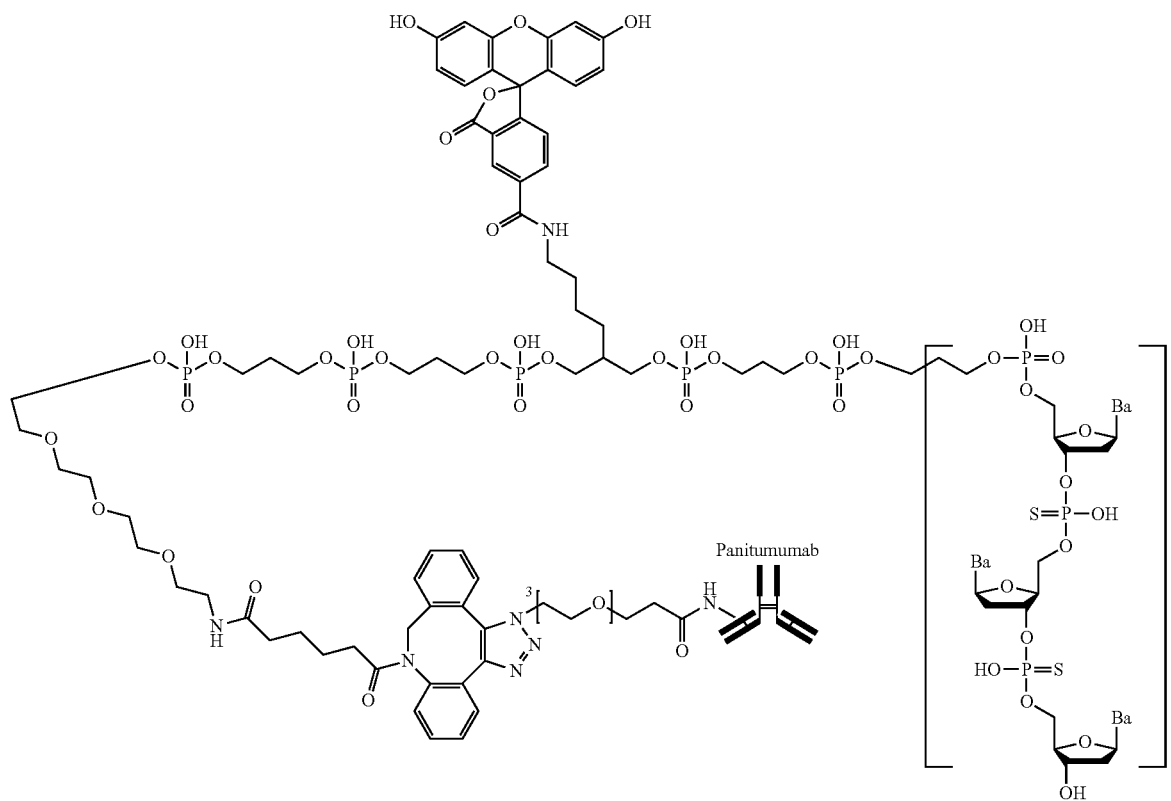

801

Sequence 5' to 3' =
TCC ATG AGC TTC CTG ATG CT

Non-fluorescein versions of 800 (compound 802) and 801 (compound 803), respectively were also prepared, i.e., where $R^1$ is hydrogen.

CTLA4 Antibody Conjugate

Following the procedure set forth above, product compounds 850 and 851 were also prepared, where $A_T$ is CTLA4. The hashed line (∼) represents the point of attachment for the other symmetrical half of the compound, not shown for clarity. Non-fluorescein versions of 850 and 851 were also prepared, i.e., where $R^1$ is hydrogen ("TC-CATGAGCTTCCTGATGCT" disclosed as SEQ ID NO: 5).

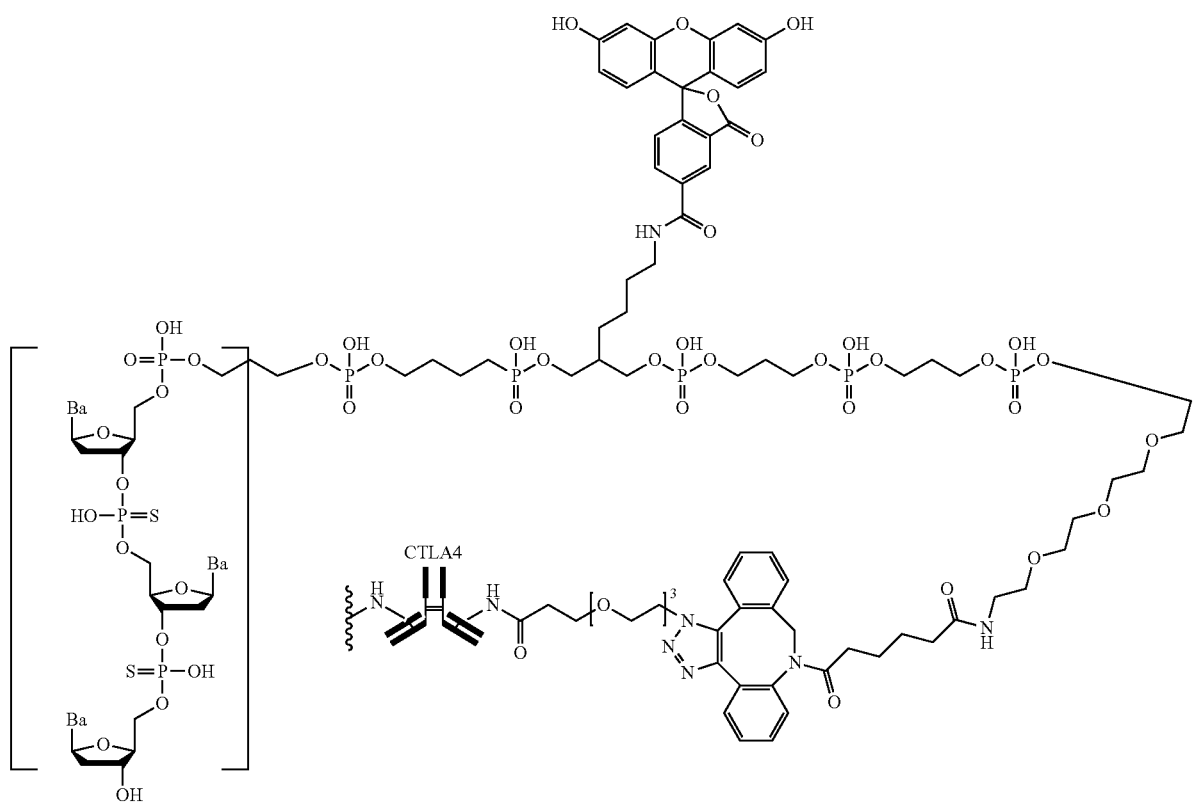

851

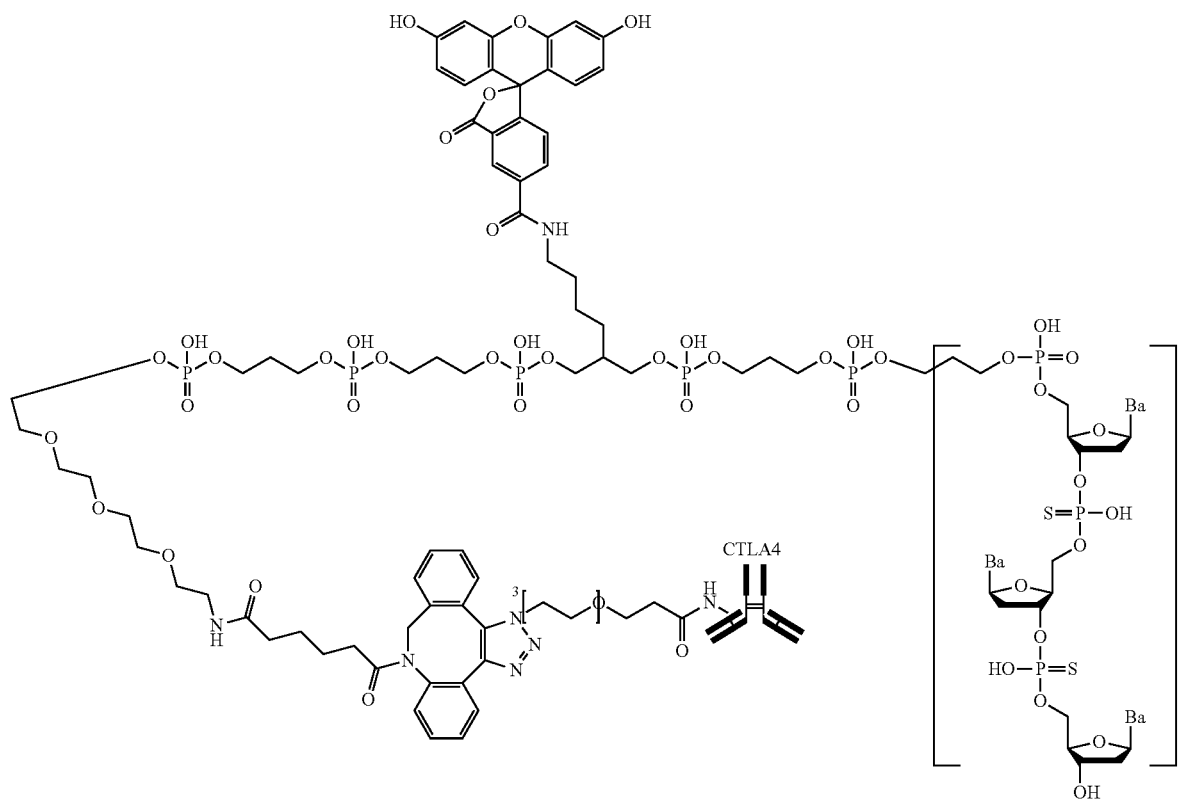

Sequence 5' to 3' =
TCC ATG AGC TTC CTG ATG CT

Figure 5:
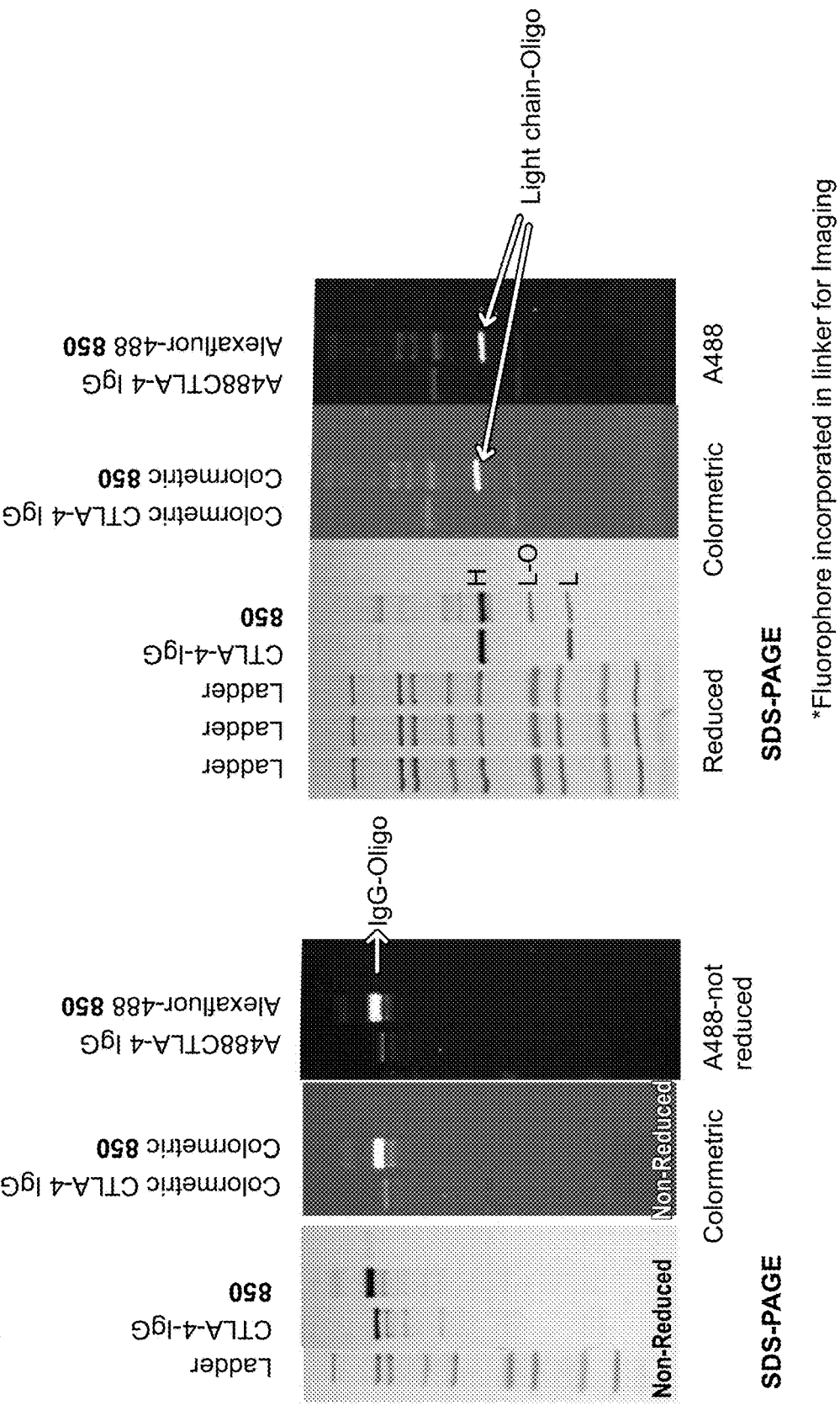
FIG. 5 illustrates SDS PAGE characterization of a compound 850, a compound of Formula I where $A_T$ is anti-CTLA4 IgG.
Figure 6:
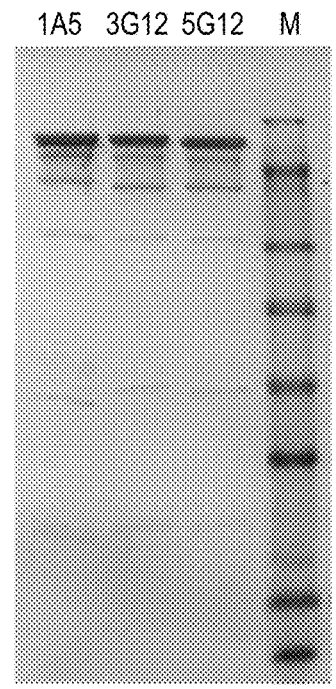
FIG. 6 is a Coomasie blue-stained SDS PAGE showing the expression of clones ST1A5 ("1A5"), ST3G12 ("3G12") and ST5G12 (5G12").

FIG. 5 shows the SDS Page characterization of compound 850. Non-fluorescein versions of 850 (compound 852) and 851 (compound 853), respectively were also prepared, i.e., where $R^1$ is hydrogen Anti-STAT3 Antibody Conjugates Following the procedure set forth above, product compounds 900, 901, 902, 903, 904, and 905 were also prepared, where $A_T$ is ST1A5, ST3G12, and ST5G12 respectively. The hashed line (⌇) represents the point of attachment for the other symmetrical half of the compound, not shown for clarity. Non-fluorescein versions of 900 (compound 900a), 901 (compound 901a), 902 (compound 902a), 903 (compound 903a), 904 (compound 904a), and 905 (compound 905a), respectively were also prepared, i.e., where $R^1$ is hydrogen ("TCCATGAGCTTCCTGATGCT" disclosed as SEQ ID NO: 5).

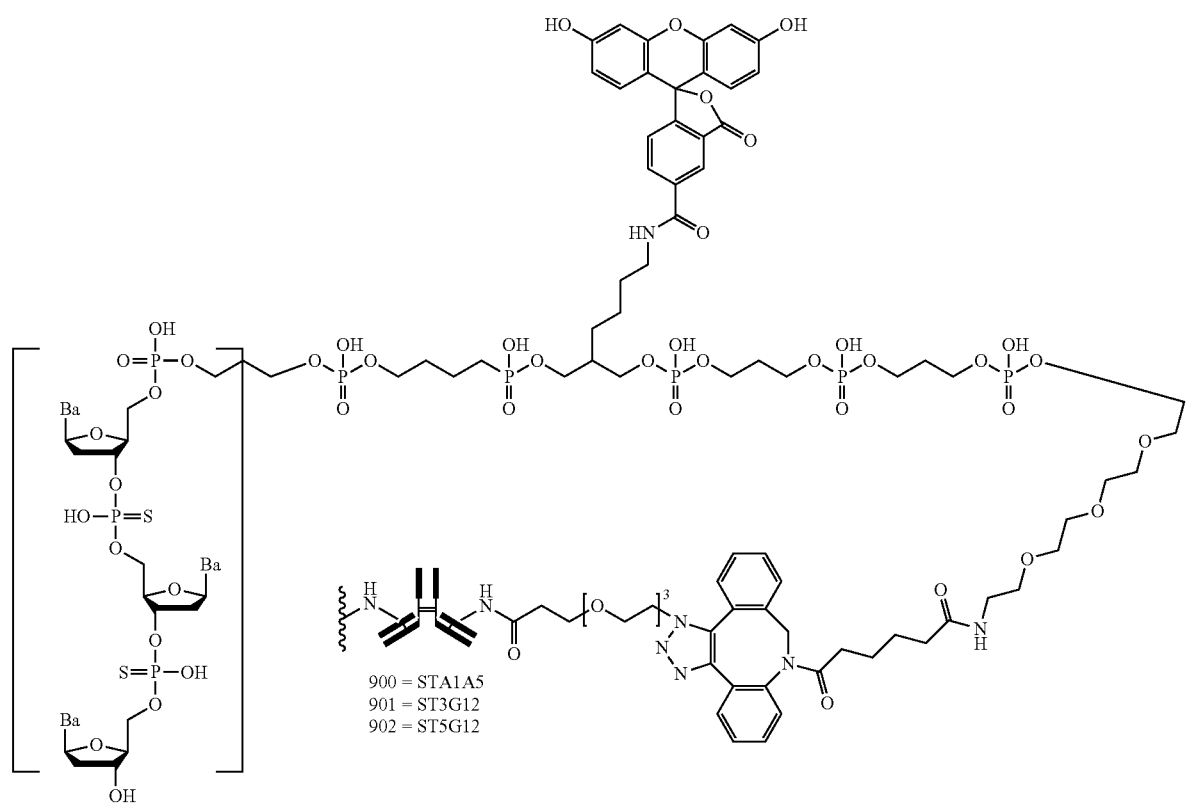

-continued
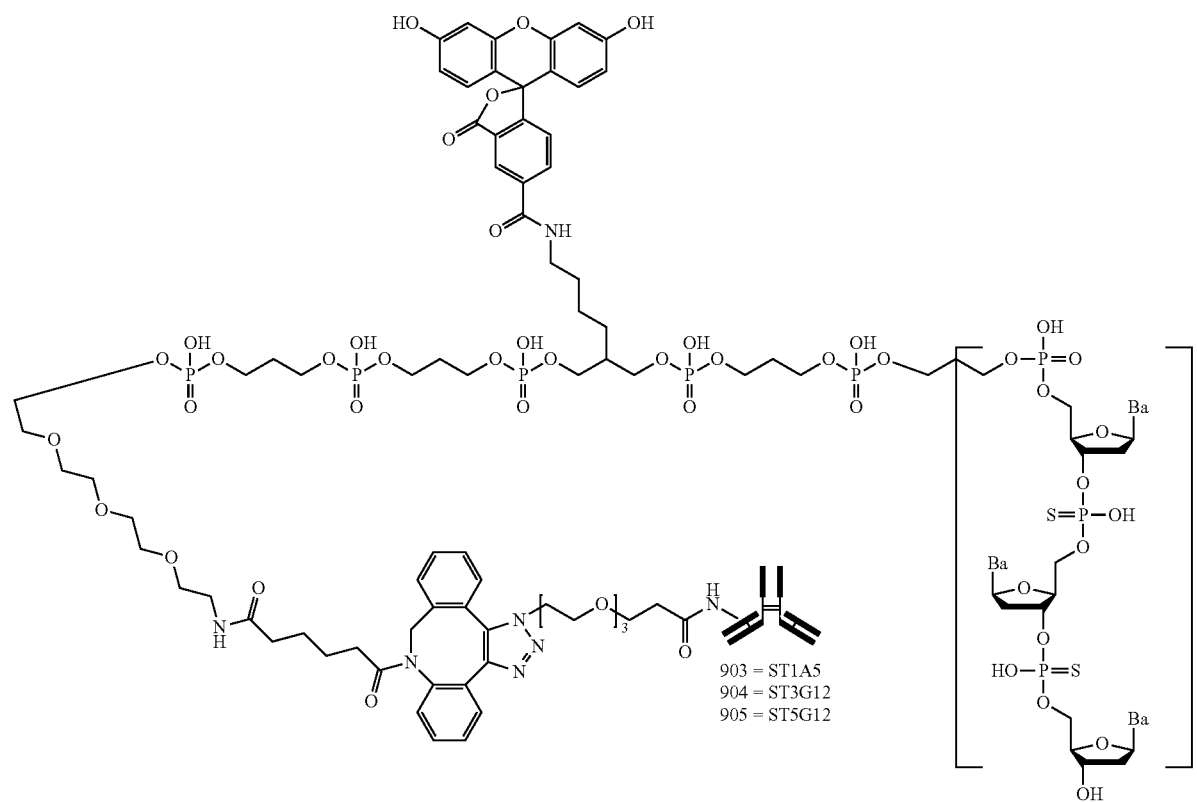
903 = ST1A5
904 = ST3G12
905 = ST5G12
Sequence 5' to 3' =
TCC ATG AGC TTC CTG ATG CT For example, compound 901 drawn in its entirety is

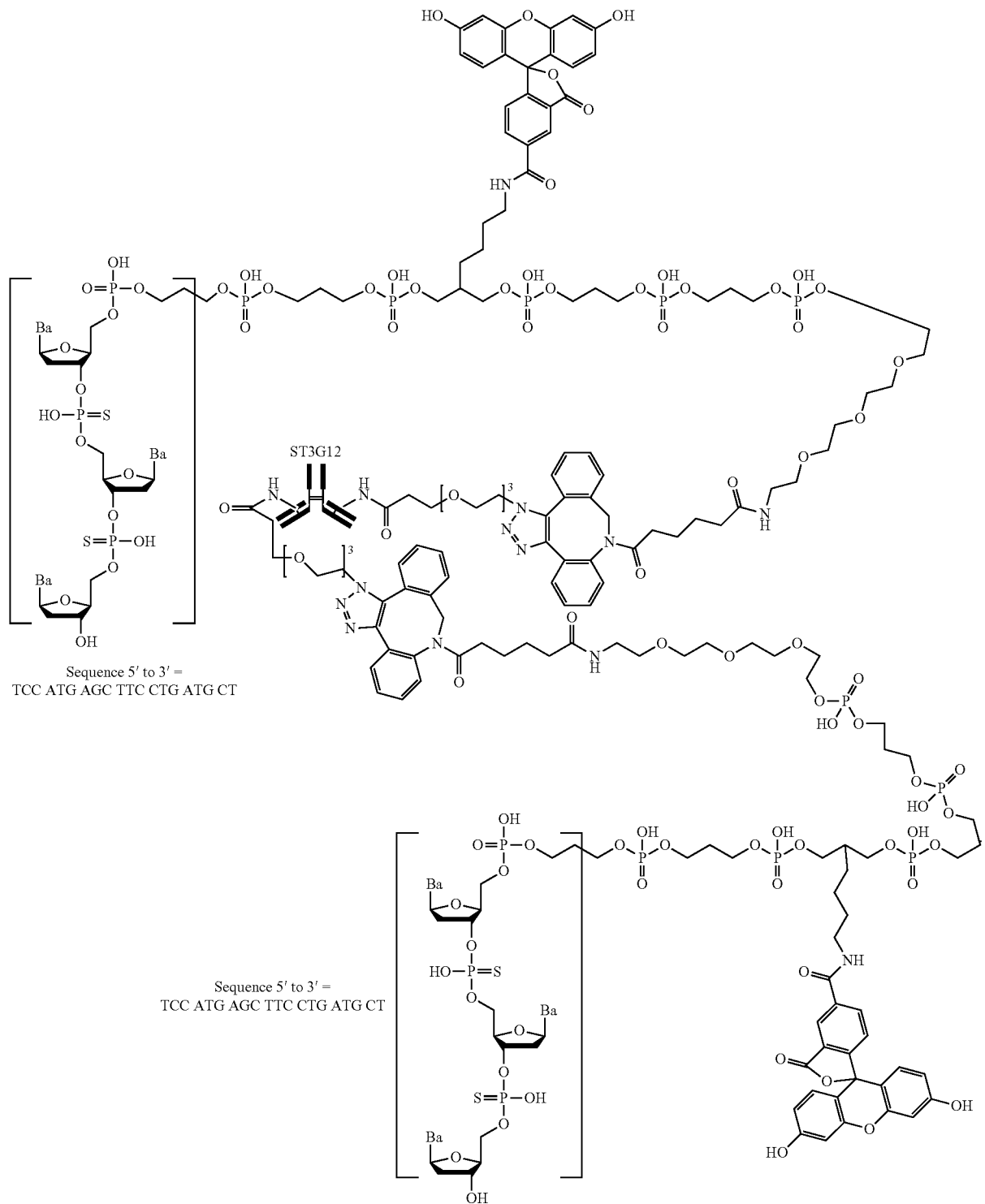

Sequence 5' to 3' =
TCC ATG AGC TTC CTG ATG CT

Sequence 5' to 3' =
TCC ATG AGC TTC CTG ATG CT

Anti-KRAS Antibody Conjugates

Following the procedure set forth above, compounds 910 and 911 were also prepared, where $A_T$ is a human anti-KRAS clone G12D as described in U.S. Provisional Application No. 62/407,982, filed Oct. 13, 2016. The hashed line (〰) represents the point of attachment for the other symmetrical half of the compound 910, not shown for clarity. Non-fluorescein versions of 910 (compound 912) and 911 (compound 913) were also prepared, i.e., where $R^1$ is hydrogen ("TCCATGAGCTTCCTGATGCT" disclosed as SEQ ID NO: 5).

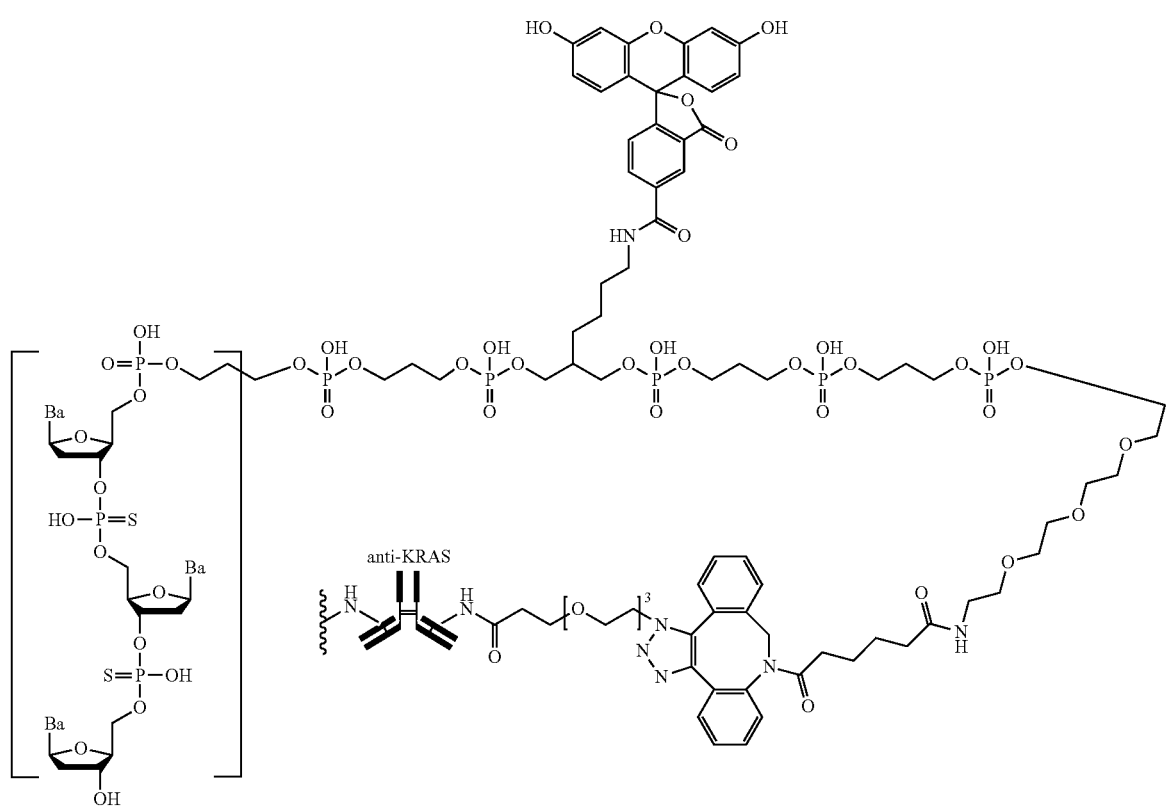
Sequence 5' to 3' =
TCC ATG AGC TTC CTG ATG CT

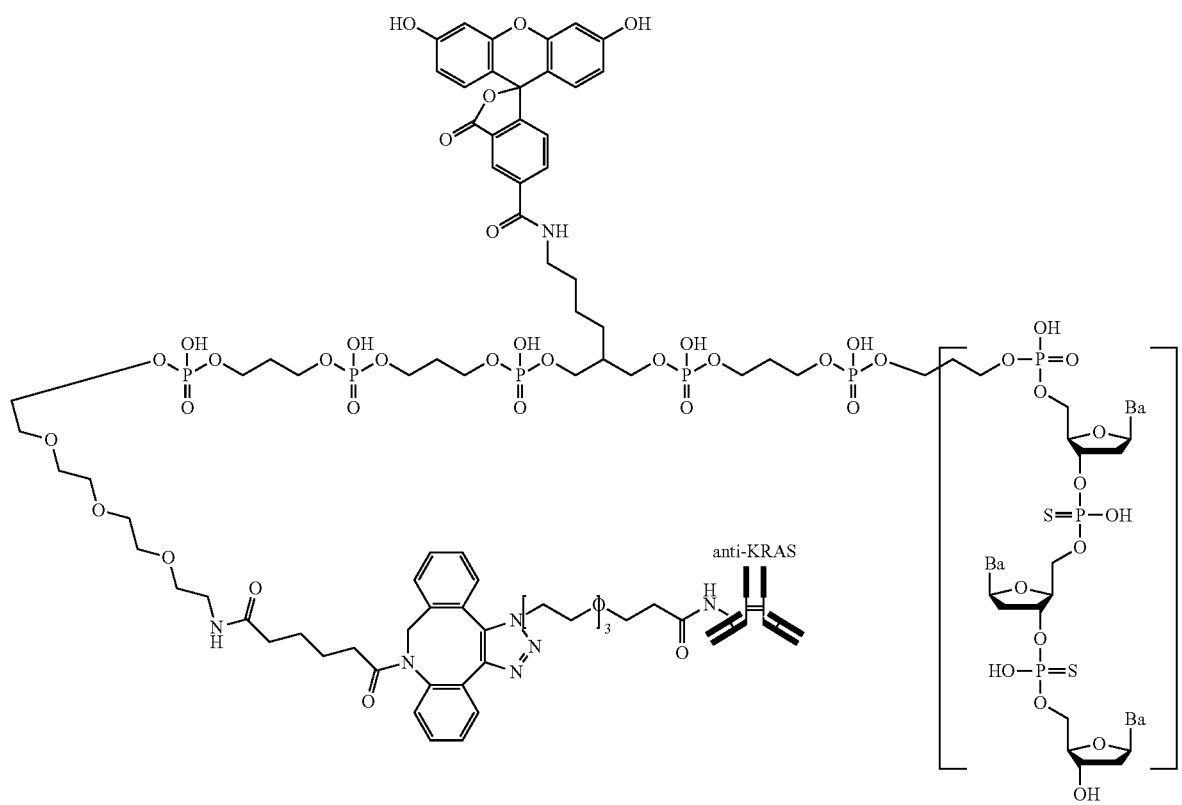

911

Sequence 5' to 3' =
TCC ATG AGC TTC CTG ATG CT

Cetuximab Antibody Conjugates

Following the procedure set forth above, compounds 922 and 923 were also prepared, where $A_T$ is Cetuximab (Erbitux®). The hashed line (~~~) represents the point of attachment for the other symmetrical half of the compound, not shown for clarity. Non-fluorescein versions of 922 (compound 921) and 923 (compound 920), respectively were also prepared, i.e., where $R^1$ is hydrogen ("TCCATGAGCTTCCTGATGCT" disclosed as SEQ ID NO: 5).

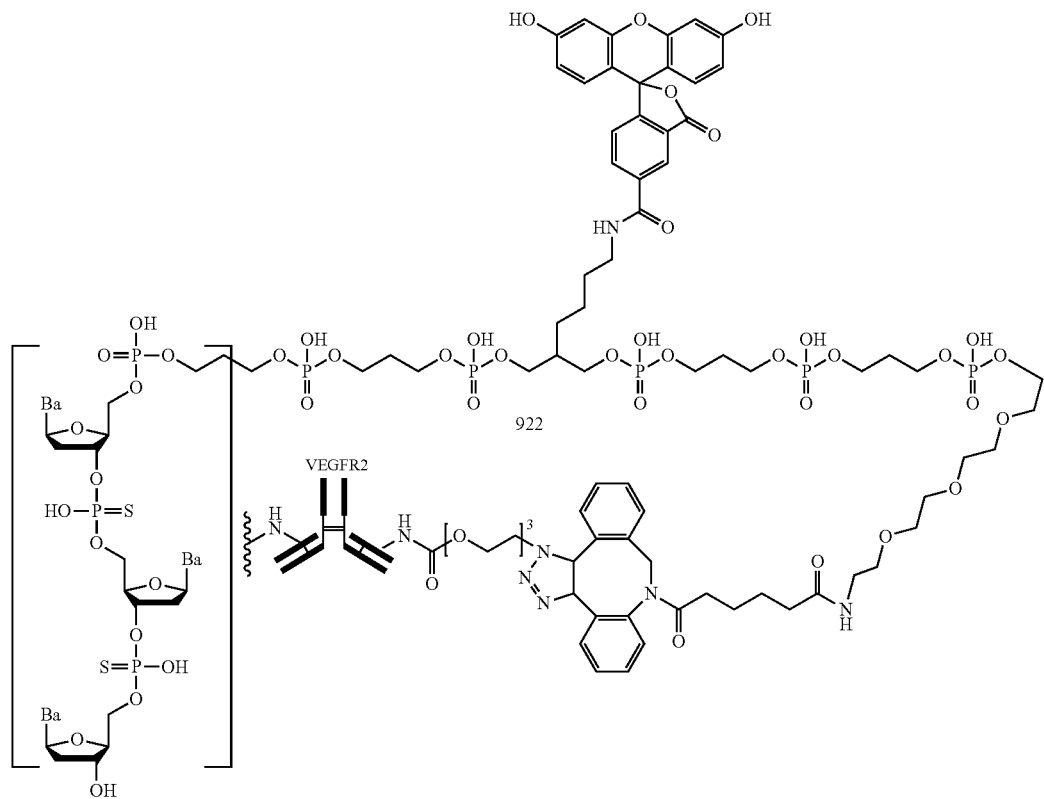
Sequence 5' to 3' =
TCC ATG AGC TTC CTG ATG CT
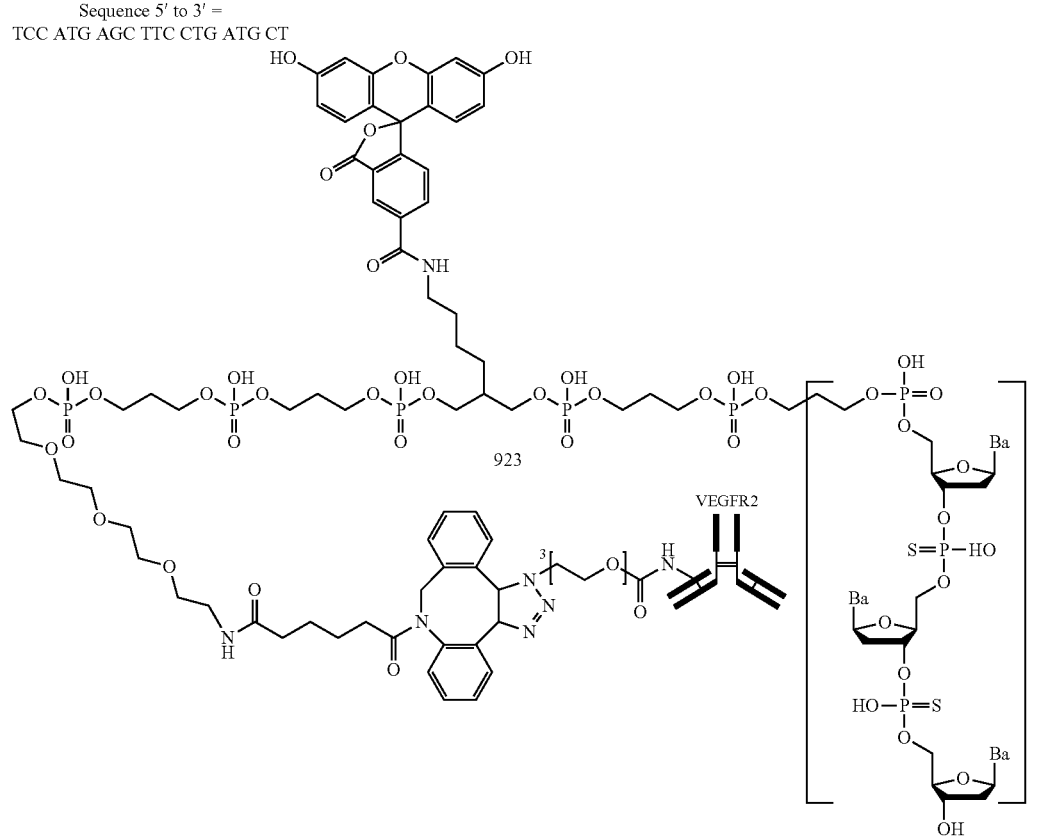
Sequence 5' to 3' =
TCC ATG AGC TTC CTG ATG CT

Biological Assays

Panitumumab Antibody Conjugate Delivery

Treatment of human cancer cells with compound 802 efficiently blocked EGF-induced EGFR phosphorylation, compared to unmodified Panitumumab. This data (e.g., FIG. 4) further showed that compound 802 downregulated mRNA expression of BCL2L1, one of EGFR-regulated genes involved in cancer cell proliferation.

Figure 3:
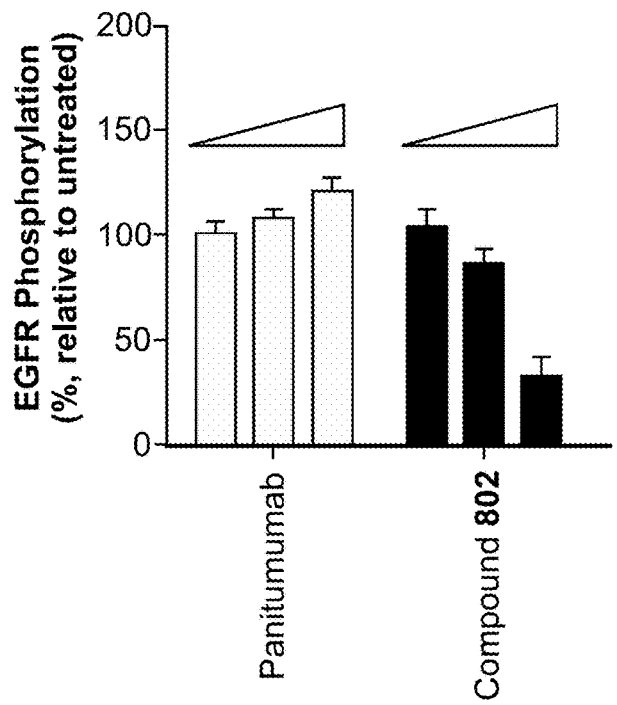
FIG. 3 illustrates the inhibition of ligand-induced EGFR phosphorylation in human breast cancer cells lines using compound 802, a compound of Formula I where $A_T$ is Panitumumab (Vectibix®).

Compound 802 was used in a Phospho-ELISA assay to determine the levels of phosphorylated EGFR in MDA-MB-468 triple negative breast cancer cells treated with the different dose of antibodies as indicated. FIG. 3 shows that compound 802 inhibits ligand-induced EGFR phosphorylation in human breast cancer cells. Cells were starved for 18 hours, and then treated with the different amount of the indicated compound/antibody for an hour. 50 ng/ml of EGF was added to the cells for 10 min to induce ligand-induced EGFR phosphorylation. Phosphor-EGFR levels were measured by ELISA based assay (Duoset, R&D). Arrow (FIG. 3) indicates the increased concentration of compound/antibody.

Figure 4:
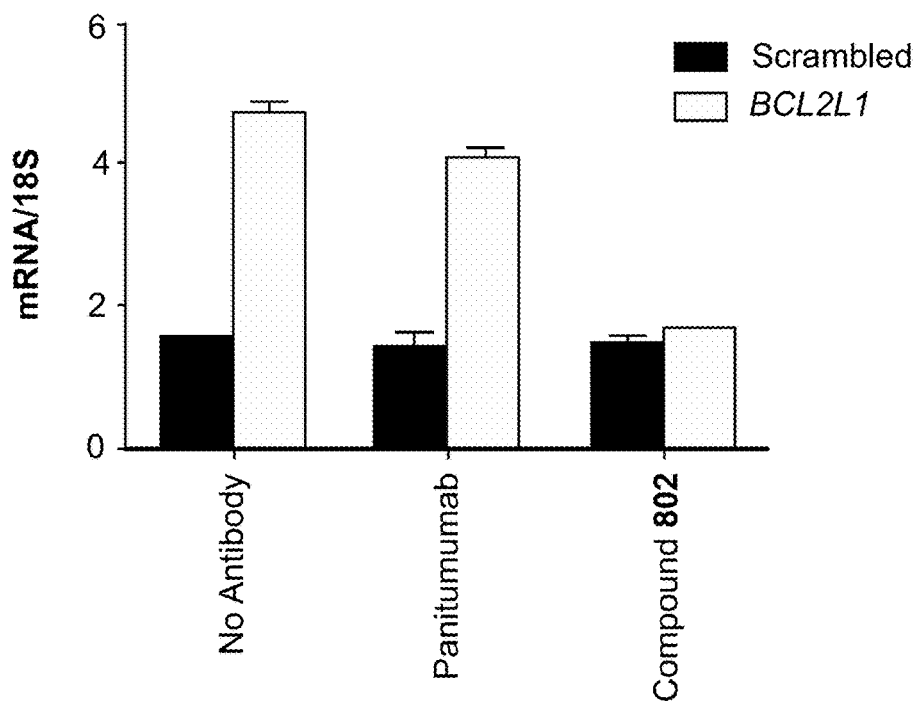
FIG. 4 illustrates the inhibition of mRNA expression of EGFR-downstream anti-apoptotic gene in human cancer cells using compound 802, a compound of Formula I where $A_T$ is Panitumumab (Vectibix®).

FIG. 4 shows compound 802 potently inhibits mRNA expression of EGFR-downstream anti-apoptotic gene in human cancer cells. A graph showing the mRNA levels (mRNA/18S) of BCL2L1 (Bcl-xL) in MDA-MB-468 cells treated with the 20 µg/ml of indicated compound/antibody for 18 hours. Cells were incubated with fluorescent-labeled RNA probes specific to BCL2L1 gene or control probes with the scrambled sequences (EMD Millipore, SmartFlare RNA detection probe), for another 18 hours.

STAT3 Antibody Binding of Non-Conjugates

Three anti-STAT3 antibodies, i.e., ST1A5, ST3G12, ST5G12, were expressed and purified. The designations 1A5, 3G12 and 5G12 refer to ST1A5, ST3G12 and ST5G12, respectively, and are used interchangeably throughout.

Binding of antibody clones ST1A5, ST3G12, ST5G12 was tested in an enzyme-linked immunsorbant assay (ELISA) assay to assess the binding of the candidate anti-STAT3 antibodies to cellular targets.

Figure 7:
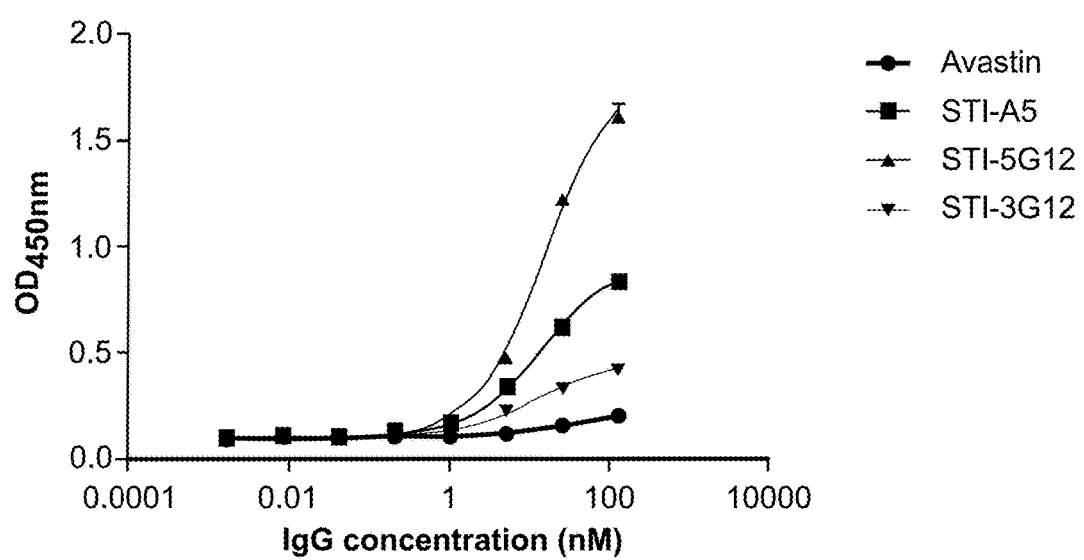
FIG. 7 is a graph that shows the results of an ELISA assay used to assess the binding of the STAT3 clones ST1A5, ST3G12 and ST5G12 to cellular antigens in U251 malignant glioblastoma cells.

U251 malignant glioblastoma cells were seeded overnight in a 96 well plate. Cells were fixed with paraformaldehyde (PFA) and permeabilized with Triton reagent, and then incubated with serial dilutions of the antibody candidates for one hour. Following incubations, cells were washed and incubated for 30 minutes with horseradish peroxidase (HRP) conjugated anti-human IgG. Chemiluminescence was measured on a plate reader. Bevacizumab (Avastin), a monoclonal antibody that inhibits vascular endothelial growth factor A (VEGF-A) was used as a negative control. The results are shown in FIG. 7, and demonstrate the sensitivity and the specificity for STAT3 of the anti-STAT3 antibodies ST1A5, ST3G12 and ST5G12.

Next, the binding of the candidate anti-STAT3 antibodies to cellular targets was tested in cell binding assays using MDA-MB-435 breast cancer cells and U251 cells. The cells were seeded overnight in a 96 well plate, then fixed with PFA and permeabilized with methanol. Cells were incubated with serial dilutions of the anti-STAT3 antibody candidates ST1A5, ST3G12 and ST5G12 for one hour and 30 minutes. Following incubation, the cells were washed and incubated for 30 minutes with phycoerythrin (PE) conjugated anti-human IgG. Fluorescence was measured on an Intellicyte high-throughput flow cytometry analyzer. The results, shown in FIG. 8A and FIG. 8B, demonstrate that this assay was specific and sensitive for STAT3. FIG. 8A shows binding of the anti-STAT3 antibodies ST1A5, ST3G12 and ST5G12 to cellular antigens in MDA-MB-468 cells (breast cancer cell line) and FIG. 8B shows binding of the anti-STAT3 antibodies ST1A5, ST3G12 and ST5G12 in U251 cells (glioblastoma). Bevacizumab (Avastin), a monoclonal antibody that inhibits vascular endothelial growth factor A (VEGF-A) was used as a negative control. As shown in FIG. 8A and FIG. 8B, the anti-STAT3 antibodies ST5G12 and ST3G12 both bound STAT3, with ST5G12 being an especially strong binder. The ST1A5 antibody did not show strong STAT3 binding to cellular antigens in MDA-MB-468 and U251 cells in comparison to antibodies ST5G12 and ST3G12.

Figure 9:
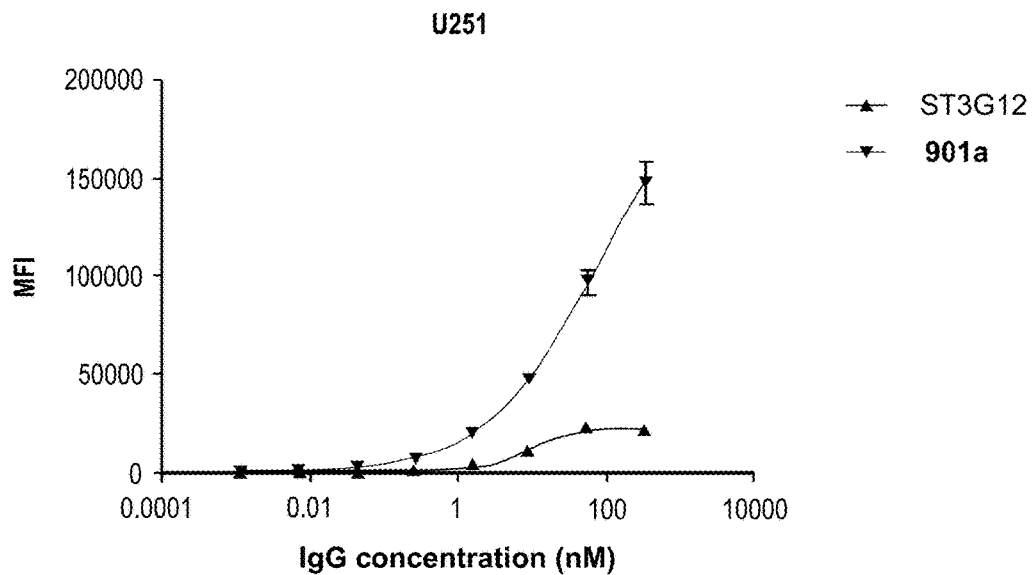
FIG. 9 is a graph that shows the results of a cell binding assay to assess binding of naked anti-STAT3 ST3G12 antibodies (ST3G12) and compound 901a, a compound of Formula I where $A_T$ is ST3G12, to cellular antigens in U251 cells.

Cell binding of naked anti-STAT3 ST3G12 antibodies (ST3G12) versus compound 901a was assessed in U251 cells. Cells were lifted, permeabilized and incubated with increasing amounts of naked anti-STAT antibodies and compound 901a in PBS+/−2% fetal bovine serum (FBS). After 45 minutes at room temperature, cells were washed twice and incubated with phycoerythrin (PE) conjugated-anti-human IgG for 20 minutes at room temperature in the dark. Cells were then washed and analyzed by high throughput flow cytometry (HTFC). The results are shown in FIG. 9 for assessment of antibody binding to cellular antigens in U251 cells. As described in FIG. 9, binding of the naked anti-STAT3 antibody, ST3G12, was considerably lower than that of compound 901a. For compound 901a, higher binding was detected in each cell line relative to the naked antibody, independent of the level of STAT3 expression.

Next, binding affinity of the naked anti-STAT3 antibody and compound 901a was determined. Biacore T200 was used to measure the affinity of anti-STAT antibody and compound 901a to human STAT3. Anti-human Fc antibody (GE, BR-1008-39) was immobilized on a CM5 sensor chip to approximately 1000 RU using standard NHS/EDC coupling methodology. Antibodies (approximately 10 ug/ml) were captured for 60 seconds at a flow rate of 10 ul/min Recombinant human STAT3-GST was serially diluted 2-fold into running buffer (HBS-EP+, starting from 100 nm). All measurements were conducted at a flow rate of 30 ul/min Surfaces were regenerated with 3M $MgCl_2$ (from human antibody kit) for 60 seconds. A 1:1 (Langmuir) binding model was used to fit the data. The results are shown in Table 2, below for anti-STAT3 antibody, ST3G12, and compound 901a, labeled in Table 2 as ST3G12-PS.

TABLE 2

| name | ka (1/Ms) | kd (1/s) | Rmax (RU) | KD (M) | Chi2 |
|---|---|---|---|---|---|
| Anti-STAT3 | 5.97E4 | 3.22E−4 | 174 | 5.39E−9 | 3.06 |
| Anti-STAT3-PS | 4.94E5 | 1.1E−4 | 73.1 | 2.22E−10 | 3.6 |

As shown in Table 2, compound 901a improved the affinity of the antibodies to STAT3. The data in Table 2 indicates that compound 901a bound the antigen with more affinity when compared to unmodified anti-STAT3 antibody (the smaller the $K_D$ the greater the affinity of the antibody for its antigen). No binding of either the unmodified anti-STAT3 antibodies or compound 901a to GST protein was observed in the assay, suggesting that the difference in interaction rate of antigen-antibody contributes to the differential binding affinity.

Figure 10:
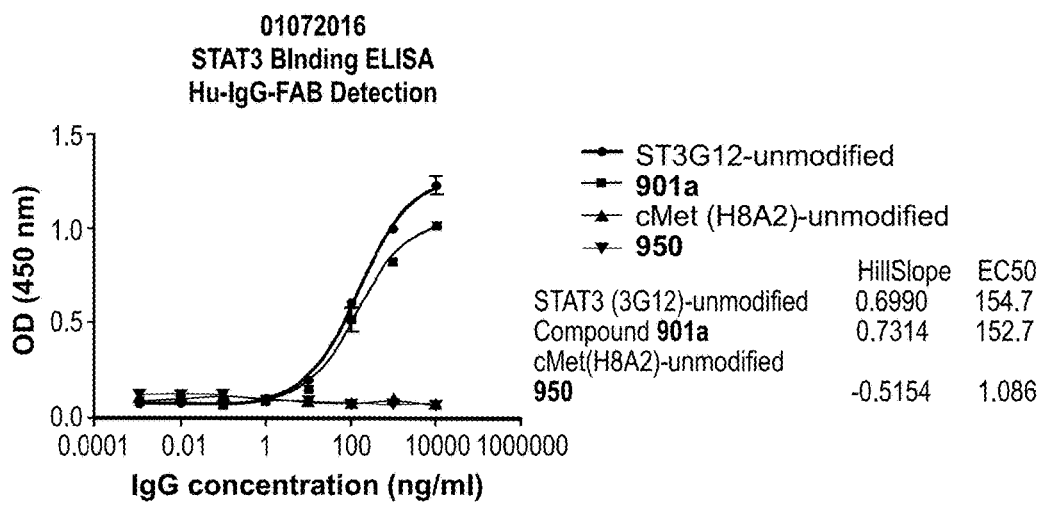
FIG. 10 is a graph that shows the results of an ELISA assay used to assess the binding of the anti-STAT3 ST3G12 antibodies that were unmodified (ST3G12-unmodified) and with compound 950 to human IgG.
Figure 11:
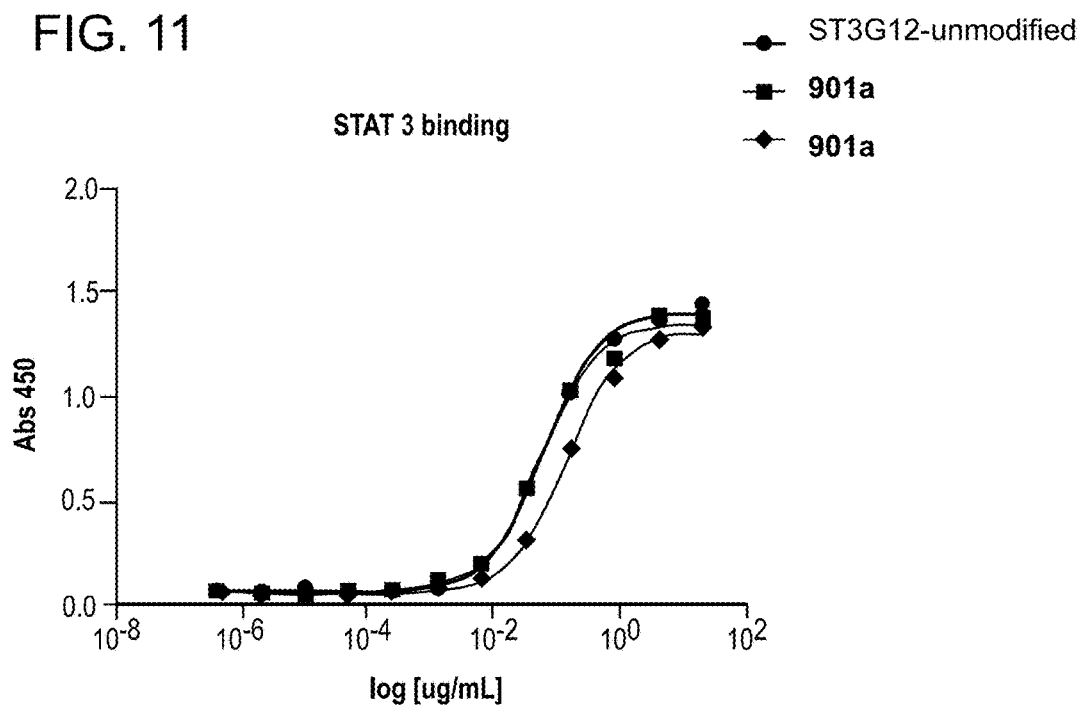
FIG. 11 is a graph that shows the results of an ELISA assay used to assess the binding of the anti-STAT3 ST3G12 antibodies that were unmodified and with compound 901a to recombinant human STAT3 proteins.

The binding of the unmodified antibody and compound 901a was also tested in an ELISA assay used to assess the binding of the anti-STAT3 ST3G12 antibodies that were unmodified and with compound 901a to human IgG and to recombinant human STAT3 proteins and to. The results are shown in FIG. 10 and FIG. 11. Compound 901a showed a slightly lower binding than the unmodified ST3G12 antibody. However, the $EC_{50}$ was the same. Given these results, it is possible that compound 901a interfered with the detection. Anti-cMet unmodified ((H8A2)-unmodified)) and control compound 950 (which is compound 901a with c-Met (see WO 2013/192594) replaced for ST3G12 at $A_T$) were used as controls.

Anti-STAT3 Antibody Accumulation and Internalization

Figure 12A:
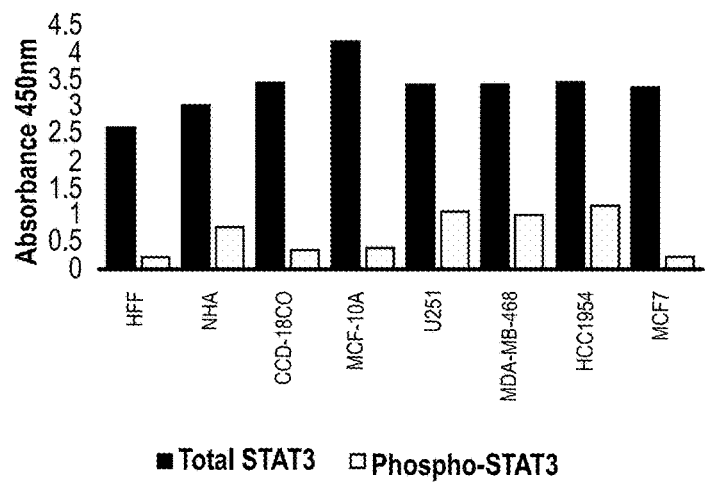
FIG. 12A is a graph that shows the results of an ELISA assay carried out to determine the total level of STAT3 and the level of phosphorylated STAT3 (phospho-STAT3) in human foreskin fibroblast (HFF), normal human astrocytes (NHA), normal colon fibroblasts (CCD-18CO), normal breast epithelial cells (MCF-10A), gliosblastoma (U251), triple negative breast cancer (MDA-MB-468), triple negative breast cancer (HCC1954) and ER+ breast cancer (MCF-7).
Figure 12B:
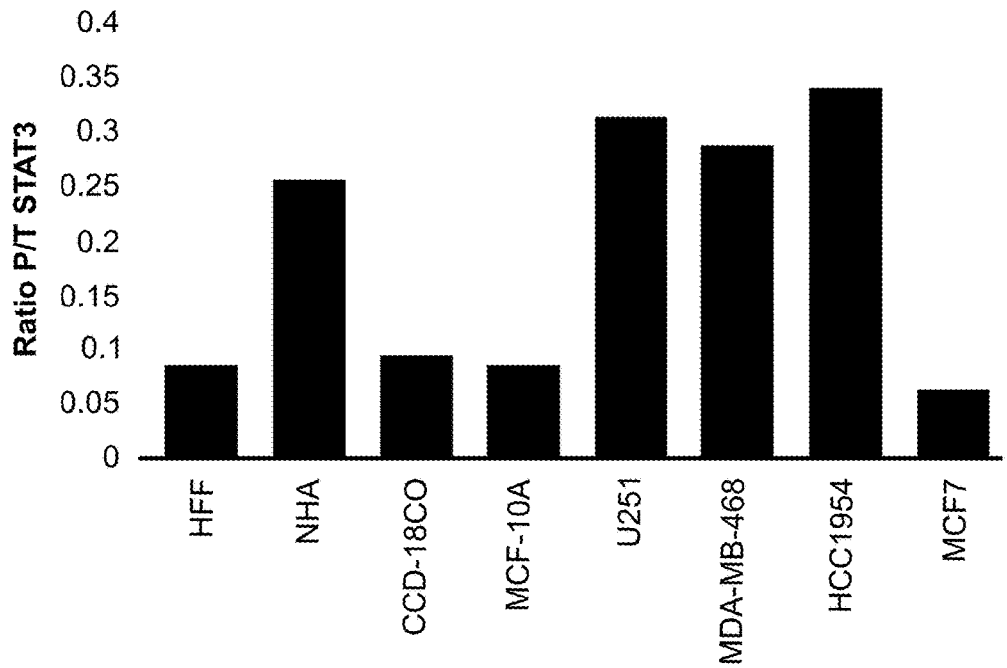
FIG. 12B is a graph that shows the ratio of phosphorylated to total STAT3 (ratio P/T STAT3) in the cells tested in FIG. 12A.

The relative STAT3 level in various test cell lines is shown in FIG. 12A and FIG. 12B. The total level of STAT3 and the level of phosphorylated STAT3 (phospho-STAT3) in human foreskin fibroblast (HFF), normal human astrocytes (NHA), normal colon fibroblasts (CCD-18CO), normal breast epithelial cells (MCF-10A), gliosblastoma (U251), triple negative breast cancer (MDA-MB-468), triple negative breast cancer (HCC1954) and ER+ breast cancer (MCF-7) is shown in FIG. 12A. Levels of phosphorylated STAT3 were determined by flow cytometry using an antibody to phospo-STAT3. Controls used were primary antibody alone, secondary antibody alone and an isotype matched control IgG. FIG. 12B shows the ratio of phosphorylated STAT3 to total STAT3 in these cells.

Figure 13A:
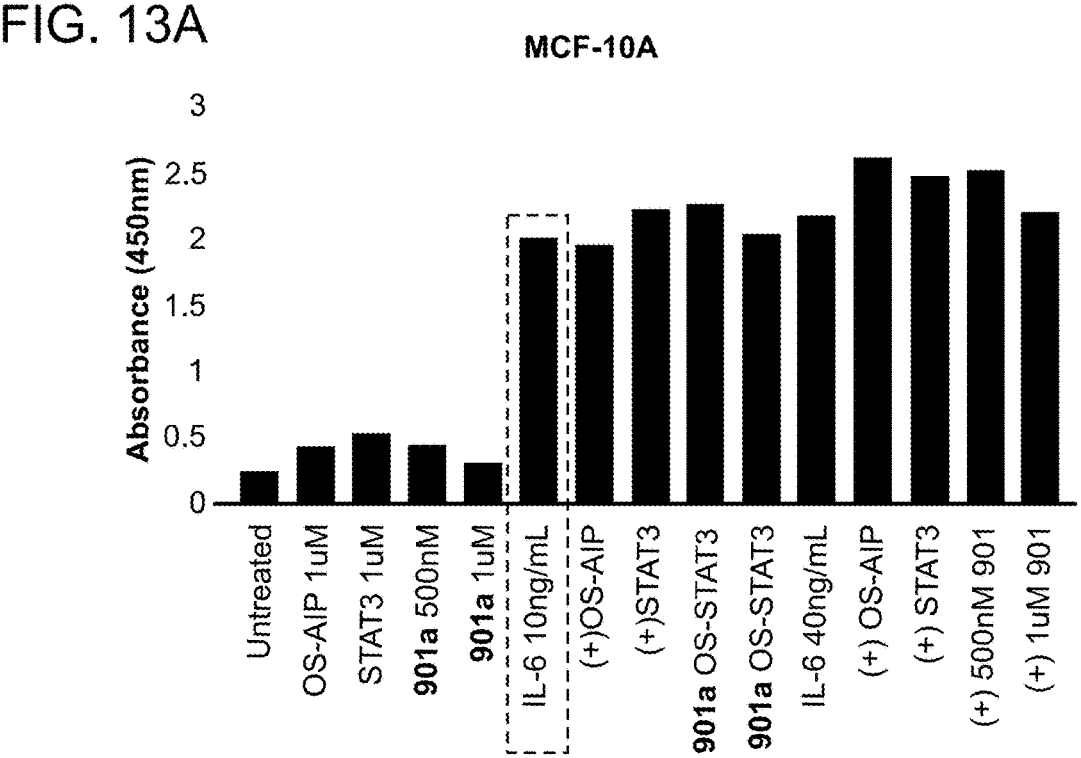
FIG. 13A is a graph that shows the results of experiments to determine the effect of compound 901a on STAT3 phosphorylation in MCF-10A cells.
Figure 13B:
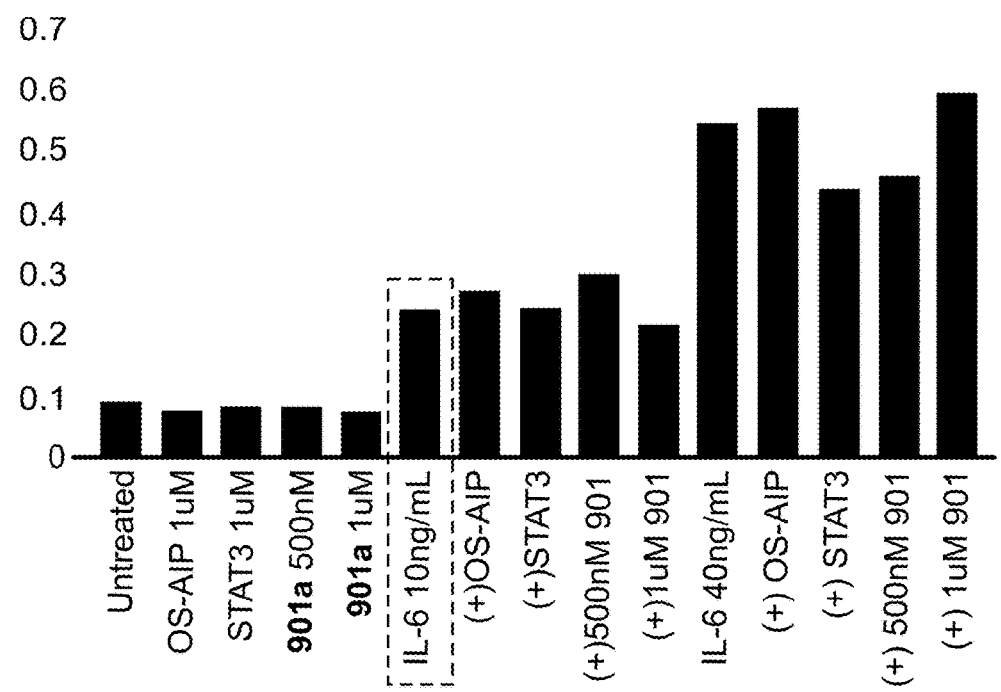
FIG. 13B is a graph that shows the results of experiments to determine the effect of compound 901a on STAT3 phosphorylation in MCF7 cells. The experimental procedure was the same as described in FIG. 13A.

Normal breast epithelial cells (MCF-10A) and ER+ breast cancer cells (MCF-7) were treated with naked ST3G12 antibody and compound 901a to determine the effect on STAT3 phosphorylation. Cells were pre-treated overnight with antibody, and then stimulated with various concentrations of IL-6 for 20 minutes (10 ng/ml or 40 ng/ml). IL-6 is a STAT3 activator. Cells were then lysed and the protein lysates were subjected to ELISA to determine the phosphorylation status. The results shown in FIG. 13A for MCF-10 cells and in FIG. 13B for MCF-7 cells, demonstrate little to no effect of the naked ST3G12 antibody or compound 901a on STAT3 phosphorylation. These results suggest that compound 901a is not interfering with the STAT3 phosphorylation site. "OS-AIP" refers to an oligosaccharide conjugated bacterial AIP protein, used as a control.

MDA-MB-468 triple negative breast cancer cells, which have a high level of STAT3 activity (STAT3 high) (see FIG. 12A) were treated with 10 ug/ml of compound 901a in increasing proportions of human serum (1%, 5%, 10% and 20%), for 90 minutes at 37° C., to induce STAT3 activation. Cells were then fixed, permeabilized and stained with anti-human IgG Alexa 546. It was found that compound 901a accumulated in the MDA-MB-468 cells, and increasing accumulation was seen with increasing concentrations of serum.

The same experiments were repeated in the U251 glioblastoma cell line, which also has high levels of STAT3 activity, as described in FIG. 12A. U251 cells were treated with 10 ug/ml of compound 901a in increasing proportions of human serum (1%, 5%, 10% and 20%), for 90 minutes at 37° C. Cells were then fixed and stained with anti-human IgG Alexa546. It was found that compound 901 accumulated in the U251 cells, and increasing accumulation was seen with increasing concentrations of serum (data not shown). MCF-10A, a normal human mammary epithelial cell line with low levels of STAT3 activity (STAT3 low), was described in FIG. 12A and FIG. 12B. This cell line was also tested according to the above protocol. It was found that compound 901a accumulated in the MCF-10A cells with increasing serum concentrations (1%, 5%, 10% and 20% serum) (data not shown).

A time course experiment was carried out showing compound 901a accumulation in MDA-MB-468 cells (STAT3 high). Cells were seeded in 96 well plates overnight. 20 ug/ml of compound 901a-Alexa488 antibody was added for the indicated duration of 0.5, 2, 4, 6, 8 and 24 hours. Following incubation with the antibody for the indicated time, cells were fixed and imaged using Incucyte. FIG. 14A panel (i) and panel (ii) shows that accumulation of the antibody increased as time increased. Panel (ii) shows the data from panel (i) normalized to cell count. FIG. 14B panel (i) and panel (ii) shows the same experiments, performed in MCF-10A cells (STAT3 low). The results from the experiments done with the STAT3 low MCF-10A cells were similar to those from the STAT3 high MDA-MB-468 cells, showing that accumulation of compound 901a increased as time increased.

Figure 14C:
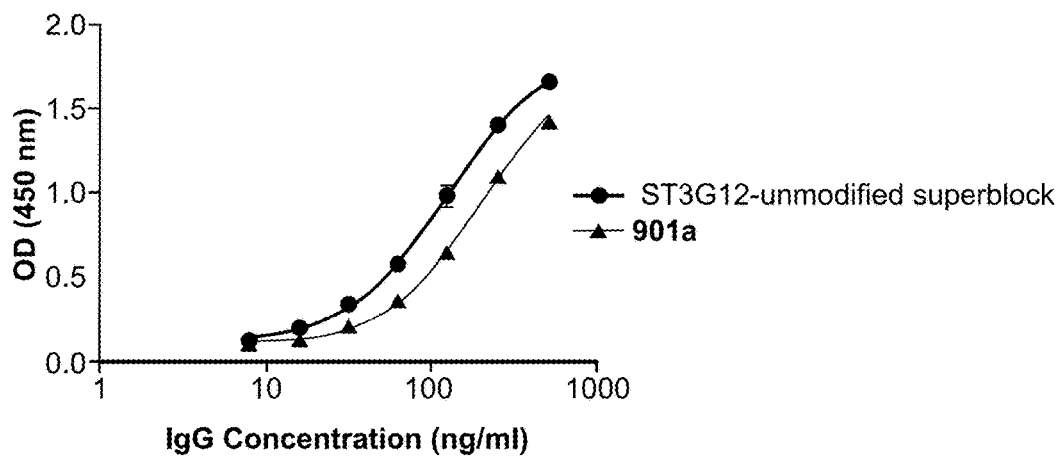
FIG. 14C is a graph that shows the results of an ELISA experiment carried out to show that modification of compound 901a did not affect its binding affinity to human IgG. Superblock refers to the blocking buffer used in the ELISA assay.
Figure 14D:
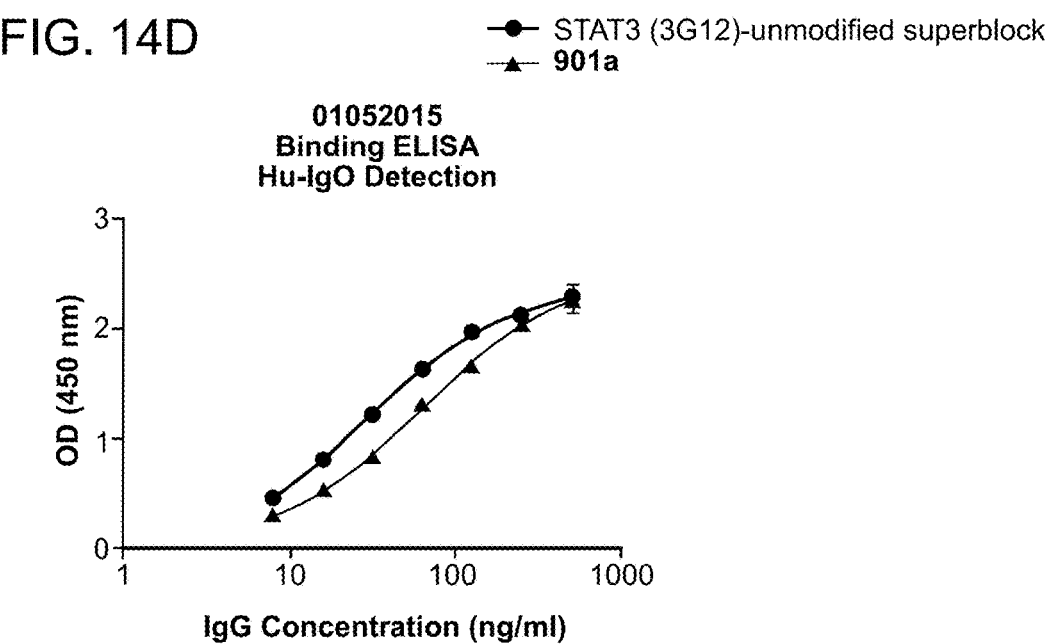
FIG. 14D is a graph that shows the results of an ELISA experiment carried out to show that modification of compound 901a did not affect its binding affinity.

FIG. 14C and FIG. 14D show the results of ELISA experiments carried out to show that modification of the ST3G12 antibody with the PS oligomer did not affect its binding affinity. ST3G12-unmodified refers to the unmodified anti-STAT3 antibody (FIG. 14C). Superblock refers to the blocking buffer used in the ELISA assay. FIG. 14D shows the results of an ELISA experiment carried out to show that modification of the antibody did not affect its binding affinity. ST3G12-unmodified refers to the unmodified anti-STAT3 antibody. Superblock refers to the blocking buffer used in the ELISA assay.

MDA-MB-468 triple negative breast cancer cells, which have a high level of STAT3 activity (STAT3 high) were treated with 10 ug/ml of compound 901a in increasing proportions of human serum (1%, 5%, 10% and 20%), for 90 minutes at 37° C., to induce STAT3 activation. Cells were then fixed, permeabilized and stained with anti-human IgG Alexa 546. The results in FIG. 15A. show that compound 901a accumulated in the MDA-MB-468 cells, and increased accumulation is seen with increased concentrations of serum.

Cellular Uptake of Compounds

Experiments were carried out to confirm that compound 901a was penetrating the cells. Briefly, previously cleaned glass coverslips were coated with collagen for 2 hours at 37° C. 100,000 U251 cells were seeded on the coverslips. Media was removed, and cells were rinsed once with fluorobrite. Next, 20 ug/mL of the specified antibody was added for 2 hours at 37° C. Cells were fixed in 4% PFA for 15 minutes and then permeabilized with 0.1% TritonX for 15 minutes. Cells were blocked with 3% BSA for 30 minutes and 1:250 GAH-Alexa fluor 488 was added for 1 hour. Next, 200× wheat germ agglutinin Alexa fluor 555 (WGA 555) and 1:1000 DAPI was added for 30 minutes. Cells were washed 3× with PBS and mounted with prolong gold anti-fade. Using microscopy, it was found that cell penetration was observed from all the compound 901a and compound 901 treated samples. The negative control, the unmodified ST3G12 antibody, showed no internalization. The results are shown in the microscopic images in FIG. 15A, FIG. 15B, and FIG. 15E (to compound 901).

In FIG. 15B, U251 cells were treated with 10 ug/ml of compound 901a antibody in increasing proportions of human serum (0% and 20%) for 90 minutes at 37° C. In FIG.

Figure 15D:
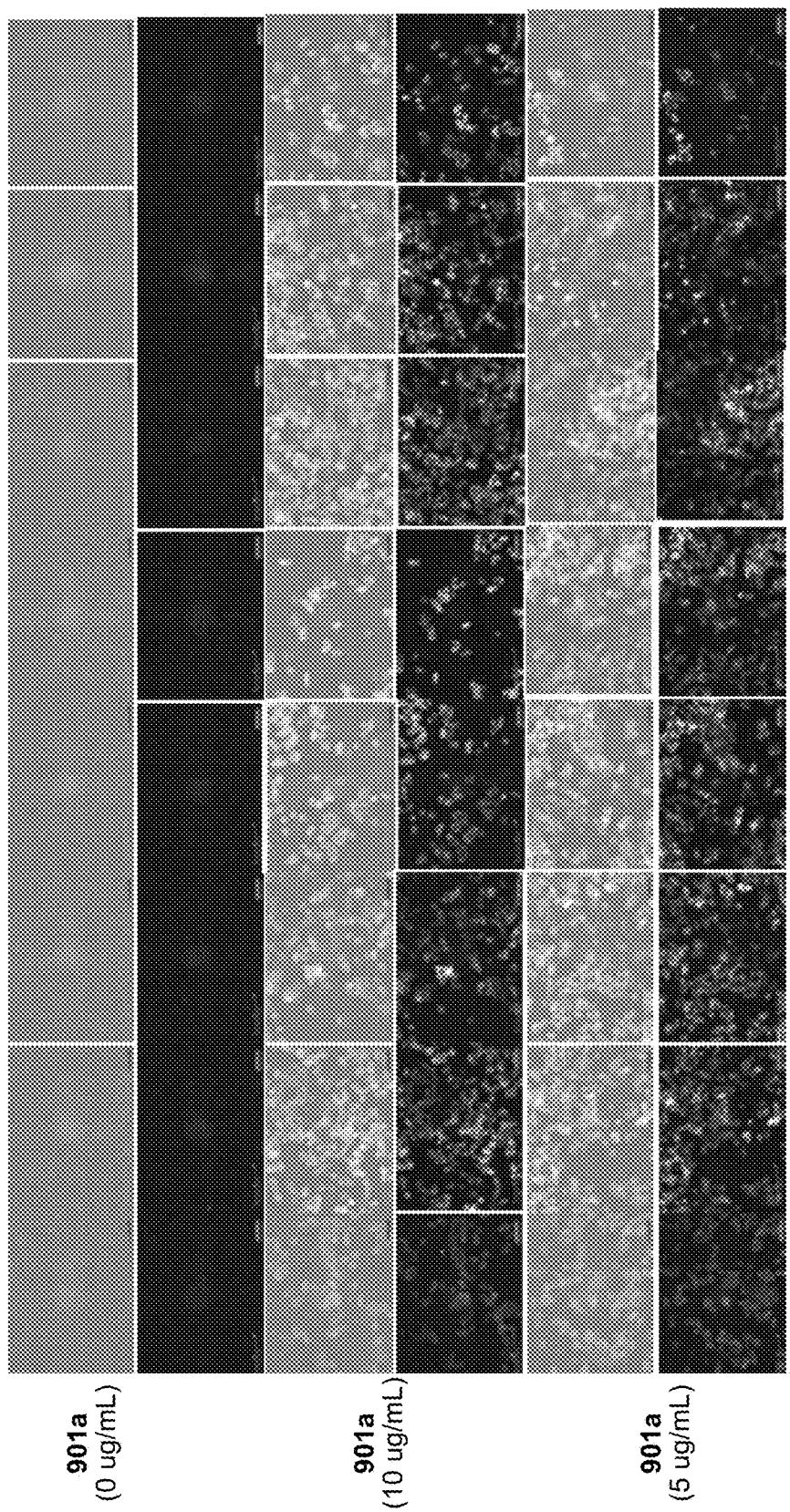
FIG. 15D is a microscopic image of compound 901a in MDA-MB-468 human breast cancer cells.
Figure 15E:
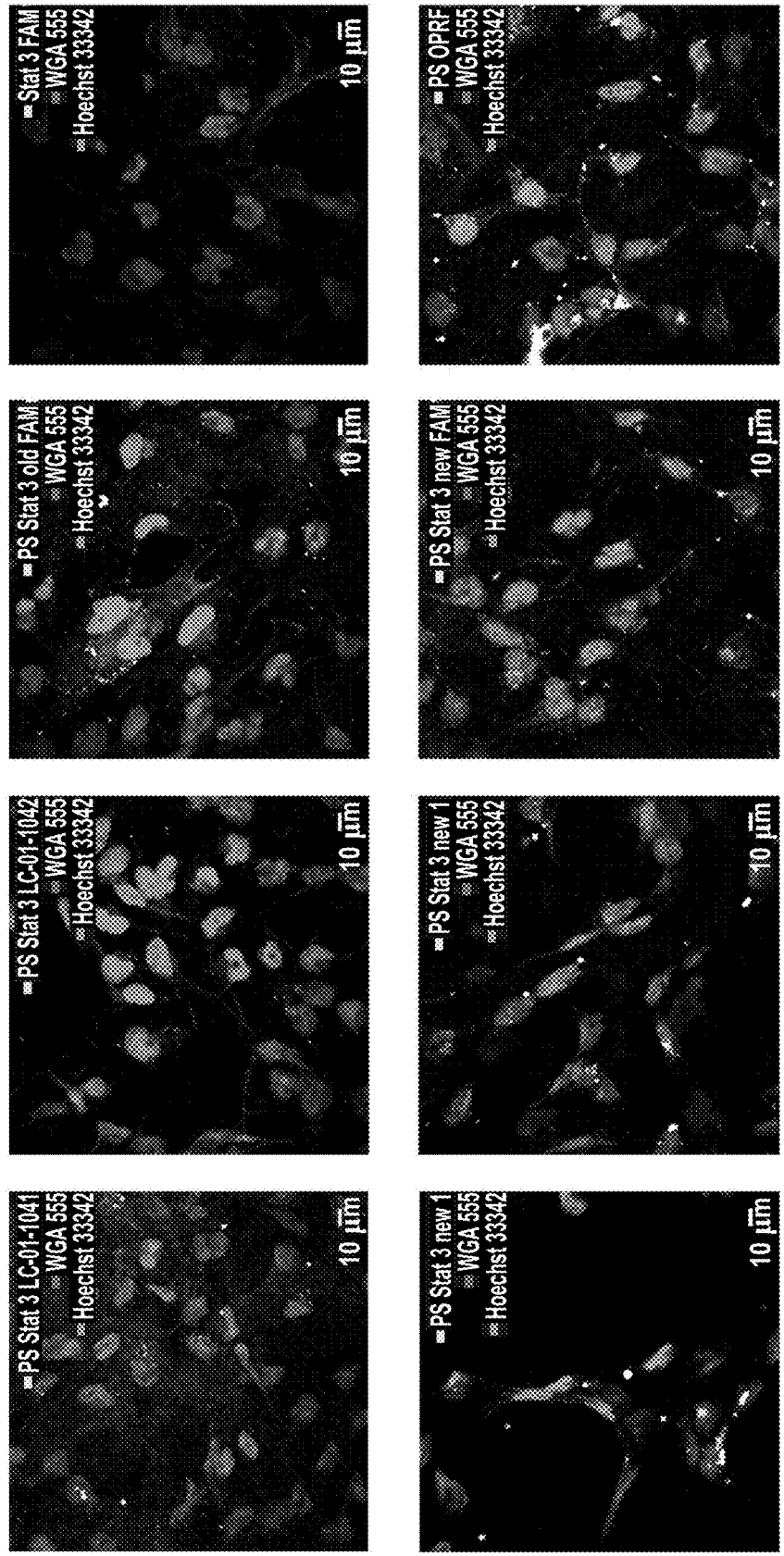
FIG. 15E is a confocal microscopy image of compound 901 internalization in U251 cells.

15E, red fluorescence indicates the plasma membrane, blue fluorescence indicates the nuclei and green florescence indicates compound 901. FIG. 15C shows the results of the same experiments described in 15A, but in MCF-10A human normal breast epithelial cells with additional increasing serum concentrations. FIG. 15D shows the microscopic images of MDA-MB-468 human breast cancer cells treated with compound 901a at 5 ug/mL and 10 ug/mL.

In a separate experiment, it was shown that compound 901a was internalized into cells and redistributed around the nucleus upon STAT3 activation. MCF-10A cells (5,000 cells/well) were incubated with no serum or 20% human serum, overnight, to induce STAT3 activation. 10 ug/ml of compound 901a was added to the cells for 2 hours. Intracellular antibodies were visualized by an EVOS microscope of cells stained with anti-human IgG conjugated to Alexa546.

Figure 16A:
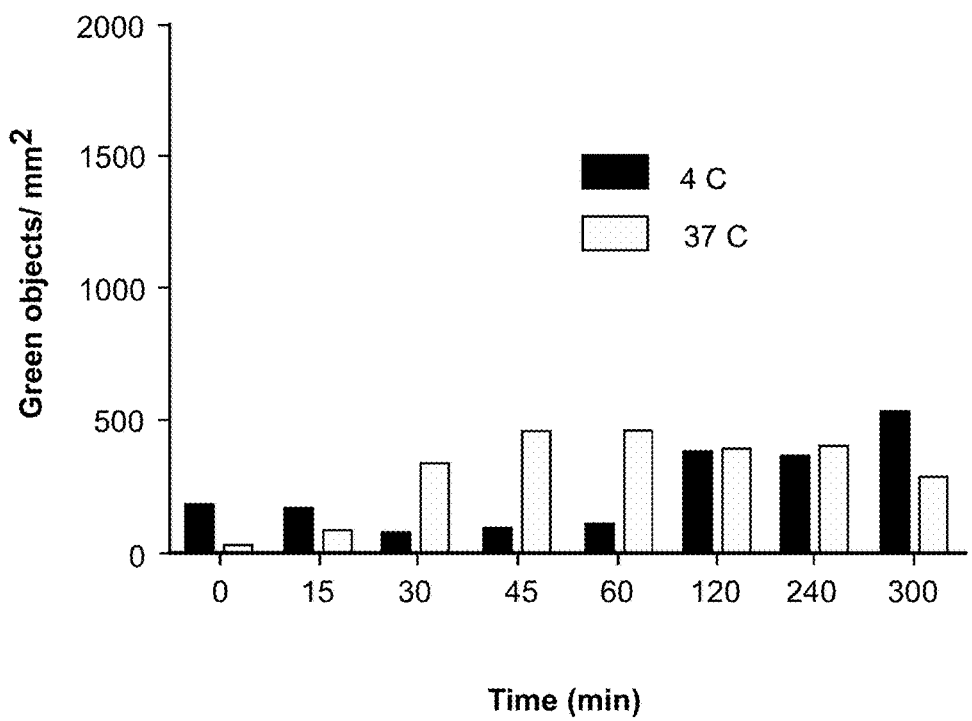
FIG. 16A is a graph that shows the effect of temperature on internalization of compound 901a in U251 cells.
Figure 16B:
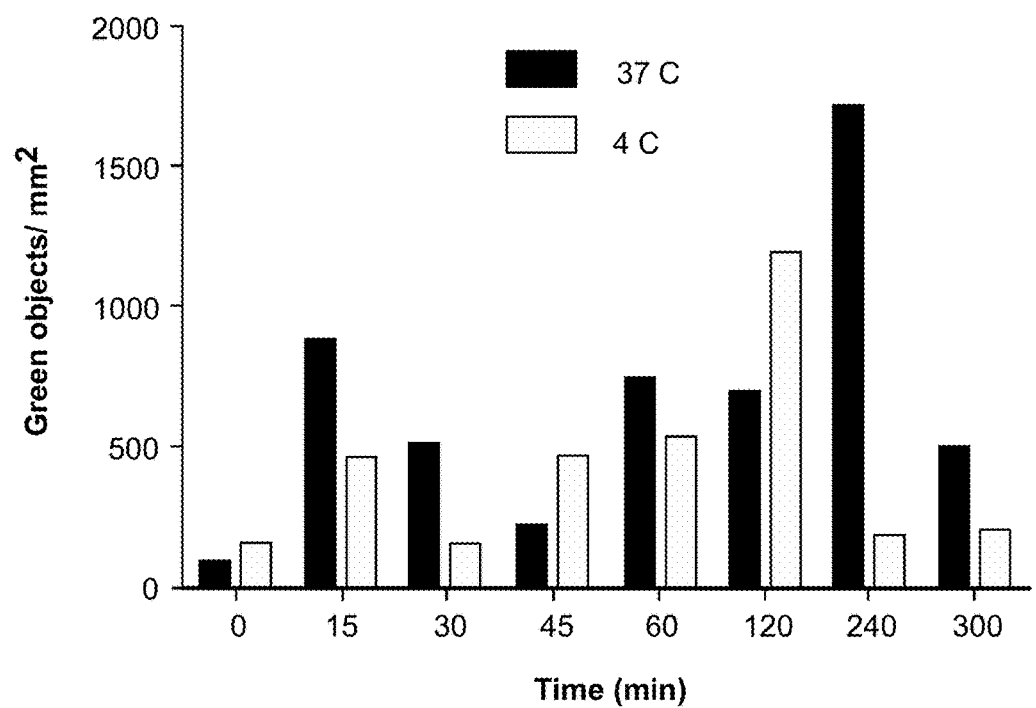
FIG. 16B is a graph that shows the effect of temperature on internalization of compound 901a in MDA-MB-468 cells.

FIG. 16A and FIG. 16B show the effect of temperature of internalization of compound 901a. FIG. 16A shows the effect of temperature on internalization of compound 901a in U251 cells. U251 cells were incubated with compound 901a with an Alexa flour NHS 488 label at a concentration of 10 ug/ml. The results are shown as the number of green objects, corresponding to the number of cells that internalized the antibody conjugate, over time, at 4° C. and 37° C. FIG. 16B is a graph that shows the effect of temperature on internalization of compound 901a in MDA-MB-468 cells. MDA-MB-468 cells were incubated with compound 901a with an Alexa flour NHS 488 label at a concentration of 10 ug/ml. The results are shown as the number of green objects, corresponding to the number of cells that internalized compound 901a, over time, at 4° C. and 37° C.

Figure 17A:
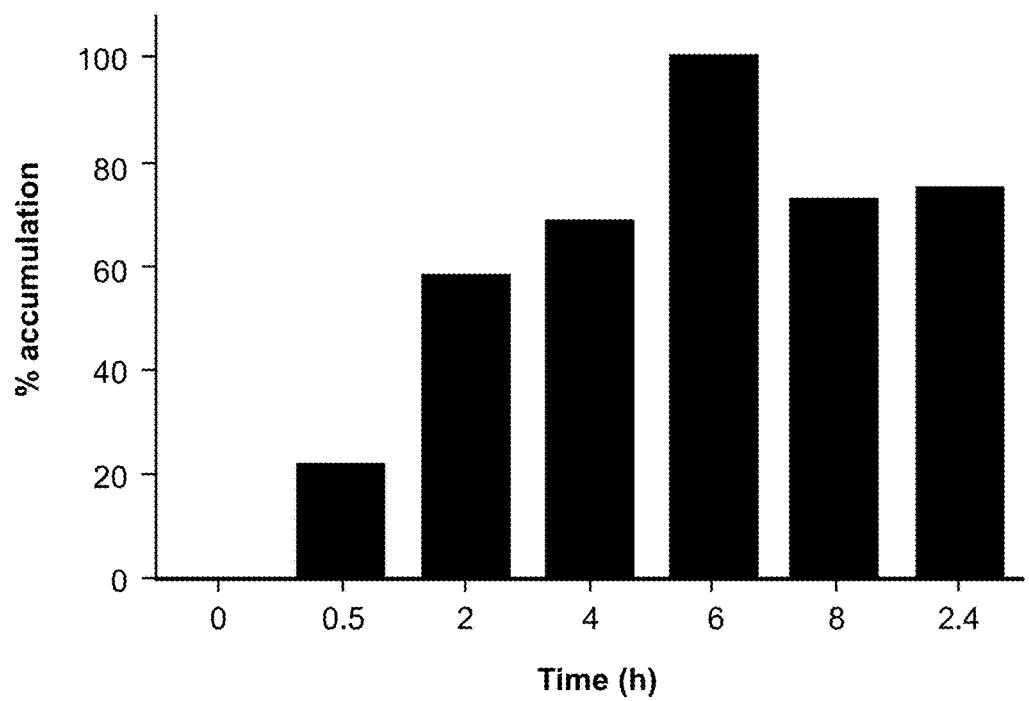
FIG. 17A is a graph that shows the results of a time course analysis that was carried out to determine the cellular uptake of compound 901a in MDA-MB-480 cells.
Figure 17B:
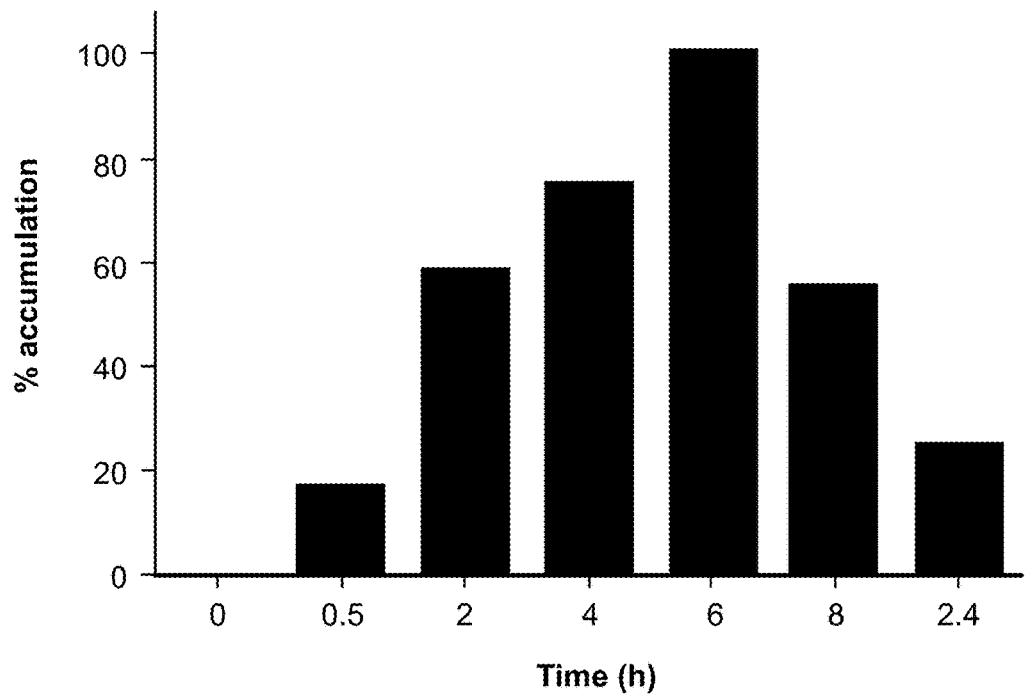
FIG. 17B is a graph that shows the results of a time course analysis that was carried out to determine the cellular uptake of compound 901a in MCF-10A cells.

A time course analysis was also carried out to determine the cellular uptake of compound 901a. MDA-MB-480 (STAT3 high) and MCF-10A (STAT3 low) cells were seeded in 96 well plates at a concentration of 5000 cells/well. Twenty four hours later, 20 ug/ml of compound 901a labeled with Alexa 488 were added to the cells for the following durations: 0.5 hours, 2 hours, 4 hours, 6 hours, 8 hours and 24 hours. Cells were then fixed and imaged using Incucyte. FIG. 17A shows compound 901a accumulated in MDA-MB-436 cells. FIG. 17B shows compound 901a accumulated in MCF-10A cells. In both cell lines, accumulation appeared to peak at 6 hours.

Figure 18:
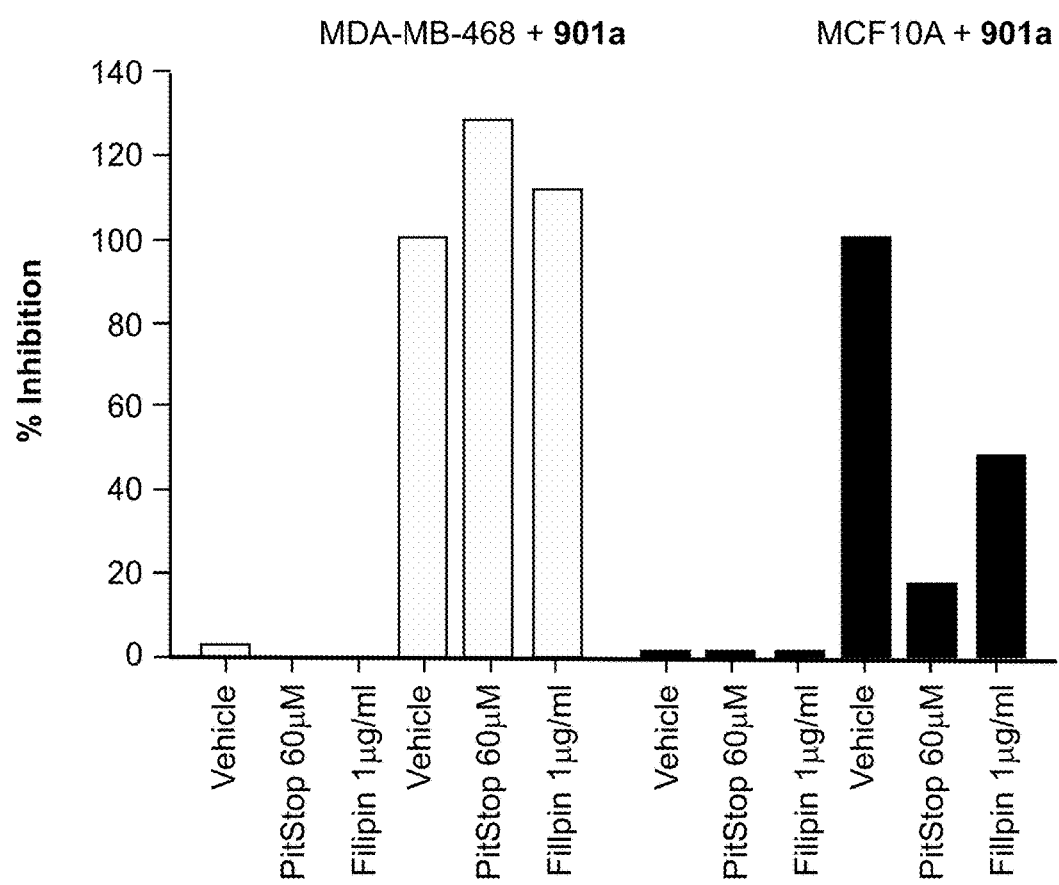
FIG. 18 is a graph that shows that compound 901a enters MDA-MB-438 (STAT3 high) tumor cells using endocytosis independent mechanism.

Next, the mechanism of how compound 901a enters the cell was examined MDA-MB-468 (STAT3 high) and MCF-10A (STAT3 low) cells were seeded at 5,000 cells per well in a 96 well plate overnight. Cells were treated with the clathrin inhibitor Pitstop2 (60 uM) or the caveolin inhibitor filipin (1 ug/ml) for 30 minutes. 20 ug/ml of compound 901a-Alexa488 antibody was added for another 30 minutes. Vehicle alone was used as a control. Cells were then fixed and imaged with Incucyte. FIG. 18 shows that compound 901a entered MDA-MB-438 (STAT3 high) tumor cells using endocytosis independent mechanisms.

Figure 19:
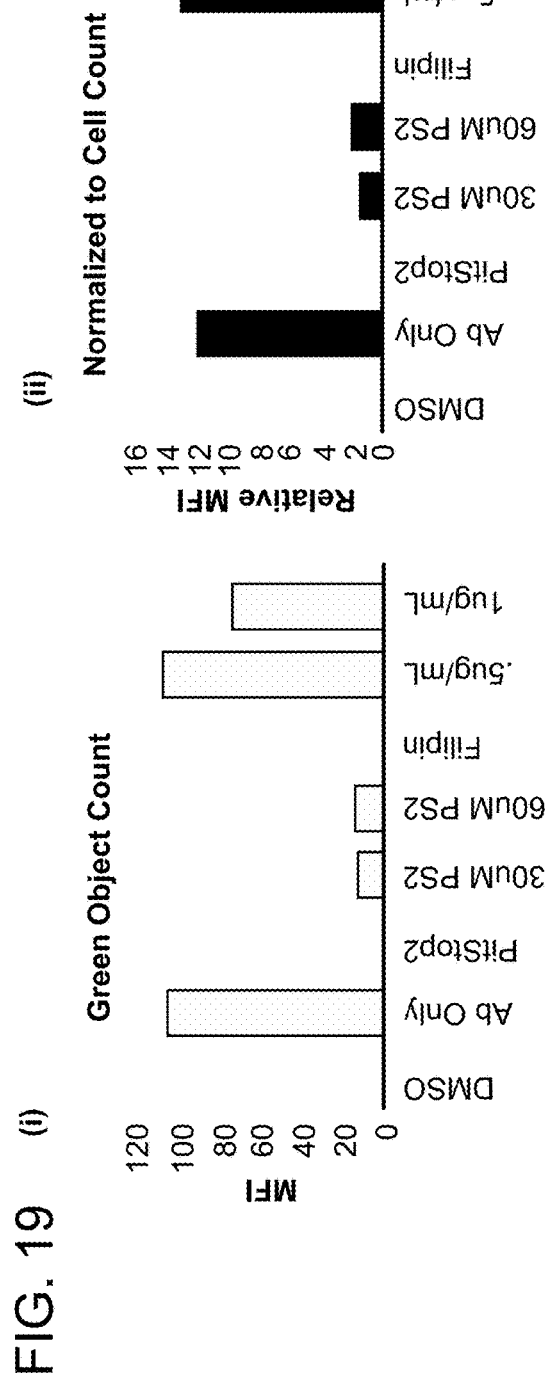
FIG. 19 is a graph that shows the effects of the clathrin inhibitor Pitstop2 (PS2; 30 uM or 60 uM) or the caveolin inhibitor filipin (0.5 ug/ml or 1.0 ug/ml) on compound 901a mediated uptake in MCF-10A cells.
Figure 20:
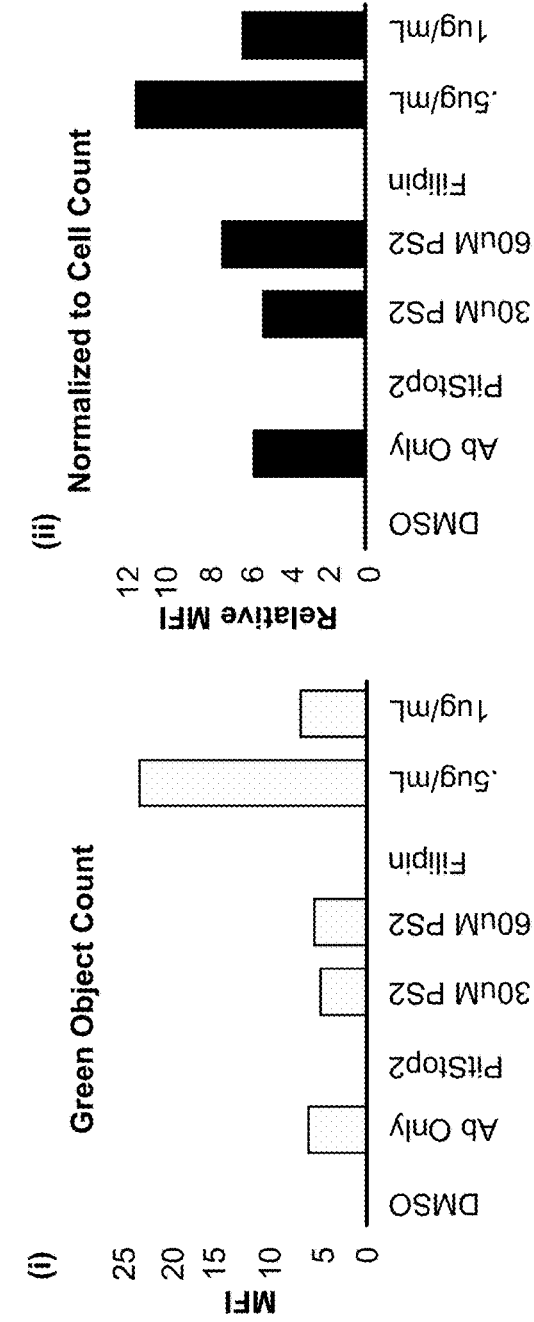
FIG. 20 is a graph that shows the results of the same experiments done in FIG. 19, in MDA-MB-468 breast carcinoma cells.

Caveolin and clathrin-dependent compound 901a mediated uptake was examined in MCF-10A cells. Clathrin-mediated endocytosis is mediated by small vesicles that have a morphologically characteristic coat made up of a complex of proteins that are mainly associated with the cytosolic protein clathrin. Caveolae are the most common reported non-clathrin-coated plasma membrane buds, which exist on the surface of many, but not all cell types. They consist of the cholesterol-binding protein caveolin (Vip21) with a bilayer enriched in cholesterol and glycolipids. Both clathrin mediated endocytosis and caveolae transport extracellular molecules into the cell. 5,000 cells were seeded per well in a 96 well plate, overnight. Cells were pretreated with the clathrin inhibitor Pitstop2 (30 uM or 60 uM) or the caveolin inhibitor filipin (0.5 ug/ml or 1.0 ug/ml) for 30 minutes. 20 ug/ml of compound 901a-Alexa488 antibody was added for another 30 minutes. Cells were fixed and imaged with IncuCyte. DMSO and antibody only were used as controls. As shown in FIG. 19 panel (i), treatment with the clathrin inhibitor PS2 at concentrations of 30 uM and 60 uM inhibited compound 901a uptake, while treatment with the caveolin inhibitor, filipin, had little effect at a concentration of 0.5 ug/ml, and a greater effect at 1.0 ug/ml. FIG. 19 panel (ii) shows the data normalized to cell count. FIG. 20 shows the results of the same experiments performed in MDA-MB-468 (STAT3 high) cells.

Temperature Dependence of Compound 901 Entry into Cells

Figure 21A:
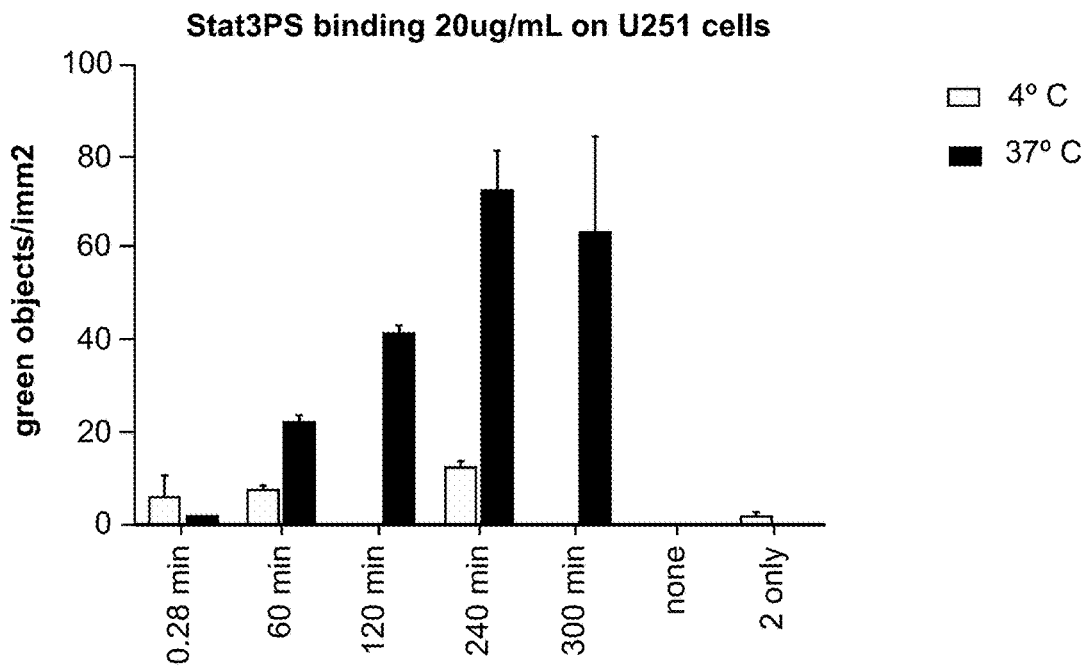
FIG. 21A is a graph that shows the results of experiments that were carried out to determine if the entrance of compound 901a was dependent on temperature.
Figure 21B:
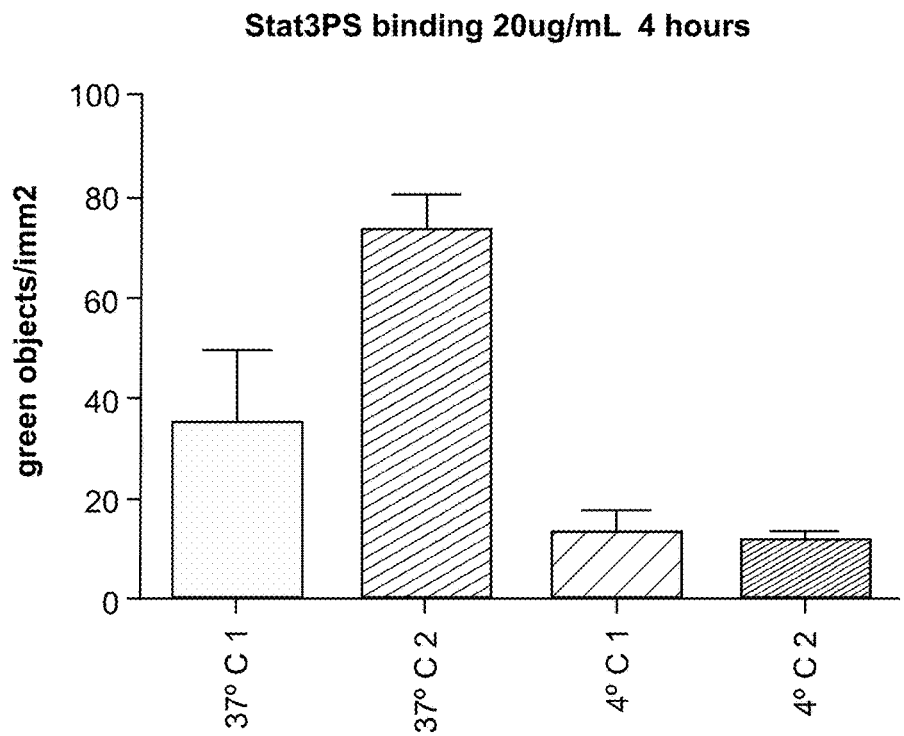
FIG. 21B is a graph that shows the results of experiments that were carried out to determine if the entrance of compound 901a was dependent on temperature.

Experiments were carried out to determine if the entrance of compound 901a was dependent on temperature. 10,000 U251 cells were seeded. Compound 901a was incubated at 37° C. or 4° C., at a concentration of 20 ug/mL for selected time, then fixed in 4% PFA. Cells were permeabilized with 0.1% tritonX, and then locked with 3% BSA, and treated with 1:250 Alexa 488 GAH IgG. Cells were then washed and imaged. The results are shown in FIG. 21A and FIG. 21B. FIG. 21A shows an inhibition of compound 901a at 4° C., where, as time increased, the green object count did not increase. For compound 901a at 37° C., the green object count increased until 240 min. After 240 min there was either a taper or a plateau. FIG. 21B compares the 240 minute time point from the experiment described in FIG. 21A ("37° C. 1" and "4° C. 1") with a second experiment at the 240 minute time point ("37° C. 2" and "4° C. 2")). The signal at 4 C remained about the same, but a large boost in 37° C. signal was observed.

Blocking IL-26-STAT3 Pathway in COLO205

Figure 22:
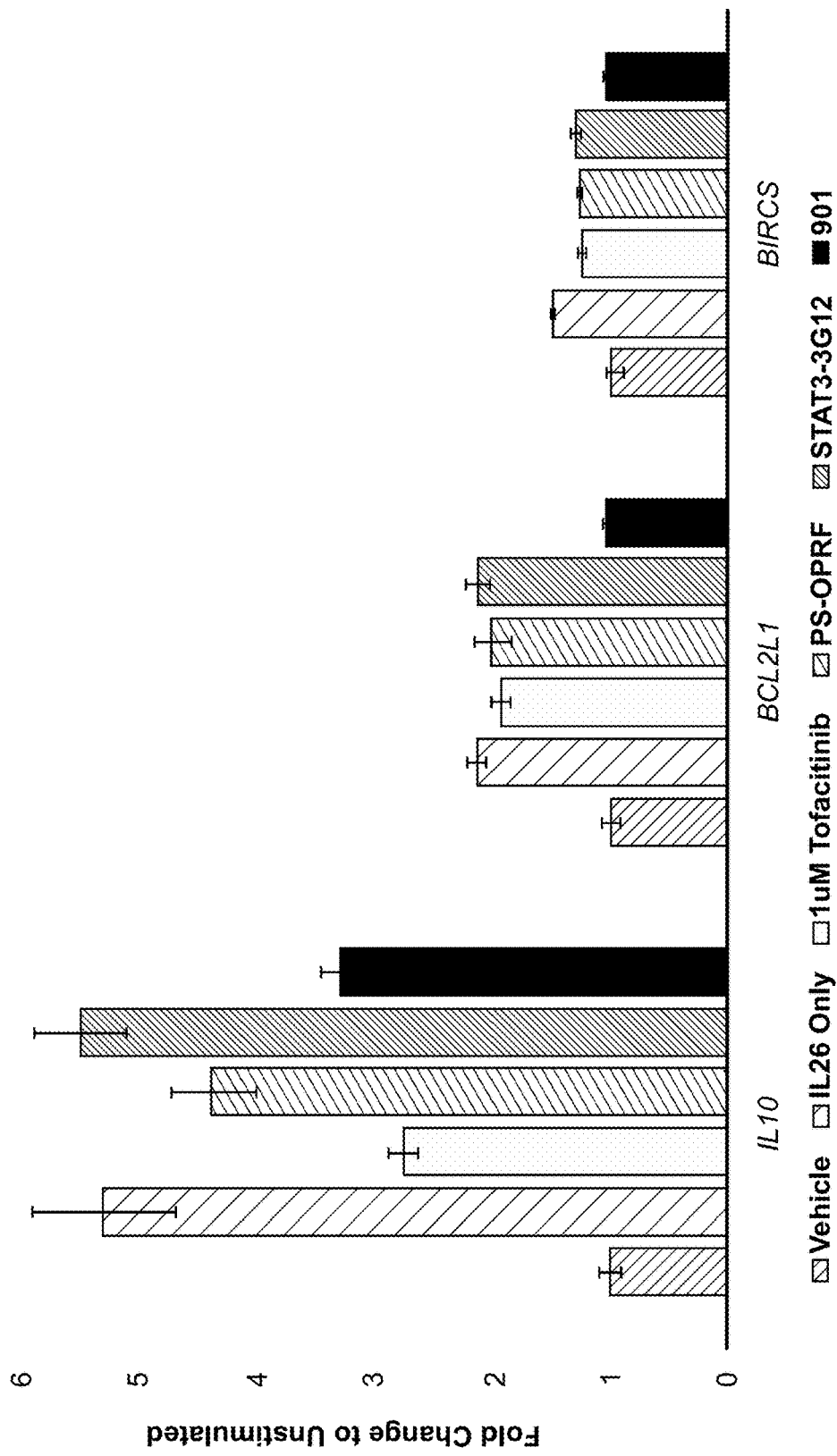
FIG. 22 is a graph that shows the results of experiments that were carried out to test whether anti-STAT3 antibody conjugates can block mRNA expression of IL-26 induced IL-10 cytokine and anti-apoptotic genes BCL2L1 and BIRC5.
Figure 23:
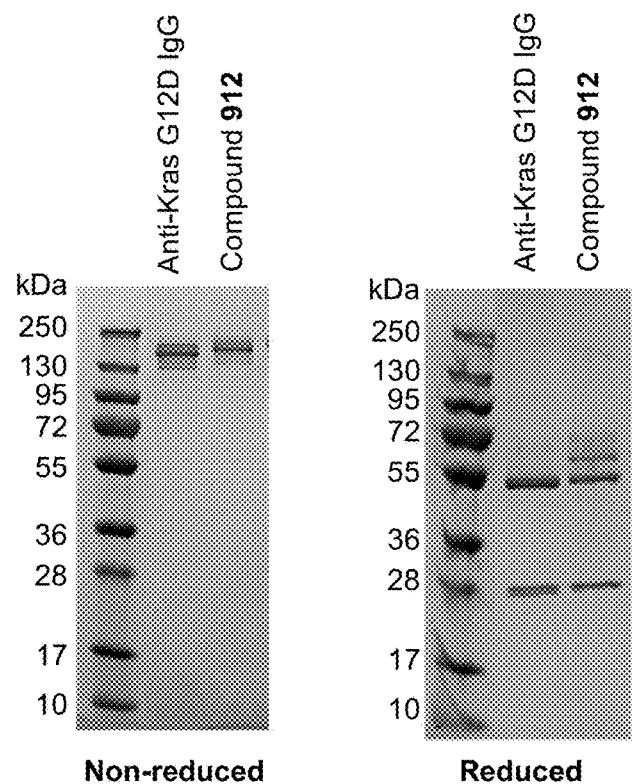
FIG. 23 shows the SDS-PAGE characterization of compound 912, a compound of Formula I where $A_T$ is anti-KRAS.
Figure 24:
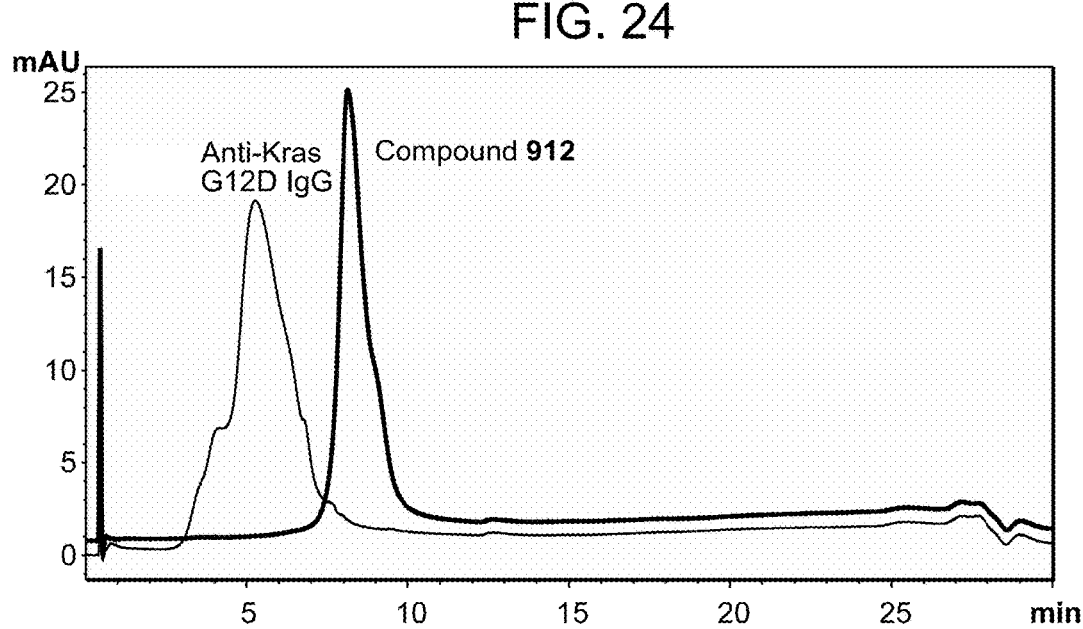
FIG. 24 shows the HPLC-HIC (hydrophobic interaction chromatograpy) of anti-KRAS antibody and compound 912.
Figure 25:
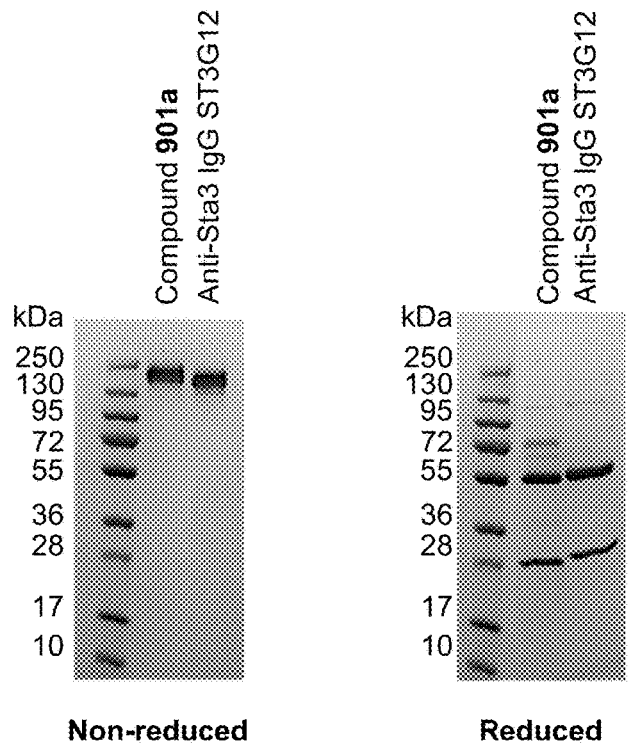
FIG. 25 shows the SDS-PAGE characterization of compound 901a, a compound of Formula I where $A_T$ is anti-Stat3 IgG ST3G12.
Figure 26:
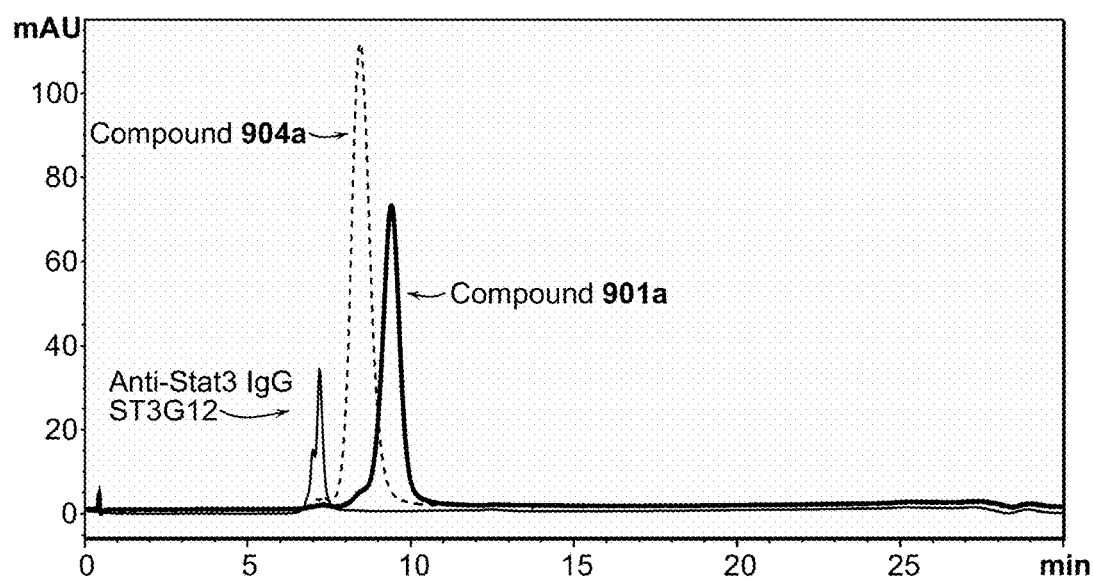
Figure 27:
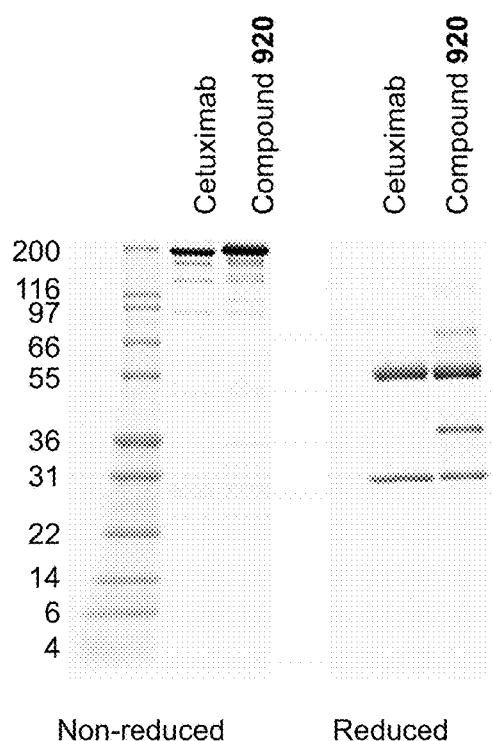
FIG. 27 shows the SDS-PAGE characterization of compound 920, a compound of Formula I where $A_T$ is Cetuximab.
Figure 28:
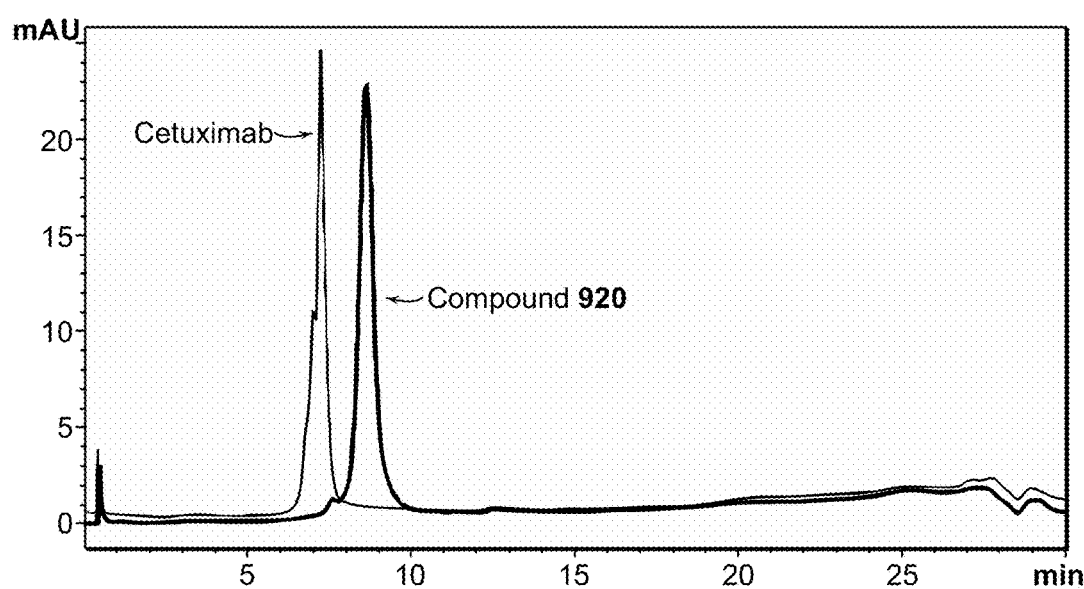
FIG. 28 shows the HPLC-HIC (hydrophobic interaction chromatograpy) of anti-Cetuximab and compound 920.

Experiments were carried out to test whether compound 901a can block expression of IL-26 induced IL-10 cytokine and anti-apoptotic genes BCL2L1 and BIRC5. Briefly, COLO205 cells were seeded at 100 k/well in 12 well plate. Cells were pre-incubated with 50 ug/mL PS-OPRF (an antibody to the OPRF bacterial protein, conjugated to PS, used as a control), unmodified ST3G12, compound 901a, or 1 uM JAK inhibitor Tofacitinib for 90 minutes at 37° C. Cells were stimulated overnight with 2.5 ug/mL IL-26 (0.1% Human serum carrier protein). After overnight stimulation, RNA was extracted from cells and reverse transcribed to cDNA followed by rtPCR. The results are shown in FIG. 22. As shown in FIG. 22, IL-26 stimulated expression of IL-10, BCL2L1 (BCL-XL), and BIRC5 (Survivin), which was significantly reversed by compound 901a.

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound having the Formula I:

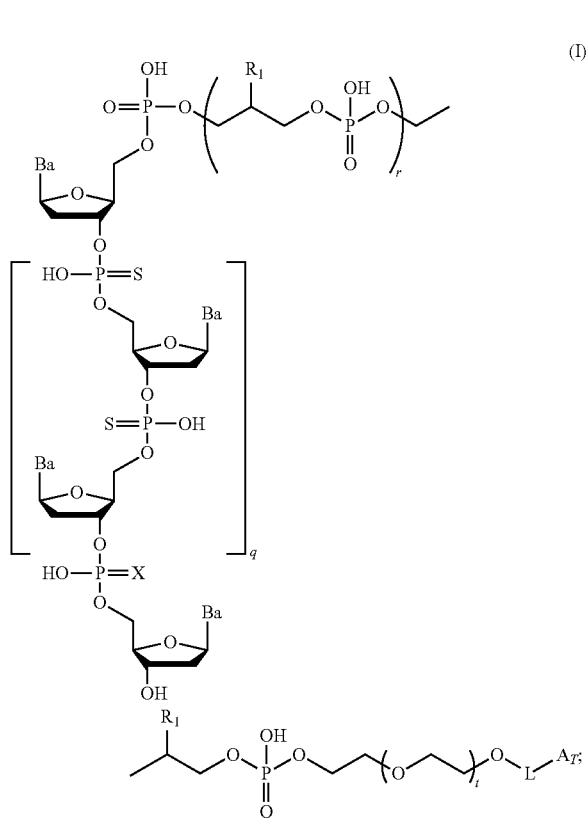

wherein,
each Ba is independently selected from adenine (A), guanine (G), cytosine (C), and thymine (T);
X is O or S;
each $R_1$ is independently selected from hydrogen and $(C_1-C_6)$alkyl substituted with a fluorophore;
q is an integer from 12 to 35;
r is an integer from 1 to 10;
t is an integer from 1 to 10;
L is —$CH_2$—$R^2$—*;
$R^2$ is —$(C_1-C_6)$alkyl substituted with 1 or 2 groups selected from —C(=O)$NR^a$, —$NR^aC$(=O)$R^b$, —$NR^aC$(=O)$R^d$, =$NOR^e$, —$NR^a$, —$NR^aR^b$, —$OR^b$, —S(O)$_kR^b$, —$NR^aS$(O)$_2R^b$, —S(O)$_2NR^aR^b$, —S(O)$_2$$NR^a$, —C(=O)$OR^b$, —OC(=O)$OR^b$, —OC(=O)$R^b$, —C(=O)$NR^aR^b$, —$NR^aC$(=O)$R^b$, —$NR^aC$(=O)$OR^b$, —OC(=O)$NR^aR^b$, phenyl, —OC(=O)$NR^a$, —$NR^aC$(=O)$NR^aR^b$, —$NR^aC$(=O)$NR^a$, —$NR^a$(C=S)$NR^aR^b$, —$NR^a$(C=S)$NR^a$, and —C(=O)$R^b$;
k is 0, 1, or 2;
each $R^a$ is independently hydrogen or $(C_1-C_6)$alkyl optionally substituted with $R^f$;
each $R^b$ is independently $(C_1-C_6)$alkyl optionally substituted with $R^f$ or —C(=O)$R^f$;
$R^d$ is —[$(C_1-C_6)$alkyl-O—$(C_1-C_6)$alkyl]$_v$C(=O)NH;
$R^e$ is —[$(C_1-C_6)$alkyl-O—$(C_1-C_6)$alkyl]$_p$C(=O);

each $R^f$ is independently

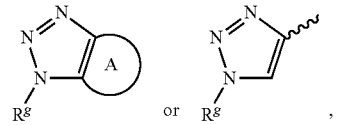

wherein the wavy bond indicates the point of attachment to the $(C_1-C_6)$alkyl defined by $R^a$, or the $(C_1-C_6)$alkyl or carbonyl each defined by $R^b$;
$R^g$ is $(C_1-C_6)$alkyl or —[$(C_1-C_6)$alkyl-O—$(C_1-C_6)$alkyl]$_w$C(=O)NH;
ring A is

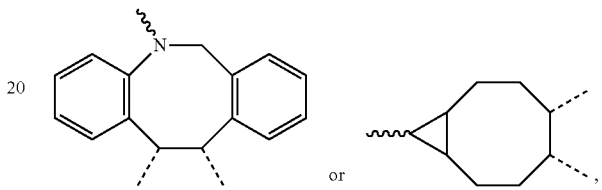

wherein the dashed bonds indicate the points of attachment to the triazolyl of $R^f$, and the wavy bond indicates the point of attachment to the $(C_1-C_6)$alkyl defined by $R^a$, or the $(C_1-C_6)$alkyl or carbonyl each defined by $R^b$;
p is an integer from 1 to 10;
v is an integer from 1 to 10;
w is an integer from 2 to 12;
* indicates the point of attachment to $A_T$; and
$A_T$ is an antibody.

2. The compound of claim 1, wherein $R^2$ is —$(C_1-C_6)$alkyl substituted with —C(=O)$NR^a$, —$NR^aC$(=O)$R^b$, —$NR^aC$(=O)$R^d$, =$NOR^e$, —$NR^a$, —$NR^aR^b$, —$OR^b$, —S(O)$_kR^b$, —$NR^aS$(O)$_2R^b$, —S(O)$_2NR^aR^b$, —S(O)$_2NR^a$, —C(=O)$OR^b$, —OC(=O)$OR^b$, —OC(=O)$R^b$, —C(=O)$NR^aR^b$, —$NR^aC$(=O)$R^b$, —$NR^aC$(=O)$OR^b$, —OC(=O)$NR^aR^b$, —OC(=O)$NR^a$, —$NR^aC$(=O)$NR^aR^b$, —$NR^aC$(=O)$NR^a$, —$NR^a$(C=S)$NR^aR^b$, —$NR^a$(C=S)$NR^a$, or —C(=O)$R^b$.

3. The compound of claim 1, wherein $R^2$ is —$(C_1-C_6)$alkyl substituted with —C(=O)$NR^a$, —$NR^aC$(=O)$R^b$, —$NR^aC$(=O)$R^d$, =$NOR^e$, —$NR^a$, —$R^aR^b$, —$OR^b$, —S(O)$_2NR^aR^b$, —S(O)$_2NR^a$, —C(=O)$OR^b$, —C(=O)$NR^aR^b$, —$NR^aC$(=O)$R^b$, —$NR^aC$(=O)$OR^b$, —$NR^aC$(=O)$NR^aR^b$, —$NR^aC$(=O)$NR^a$, or —C(=O)$R^b$.

4. The compound of claim 1, wherein $R_2$ is —$(C_1-C_6)$alkyl-$NR^aC$(=O)$R^d$, —$(C_1-C_6)$alkyl-$NR^aC$(=O)$R^b$, or —$(C_1-C_6)$alkyl(=NO)$R^e$.

5. The compound of claim 1, wherein $R^d$ is —[$(C_1-C_4)$alkyl-O—$(C_1-C_4)$alkyl]$_v$C(=O)NH.

6. The compound of claim 1, wherein $R^e$ is —[$(C_1-C_4)$alkyl-O—$(C_1-C_4)$alkyl]$_p$C(=O).

7. The compound of claim 1, wherein $R^g$ is —[$(C_1-C_4)$alkyl-O—$(C_1-C_4)$alkyl]$_w$C(=O)NH.

8. The compound of claim 1, wherein each $R^a$ is independently selected from hydrogen and $(C_1-C_6)$alkyl.

9. The compound of claim 1, wherein $R^b$ is $(C_1-C_6)$alkyl substituted with $R^f$ or —C(=O)$R^f$.

10. The compound of claim 1, wherein p is an integer from 1 to 6.

11. The compound of claim 1, wherein v is an integer from 1 to 6.

12. The compound of claim 1, wherein w is an integer from 2 to 8.

13. The compound of claim 1, wherein $R^f$ is
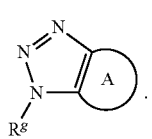
14. The compound of claim 1, wherein ring A is
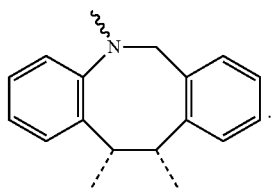
15. The compound of claim 1, wherein the fluorophore, if present, is fluorescein.
16. The compound of claim 1, wherein the compound is of the Formula IIb:
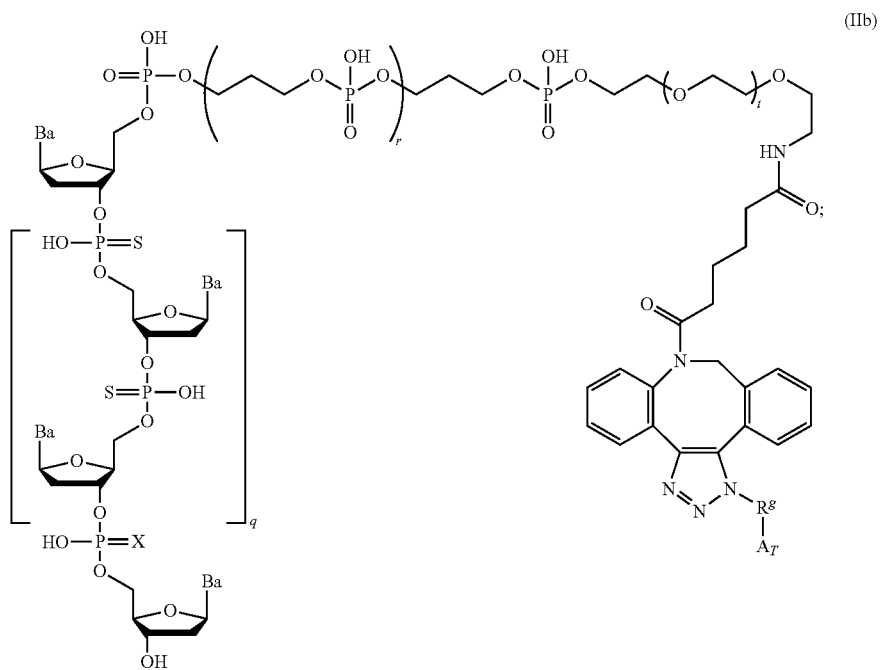
or a pharmaceutically acceptable salt thereof.

17. The compound of claim 1, wherein the compound is of the Formula IIIa:

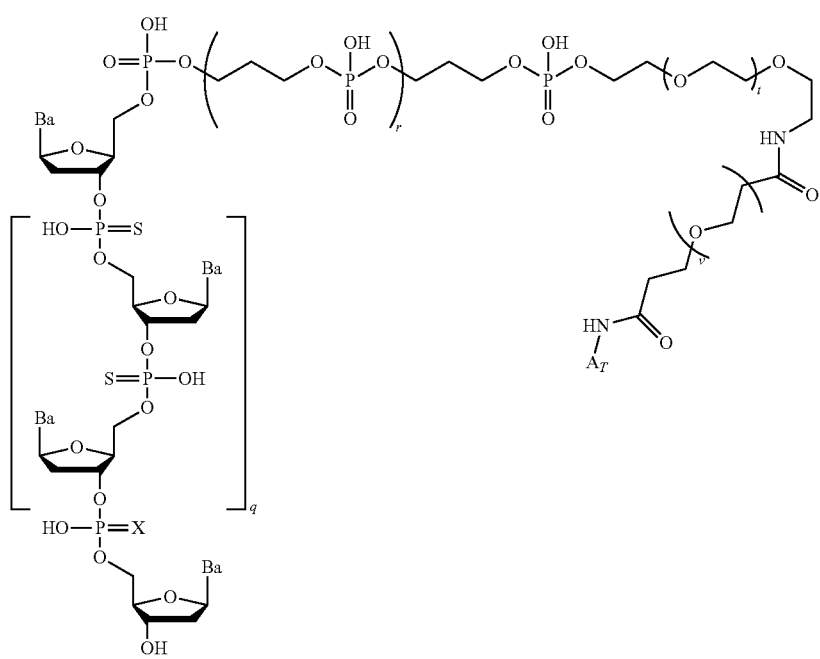

or a pharmaceutically acceptable salt thereof.

18. The compound of any one of claims 1 to 10, wherein the compound is of the Formula IVa:

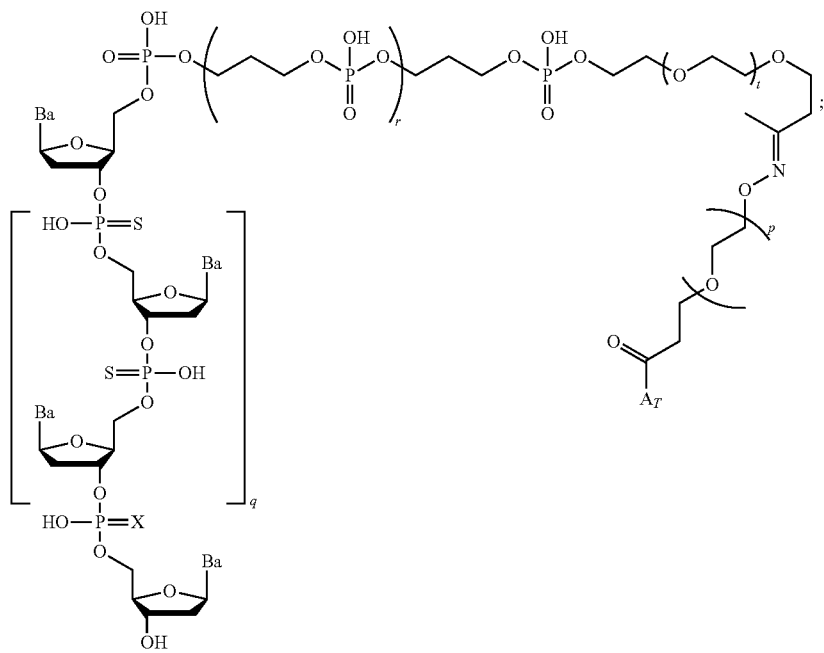

or a pharmaceutically acceptable salt thereof.

19. The compound of claim 1, wherein X is S.

20. The compound of claim 1, wherein r is an integer from 3 to 5.

21. The compound of claim 1, wherein t is an integer from 2 to 4.

22. The compound of claim 1, wherein q is an integer from 15 to 25.

23. The compound of claim 1, wherein the thiophosphate oligonucleotide sequence beginning at the 3' end is TCCAT-GAGCTTCCTGATGCT (SEQ ID NO.: 5).

24. The compound of claim 1, wherein $A_T$ is an IgG antibody.

25. The compound of claim 1, wherein $A_T$ is anti-STAT3, panitumumab, CTLA4, or VEGFR2.

26. The compound of claim 1, wherein the compound is
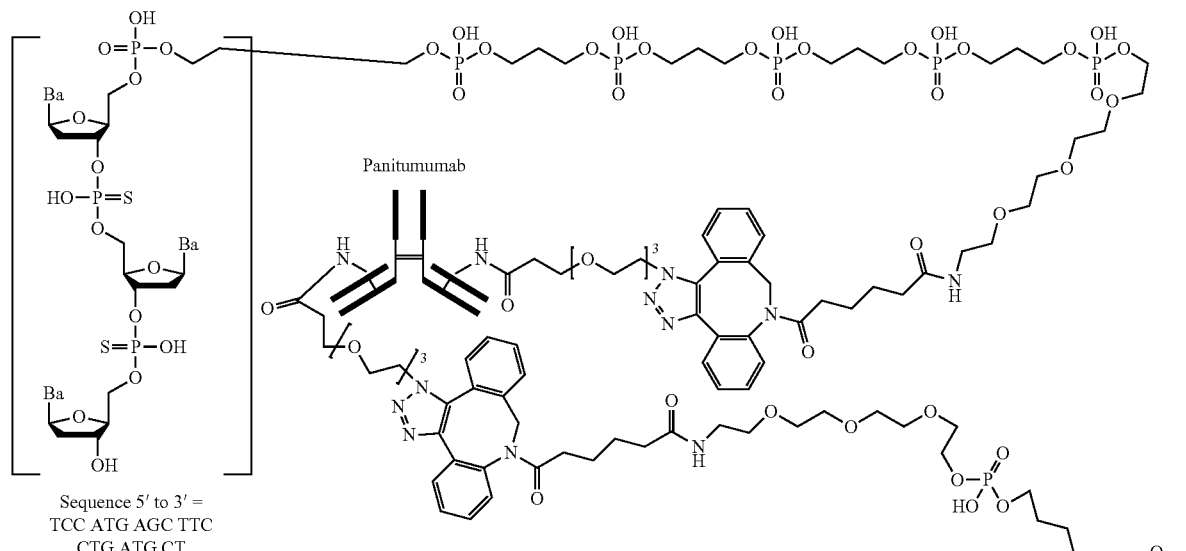
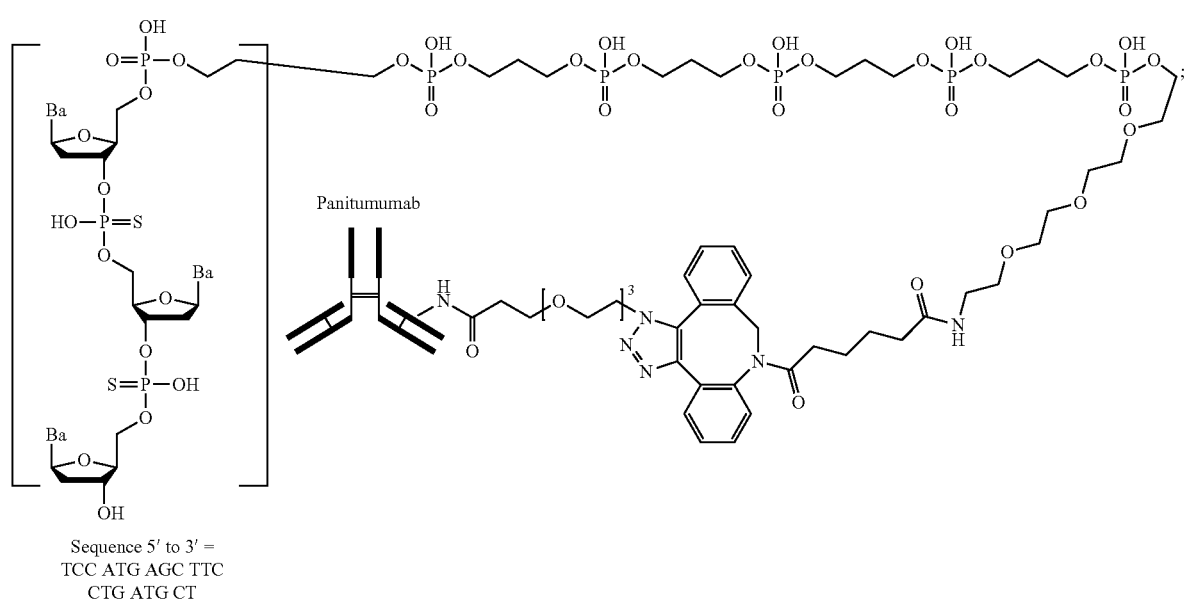

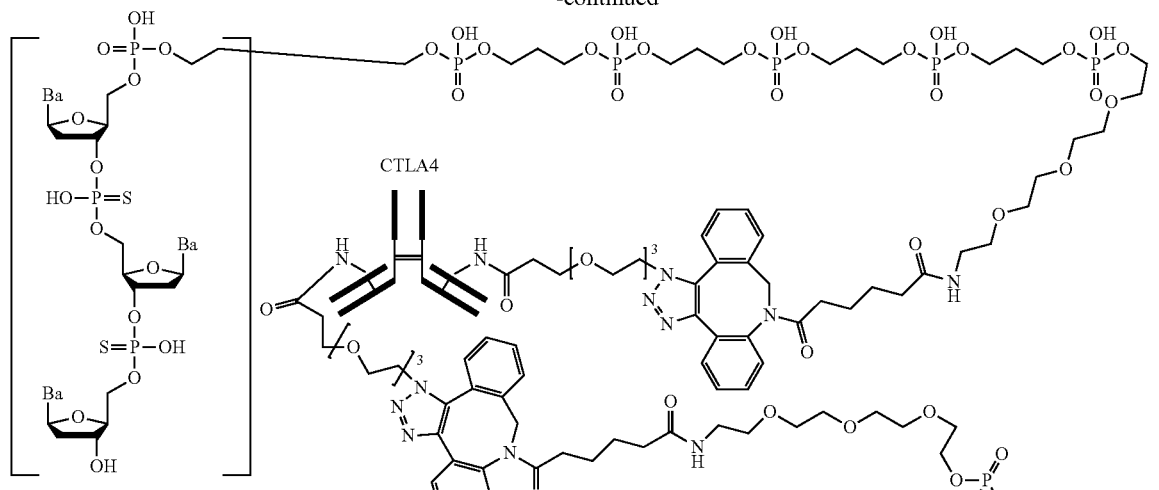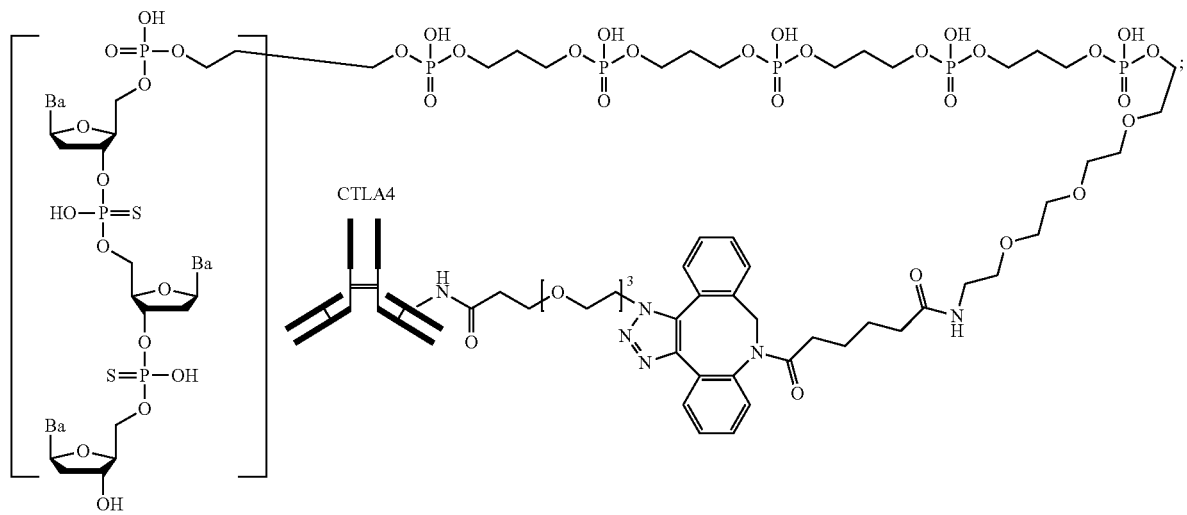

101 102
-continued
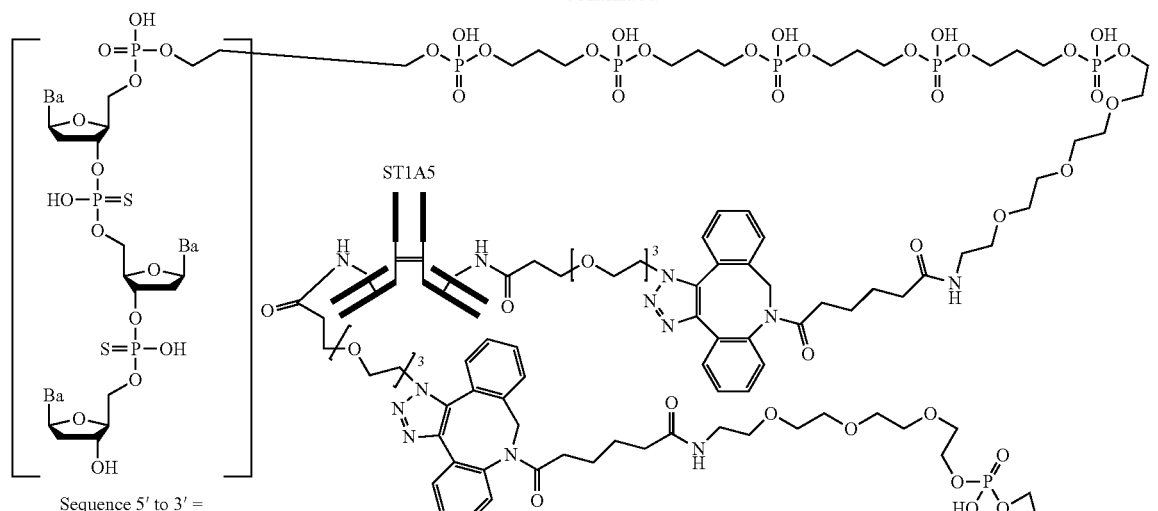
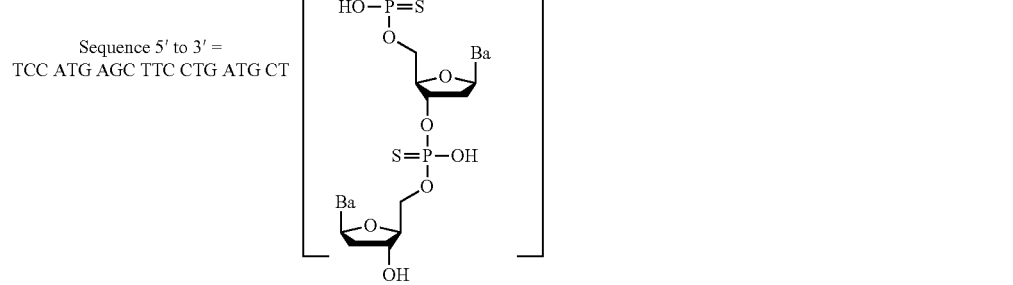
Sequence 5' to 3' =
TCC ATG AGC TTC CTG ATG CT
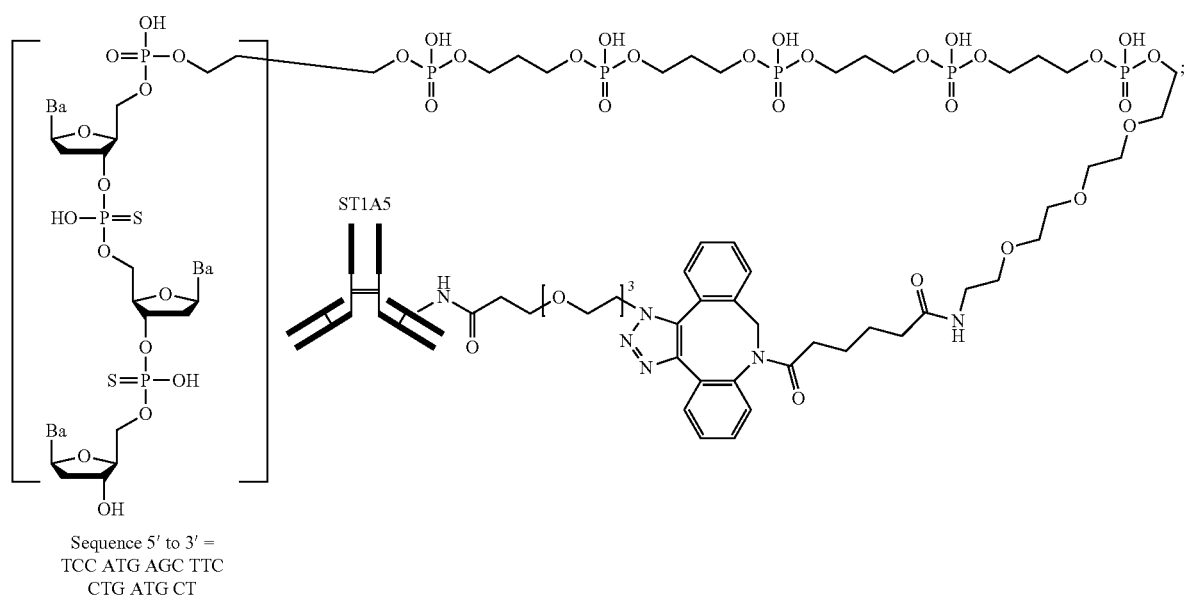
Sequence 5' to 3' =
TCC ATG AGC TTC CTG ATG CT -continued
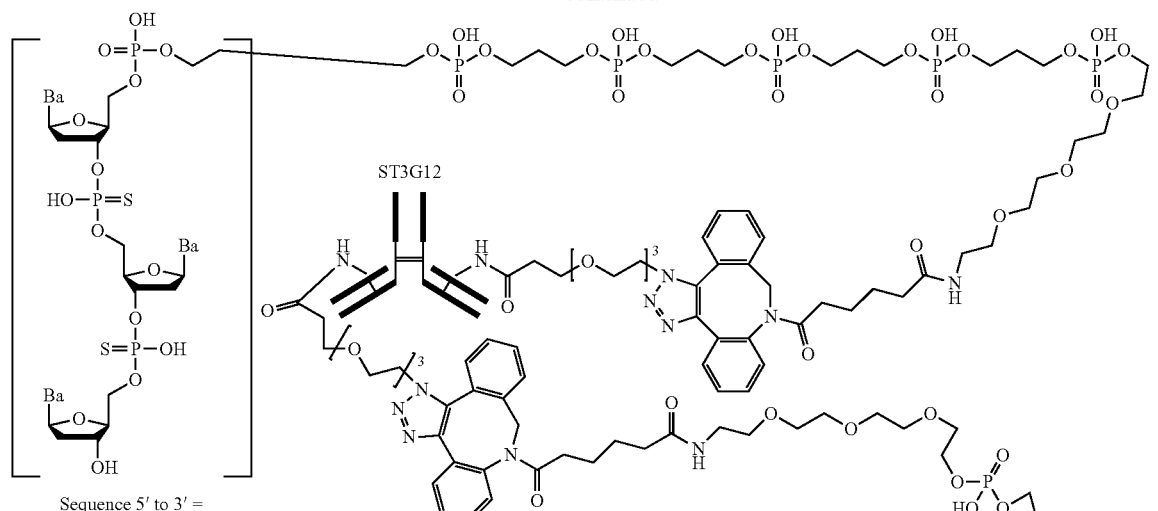
Sequence 5' to 3' =
TCC ATG AGC TTC CTG ATG CT
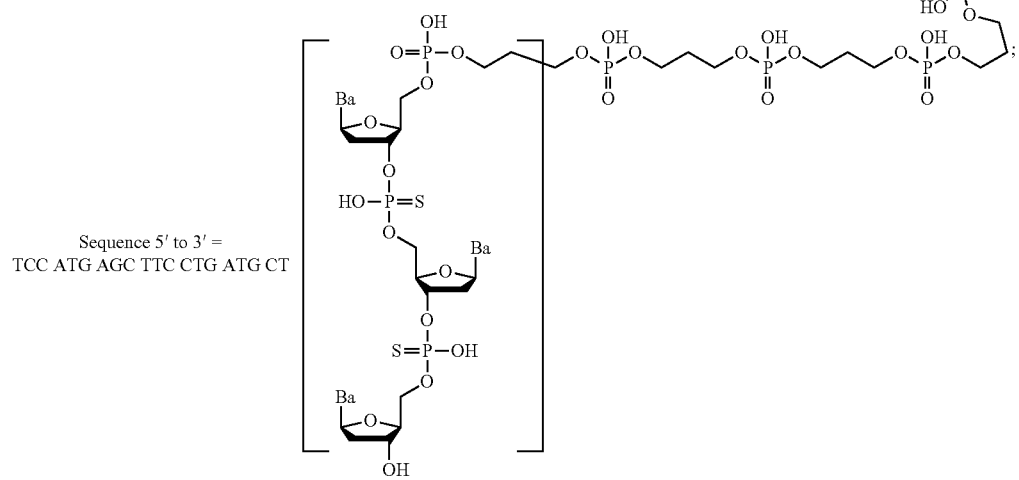
Sequence 5' to 3' =
TCC ATG AGC TTC CTG ATG CT
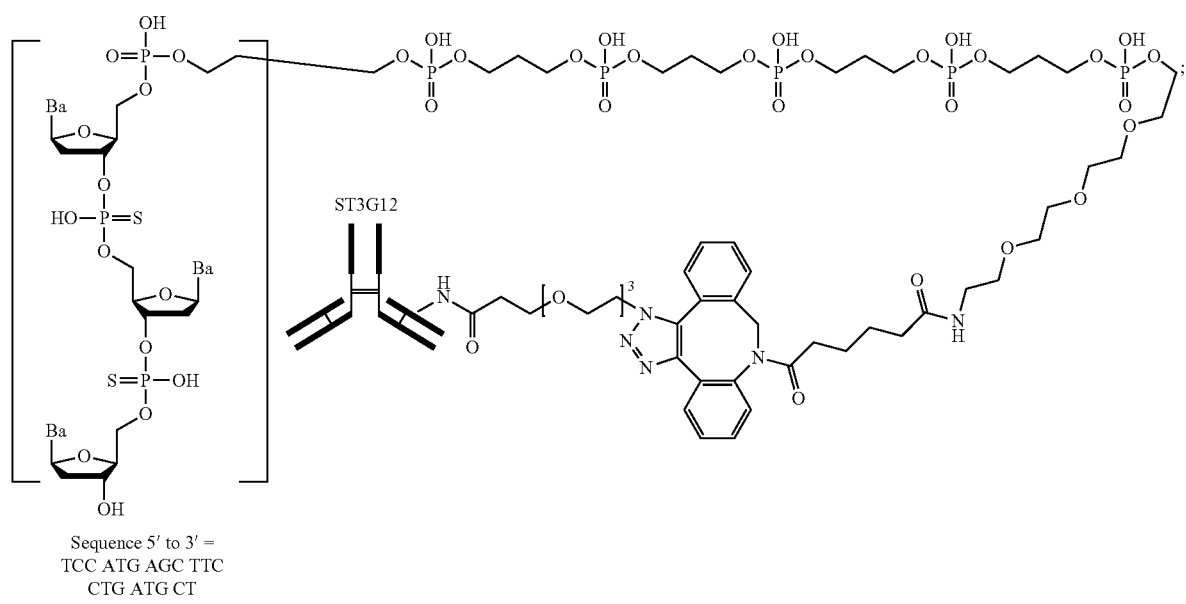
Sequence 5' to 3' =
TCC ATG AGC TTC CTG ATG CT 105
-continued
106
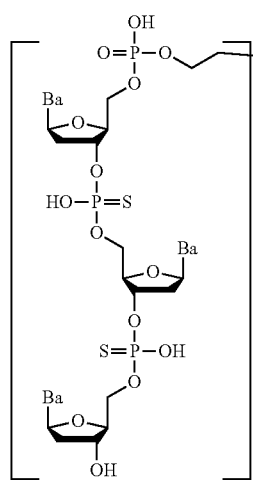
Sequence 5' to 3' =
TCC ATG AGC TTC
CTG ATG CT
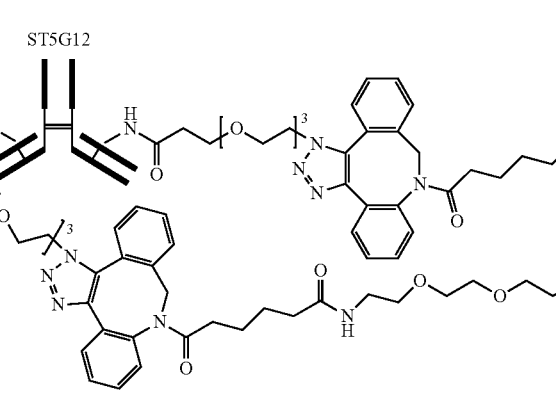
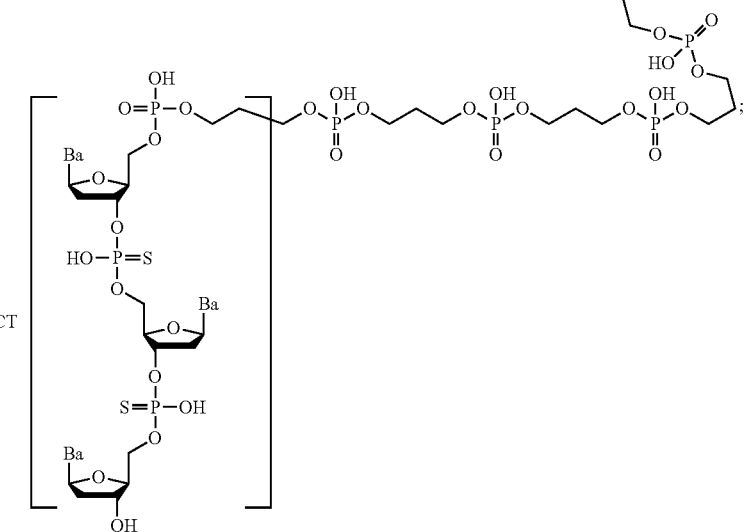
Sequence 5' to 3' =
TCC ATG AGC TTC CTG ATG CT
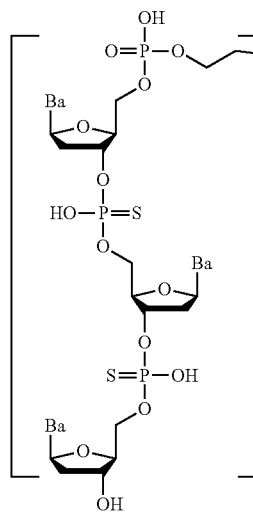
Sequence 5' to 3' =
TCC ATG AGC TTC
CTG ATG CT
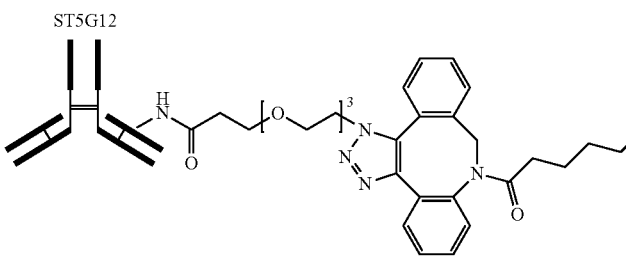

107
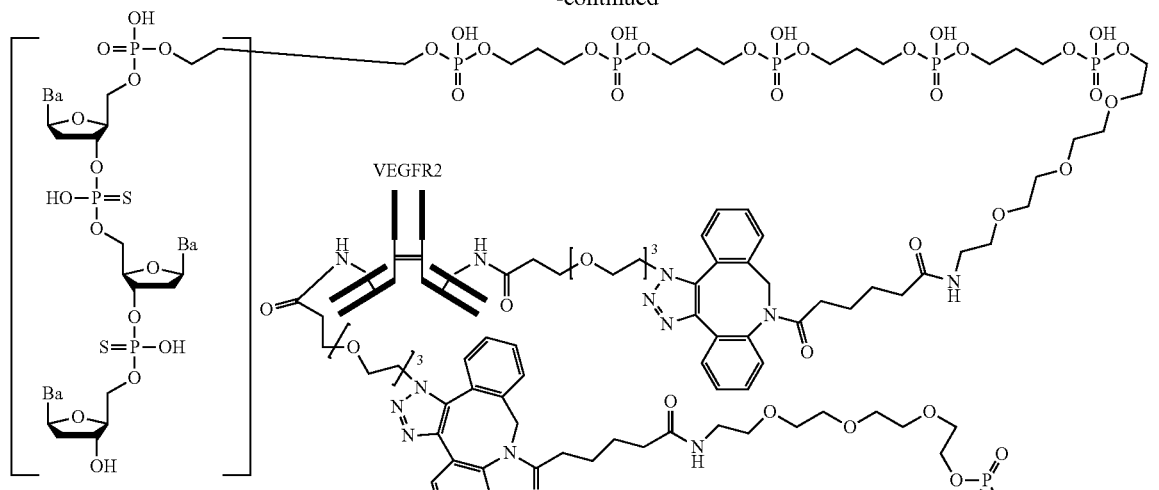
-continued
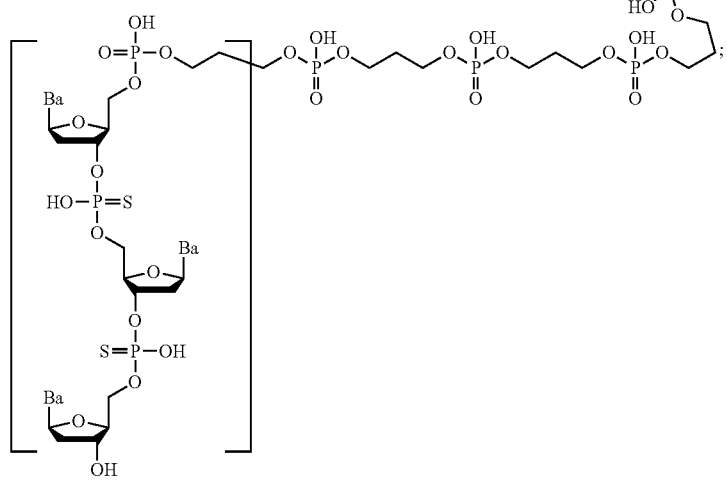
108
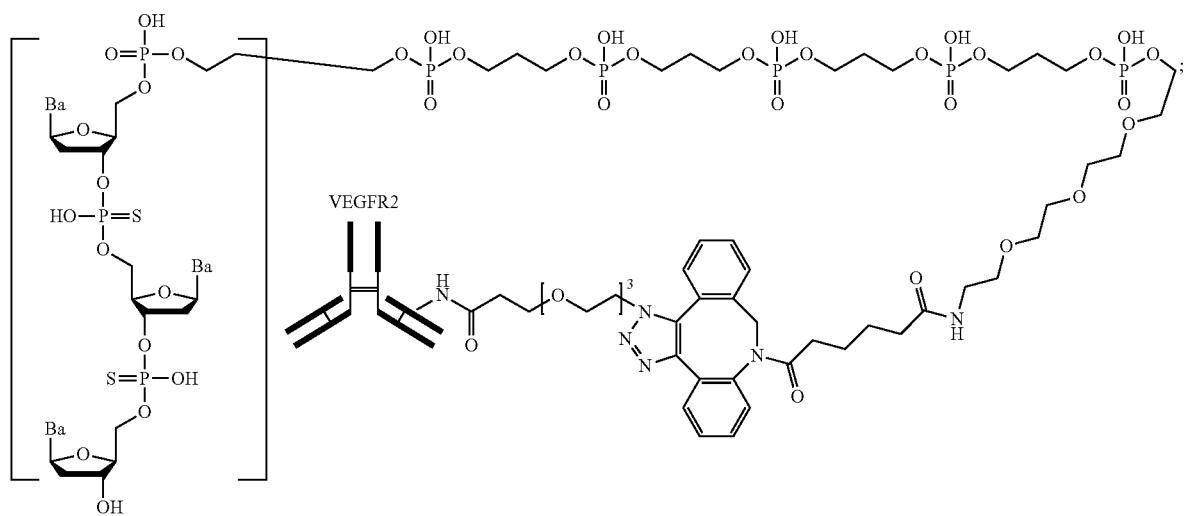

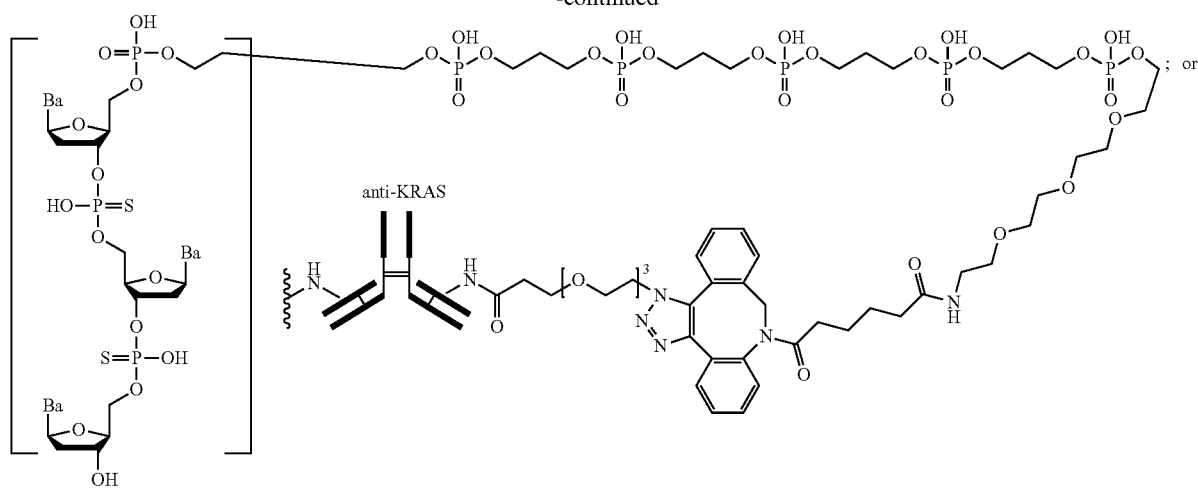
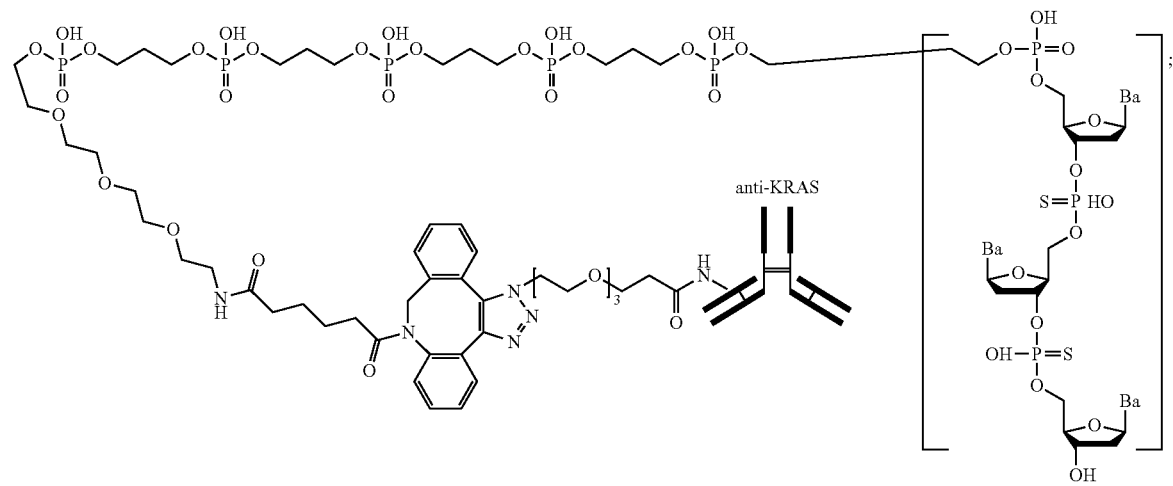

or a pharmaceutically acceptable salt thereof ("TCCAT-GAGCTTCCTGATGCT" disclosed as SEQ ID NO.: 5).

27. A pharmaceutical composition comprising the compound of claim 1, or a pharmaceutically acceptable salt thereof; and a pharmaceutically acceptable carrier.

28. A method of treating a disease or disorder selected from autoimmune disease, developmental disorder, inflammatory disease, metabolic disorder, cardiovascular disease, liver disease, intestinal disease, infectious disease, endocrine disease, neurological disorder, and cancer in a subject in need thereof, comprising administering to the subject a therapeutically effective amount of a compound of claim 1, or a pharmaceutically acceptable salt thereof.

29. A process for producing a compound having the Formula I:

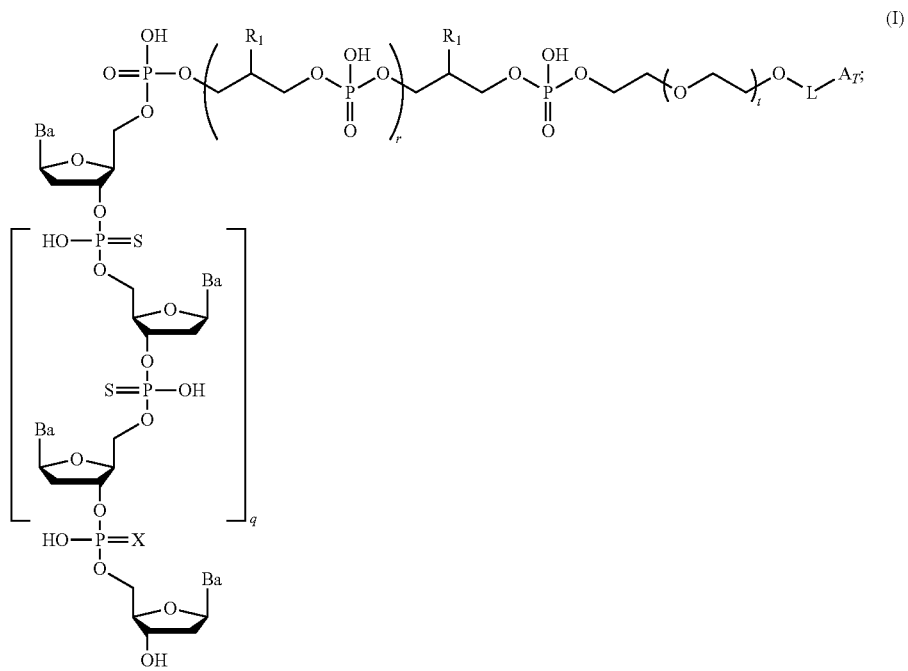

(I)

$R^f$ is

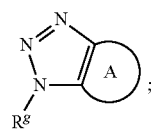

ring A is

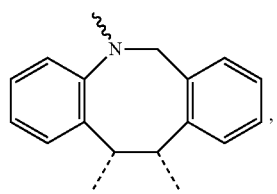

wherein, each Ba is independently selected from adenine (A), guanine (G), cytosine (C), and thymine (T);

X is O or S;

each $R_1$ is independently selected from hydrogen and ($C_1$-$C_6$)alkyl substituted with a fluorophore;

q is an integer from 12 to 35;

r is an integer from 1 to 10;

t is an integer from 1 to 10;

L is —$CH_2$—$R^2$—*;

$R^2$ is —($C_1$-$C_6$)alkyl-$NR^aC$(=O)$R^b$;

$R^a$ is hydrogen or ($C_1$-$C_6$)alkyl;

$R^b$ is ($C_1$-$C_6$)alkyl substituted with $R^f$ or —C(=O)$R^f$;

wherein the dashed bonds indicate the points of attachment to the triazolyl of $R^f$ and the wavy bond indicates the point of attachment to the ($C_1$-$C_6$)alkyl or carbonyl each defined by $R^b$; and $R^g$ is ($C_1$-$C_6$)alkyl or —[($C_1$-$C_6$)alkyl-O—($C_1$-$C_6$)alkyl]$_w$C(=O)NH;

w is an integer from 2 to 12;

* indicates the point of attachment to $A_T$; and $A_T$ is an antibody;

the process comprising reacting a compound having the Formula 100:

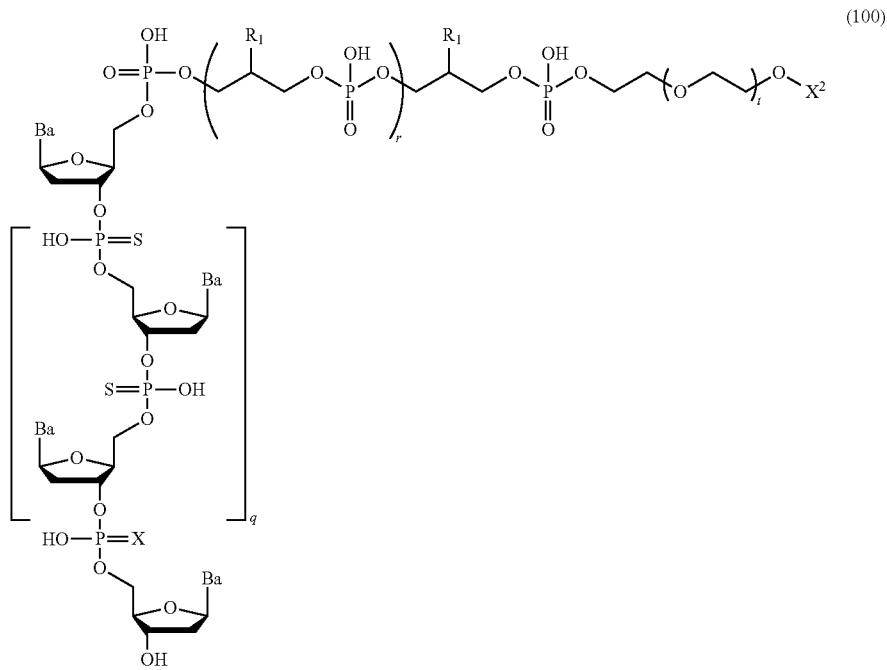
wherein
$X^2$ is —CH$_2$(C$_1$-C$_6$)alkyl-NR$^a$C(=O)R$^b$;
R$^a$ is hydrogen or (C$_1$-C$_6$)alkyl;
R$^b$ is (C$_1$-C$_6$)alkyl substituted with R$^{40}$ or —C(=O)R$^{40}$; and
R$^{40}$ is
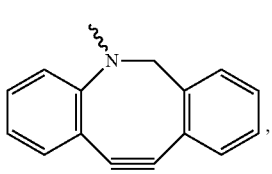
wherein the wavy line indicates the point of attachment to the (C$_1$-C$_6$)alkyl or carbonyl defined by R$^b$;
with a compound having the Formula A$_T$-Y, wherein Y is —R$^g$N$_3$.
* * * * *

SEQUENCE LISTING

<160> NUMBER OF SEQ ID NOS: 5

<210> SEQ ID NO 1
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Gly Leu Gly Trp Gly Thr Tyr Phe Arg Leu Gly Asp
            100                 105                 110

Ala Phe Asp Ile Trp Gly Gln Gly Thr Met Val Thr Val Ser Ser
        115                 120                 125

<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Glu
            20                  25                  30

Gly Ala Ala Trp Leu Gln Gln His Gln Gly His Pro Pro Lys Leu Leu
        35                  40                  45

Ser Tyr Arg Asn Phe Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala Trp Val Phe Gly Gly Gly Thr Lys Leu Thr Val Leu
            100                 105                 110

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Asp Tyr Val His Ser Phe Asp Ile Trp Gly Gln Gly Thr
            100                 105                 110

Met Val Thr Val Ser Ser
        115

<210> SEQ ID NO 4
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Pro Val Leu Thr Gln Pro Pro Ser Ala Ser Ala Leu Leu Gly Ala
1               5                   10                  15

Ser Ile Lys Leu Thr Cys Thr Leu Ser Ser Glu His Ser Thr Tyr Thr
            20                  25                  30

Val Glu Trp Tyr Gln Gln Arg Pro Gly Arg Ser Pro Gln Tyr Ile Met
        35                  40                  45

Asn Val Lys Ser Asp Gly Ser Tyr Asn Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
            85                  90                  95

Arg Ile Asp Gly Gln Val Gly Val Val Phe Gly Gly Gly Thr Lys Leu
            100                 105                 110

Thr Val Leu
        115

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tccatgagct tcctgatgct                                            20